United States Patent
Kaspar

(10) Patent No.: US 9,539,307 B2
(45) Date of Patent: Jan. 10, 2017

(54) COMPOSITIONS AND METHODS FOR TREATING AMYOTROPHIC LATERAL SCLEROSIS

(71) Applicant: THE RESEARCH INSTITUTE AT NATIONWIDE CHILDREN'S HOSPITAL, Columbus, OH (US)

(72) Inventor: Brian Kaspar, New Albany, OH (US)

(73) Assignee: The Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 14/428,765

(22) PCT Filed: Sep. 17, 2013

(86) PCT No.: PCT/US2013/060153
§ 371 (c)(1),
(2) Date: Mar. 17, 2015

(87) PCT Pub. No.: WO2014/043696
PCT Pub. Date: Mar. 20, 2014

(65) Prior Publication Data
US 2015/0231207 A1 Aug. 20, 2015

Related U.S. Application Data

(60) Provisional application No. 61/702,030, filed on Sep. 17, 2012.

(51) Int. Cl.
A61K 48/00 (2006.01)
C07H 21/02 (2006.01)
(Continued)

(52) U.S. Cl.
CPC ....... *A61K 38/1774* (2013.01); *A61K 31/7105* (2013.01); *A61K 48/00* (2013.01)

(58) Field of Classification Search
USPC .......................................... 514/44; 536/24.5
See application file for complete search history.

(56) References Cited

U.S. PATENT DOCUMENTS 5,173,414 A 12/1992 Lebkowski et al.
5,658,776 A 8/1997 Flotte et al.
(Continued)

FOREIGN PATENT DOCUMENTS

AU 2001294088 2/2002
WO 95/13365 5/1995
(Continued)

OTHER PUBLICATIONS

Cheung et al. (PNAS, 2011, published ahead of print Jul. 11, 2011, vol. 108(30):12372-12377). Also included is Supplementary Data pp. 1-337.*

(Continued)

*Primary Examiner* — Terra C Gibbs
(74) *Attorney, Agent, or Firm* — Barnes & Thornburg LLP

(57) ABSTRACT

The invention relates to pharmaceutical compositions, kits, methods, and uses for the treatment of amyotrophic lateral sclerosis. In particular, the invention relates to pharmaceutical compositions, kits, methods, and uses for the treatment of amyotrophic lateral sclerosis by decreasing the expression of a cytoplasmic granule toxin in astrocytes of a patient, or by increasing the expression of MHC class I in motor neurons of the patient.

6 Claims, 48 Drawing Sheets

(51) Int. Cl.
  C07H 21/04    (2006.01)
  C12N 15/11   (2006.01)
  A61K 38/17   (2006.01)
  A61K 31/7105  (2006.01)

(56) References Cited

U.S. PATENT DOCUMENTS

| | | |
|---|---|---|
| 5,786,211 A | 7/1998 | Johnson et al. |
| 5,871,982 A | 2/1999 | Wilson et al. |
| 6,258,595 B1 | 7/2001 | Gao |
| 6,566,118 B1 | 5/2003 | Atkinson |
| 6,723,315 B1 | 4/2004 | Mallet et al. |
| 2004/0009479 A1 | 1/2004 | Wohlgemuth et al. |
| 2005/0053922 A1 | 3/2005 | Schaffer et al. |
| 2009/0202490 A1 | 8/2009 | Schaffer et al. |
| 2010/0081705 A1 | 4/2010 | Bennett et al. |
| 2010/0152053 A1 | 6/2010 | Russwurm |
| 2011/0053861 A1 | 3/2011 | Xie et al. |
| 2012/0177605 A1 | 7/2012 | Kaspar et al. |

FOREIGN PATENT DOCUMENTS

| | | |
|---|---|---|
| WO | 95/13392 | 5/1995 |
| WO | 96/17947 | 6/1996 |
| WO | 97/06243 | 2/1997 |
| WO | 97/08298 | 3/1997 |
| WO | 97/09441 | 3/1997 |
| WO | 97/21825 | 6/1997 |
| WO | 98/09657 | 3/1998 |
| WO | 98/18600 | 5/1998 |
| WO | 99/11764 | 3/1999 |
| WO | 01/83692 | 11/2001 |
| WO | 2005/096781 | 10/2005 |
| WO | 2006/066203 | 6/2006 |
| WO | 2009/013290 | 1/2009 |
| WO | 2009/043936 | 4/2009 |
| WO | 2009/102427 | 8/2009 |
| WO | 2010/071832 | 6/2010 |
| WO | 2011/133890 | 10/2011 |
| WO | 2012/058220 | 5/2012 |
| WO | 2012/121403 | 9/2012 |
| WO | 2013/078316 | 5/2013 |
| WO | 2013/123503 | 8/2013 |
| WO | 2014/052753 | 4/2014 |
| WO | 2014/071219 | 5/2014 |

OTHER PUBLICATIONS

Gasque et al., Identification of Astrocyte Cell Population from Human Brain that Expresses Perforin, a Cytotoxic Protein Implicated in Immune Defense, J Exp Med, 1998, 187(4): 451-460.
Ilzecka, Granzymes A and B levels in serum of patients with amyotrophic lateral sclerosis, Clin Biochem, 2011, 44(8-9): 650-653.
Haidet-Phillips et al, Astrocytes from familial and sporadic ALS patients are toxic to motor neurons, Nat Biotech, 2011, 29(9): 824-828.
GenBank: M28393.1, Human perforin mRNA, complete cds (retrieved on Apr. 3, 2014 from http://www.ncbi.nlm.nih.gov/nuccore/M28393), 1995.
Marchetto, M.C. et al. Non-cell-autonomous effect of human SOD1 G37R astrocytes on motor neurons derived from human embryonic stem cells. *Cell Stem Cell* 3, 649-657 (2008).
PCT International Search Report/Written Opinion for PCT/US2013/060153, completed on Apr. 3, 2014.
Sambrook et al., "Molecular Cloning: A Laboratory Manual", 3rd Edition, Cold Spring Harbor Laboratory Press, (2001). Book Reference available upon specific request request from Examiner.
Zamecnik, et al., "Inhibition of replication and expression of human T-cell lymphotropic virus type III in cultured cells by exogenous synthetic oligonucleotides complementary to viral RNA," Proc. Natl. Acad. Sci. 83:4143-4146 (1986).
Foust, K.D., et al. Intravascular AAV9 preferentially targets neonatal neurons and adult astrocytes. Nat Biotechnol, 27, 59-65 (2008).
Remington: The Science & Practice of Pharmacy, 21st Edition (Lippincott Williams & Wilkins, 2005). Book Reference available upon specific request request from Examiner.
Tiscornia et al., "Production and purification of lentiviral vectors," Nat Protoc, 2006, vol. 1, No. 1, 241-245.
Foust et al, Therapeutic AAV9-mediated Suppression of Mutant SOD1 Slows Disease Progerssion and Extends Survival in Models of Inherited ALS, Molecular Therapy, 21(12): 2148-2159 (2013).
Gray, S.J. et al. Preclinical differences of intravascular AAV9 delivery to neurons and glia: a comparative study of adult mice and nonhuman primates. *Mol Ther* 19, 1058-1069 (2011).
Thompson, A., van der Slik, A.R., Koning, F. & van Bergen, J. An improved RT-PCR method for the detection of killer-cell immunoglobulin-like receptor (KIR) transcripts. Immunogenetics, 58, 865-872 (2006).
Cardona et al, "Isolation of murine cells for RNA analysis or flow cytometry," Nature Protocols, vol. 1, No. 4, 2006, pp. 1947-1951.
Moussaud and Draheim, "A new method to isolate microglia from adult mice and culture them for an extended period of time," J. of Neuroscience Methods, 187, pp. 243-253, 2010.
Noble, M. & Mayer-Proschel, M. Culture of astrocytes, oligodendrocytes, and O-2A progenitor cells, (M IT press, Cambridge, 1998. Book Reference available upon specific request request from Examiner.
Wichterle et al,"Directed Differentiation of Embryonic Stem Cellsinto Motor Neurons," Cell, vol. 110, Aug. 9, 2002, pp. 385-397.
Miranda, C.J. et al. Aging brain microenvironment decreases hippocampal neurogenesis through Wnt-mediated surviving signaling. *Aging Cell* 11, 542-552 (2012).
Di Giorgio, F.P., Carrasco, M.A., Siao, M.C., Maniatis, T. & Eggan, K. Non-cell autonomous effect of glia on motor neurons in an embryonic stem cell-based ALS model. *Nature neuroscience* 10, 608-614 (2007).
Ray, J. & Gage, F.H. Differential properties of adult rat and mouse brain-derived neural stem/progenitor cells. Mol Cell Neurosci, 31, 560-573 (2006).
Nagai et al, "Astrocytes expressing ALS-linked mutated SOD1 release factors selectively toxic to motor neurons," Nature Neuroscience, vol. 10, No. 5, May 2007.
Wang et al, Control of inducible chemoresistance: Enhanced antitimor therapythrough increased apoptosis by inhibition of NG-KB, Nature Medicine, vol. 5, No. 4, Apr. 1999, pp. 412-417.
Li et al, "IKKβ is Required for Peripheral B Cell Survival and Proliferation," The Journal of Immunology, 2003. pp. 4630-4637.
Park et al, "Macrophage Apoptosis by Anthrax Lethal Factor Through p38 MAP Kinase Inhibition," Science, vol. 297, Sep. 20, 2002, pp. 2048-2051.
Crosio et al, 2011, Astroglial Inhibtition of NF-KB Does not Ameliorate Disease Onset and Progression in a Mouse Model for Amyotrophic Lateral Sclerosis (ALS), PLoS One, 6(3): e17187.
Magness et al., "In vivo pattern of lipopolysaccharide and anti-DC3-induced NF-kB activation using a novel gene-targeted GFP Reporters Gene Mouse,"The Journal of Immunology, 2004; 173:1561-1570.
Xiao et al, "Mutant SOD1$^{G93A}$ microglia are more neurotoxic relative towild-type microglia," Jounal of Neurochemistry, 2007, vol. 102, pp. 2008-2019.
Swarup et al, Deregulation of TDP-43 in amyotrophic lateral sclerosis triggers nuclear factor KB-mediated pathogenic pathways, J Exp Med, 208(12): p. 2429-2447.
Ghosh and Karin, "Missing Pieces in the NF-kB Puzzle," Cell, vol. 108, 2002.s.
Erblich et al, "Absence of Colony stimulation Factor-1 Receptor Results in Loss of Microglia, Disrupted Brain Development and Olfactory Deficits," Plos One/www.plosone.org; Oct. 2011, vol. 6, No. 10, pp. e26317.

(56) References Cited

OTHER PUBLICATIONS

Sasmono et al,"A macrophage colony-stimulating factor receptor-green fluorescent protein transgene is expressed throughout the mononuclear phagocyte system of the mouse," Blood, Feb. 1, 2003, vol. 101, No. 3, pp. 1155-.1163.
Ruocco et al, "iKB kinase (IKK)β, but not IKKαm is a critical mediator of osteoclast survival and is required for inflammation-induced bone loss," The Journal of Experimental Medicine, vol. 201, No. 10, May 16, 2005, pp. 1677-1687.
Vallabhupurapu and Karin,"Regulatioin and Functionof NF-kB Transcription Factors in the Immune System," Annu. Rev. Immunol. 2009, 27:693-733.
Kigerl et al,, "Identification of Two Distinct Macrophage Subsets with Divergent Effects Causing either Neurotoxicity or Regeneration in the Injured Mouse Spinal Cord," The Journal of Neuroscience, Oct. 20, 2009, pp. 13435-13444.
Beers et al, "Neuroinflammation modulates distinct regional and temporal clinical responses in ALS mice," Brain, Behavior and Immunity, 25, 2011, pp. 1025-1035.
Norden and Godbout, "Review: Microglia of the aged brain: primed to be activated and resistant to regulation," Neuropathology and Applied Neurobiology, vol. 39, 2013, pp. 19-34.
Dahlman & Guttridge, "Detection of NF-k-B Activityin Skeletal Muscle Cells by Electrophoretic Mobility Shift Analysis," Methods of Mol. Biol., Chapter 30, pp. 505-516, 2012.
Lioy, D.T. et al. A role for glia in the progression of Rett's syndrome. Nature 475, 497-500 (2011).
Foust et al, "Rescue of the spinalmuscular atrophy phenotype in a mousemodel by early postnatal deliveryof SMN," Nature Biotechnology, vol. 28, No. 3, Mar. 2010 (pp. 271-276).
Rao et al., "A tripotential glial precursor cell is present in the developing spinal cord," Proc. Natl. Acad. Sci. USA, vol. 95, pp. 3996-4001, Mar. 1998.
Henry et al, "Peripheral lipopolysaccharide (LPS) challenge promotes microglial hyperactivity in aged mice that is associated with exaggerated induction of both pro-inflammatory IL-1βand anti-inflammatory IL-10 cytokines," Brain, Behavior, and Immunity 23 92009), pp. 309-317.
Guareschi, S. et al. An over-oxidized form of superoxide dismutase found in sporadic amyotrophic lateral sclerosis with bulbar onset shares a toxic mechanism with mutant SOD1. Proc Natl Acad SciUSA 109, 5074-5079 (2012).
Sommer et al, Quanitifcation of Adeno-Associated Virus partciles and Empty Capsids by Optical Density Measurement, Mol Therapeutics, (2003), 7(1): 122-128.
PCT International Search Report/Written Opinion for PCT/US2014/ 063890, completed on Feb. 20, 2015.
Frakes, A.E., et al. Microglia induce motor neuron death via the classical NFkappaB pathway in amyotrophic lateral sclerosis. Neuron, 81, 1009-1023 (2014).
Meyer, K., et al. Direct conversion of patient fibroblasts demonstrates non-cell autonomous toxicity of astrocytes to motor neurons in familial and sporadic ALS. Proc Natl Acad Sci U S A, 111, 829-832 (2014).
Hester, M.E., et al. Two factor reprogramming of human neural stem cells into pluripotency. PLoS One, 4, e7044 (2009).
Kim, J.B., et al. Pluripotent stem cells induced from adult neural stem cells by reprogramming with two factors. Nature, 454, 646-650 (2008).
Kaech, S. & Banker, G. Culturing hippocampal neurons. Nat Protoc, 1, 2406-2415 (2006).
McConnell, M.J., Huang, Y.H., Datwani, A. & Shatz, C.J. H2-K(b) and H2-D(b) regulate cerebellar long-term depression and limit motor learning. Proc Natl Acad Sci U S A, 106, 6784-6789 (2009).
Syken, J. & Shatz, C.J. Expression of T cell receptor beta locus in central nervous system neurons. Proc Natl Acad Sci U S A, 100, 13048-13053 (2003).
Nardo, G., et al. Transcriptomic indices of fast and slow disease progression in two mouse models of amyotrophic lateral sclerosis. Brain 136, 3305-3332 (2013).

Thams, S., et al. Classical major histocompatibility complex class I molecules in motoneurons: new actors at the neuromuscular junction. J Neurosci 29, 13503-13515 (2009).
Dodge, J.C., et al. Delivery of AAV-IGF-1 to the CNS extends survival in ALS mice through modification of aberrant glial cell activity. Mol Ther 16, 1056-1064 (2008).
Re, D.B., et al. Necroptosis drives motor neuron death in models of both sporadic and familial ALS. Neuron 81, 1001-1008 (2014).
Goodridge, J.P., Burian, A., Lee, N. & Geraghty, D.E. HLA-F and MHC class I open conformers are ligands for NK cell Ig-like receptors. J Immunol 191, 3553-3562 (2013).
PCT International Search Report/Written Opinion for PCT/US2014/ 052753, completed on Nov. 24, 2014.
Kaplitt et al, "Safety and tolerability of gene therapy with an adeno-associated virus (AAV) borne GAD gene for Parkinson's disease: an open label, phase I trial," Lancet 369: 2097-2105, 2007.
Marks et al, "Safety and tolerability of intraputaminal delivery of CERE-120 (adeno-associated virus serotype 2-neurturin) to patients with idiopathic Parkins's disease: an open-label, phase I trial," Lancet Neurol 7: 400-.
Worgall et al, "Treatment of late infantile neuronal ceroid lipofuscinosis by CNS administration of a sterotype 2 adeno-associated virus expressing CLN2 cDNA," Hum Gen Ther, 19:463-474, May 2008.
Srivastava et al, "Nucleotide Sequence and Organization of the Adeno-Associated virus 2 Genome," J. Virol, 45: 555-564, (1983).
Ruffing et al, J Gen Virol, 75: 3385-3392 (1994).
Pacak et al, "Recombinant AdenoAssociated virus Serotype 9 Leads to Preferential Cardiac Transduction In Vivo," Circ Res, 99(4): 3-9 (1006).
Wang et al, "Adeno-associated virus serotype 8 efficiently delivers genes to muscle and heart," Nature Biotech, 23(3), 321-328, (2005).
Grimm et al, Adeno-associated virus vectors for short hairpin RNA Expression, Methods in Enzymology, Academic Press, US, vol. 392, (2005), pp. 381-405. Book Reference available upon specific request from Examiner.
Machida et al, Intraperitoneal administration of AAV9-shRNA inhibits target gene expression in the forsal root ganglia of neonatal mice, Molecular Pain, Biomed Central, 9(1): 36, (2013).
Ding et al, Selective siliencing by RNAi of a dominant allele that causes amyotrophic lateral sclerosis, Aging Cell, Blackwell Publichsing, vol. 2, pp. 209-217, (2003).
Musatov et al, RNAi-mediated silencing of estrogen receptor in ventromedial nucleus of hypothalamus abolishes female sexual behaviors, PNAS, 103(27): pp. 10456-10460, (2006).
Muzyczka, Current Topics in Microbiology and Immunology, 158:97-129(1992). Book Reference available upon specific request request from Examiner.
Gao et al."Clades of Adeno-Associated Viruses Are Widely Disseminated in Human Tissues," J. Virol., 78: 6381-6388 (2004).
De et al., "High Levels of Persistnet Expression of α1-Antitrpsin Mediated by the Nonhuman Primte Serotype rh.10 Adeno-associated Virus Despite Preexisting Immunity t Common Human Adeno-associated viruses," Mol. Ther., 13(1): 67-76 (2006).
Mori et al., "Two novel adeno-associated viruses from cynomolgus monkey: pseudotyping characterization of capsid protein," Virology, 330(2): 375-383 (2004).
Samulski et al., "Cloning of adeno-associated virus into pBR322: Rescue of intact virus from the recombinant plasmid in human cells," Proc. Natl. Acad. Sci. USA, vol. 79, pp. 2077-2081, Mar. 1982.
Laughlin et al., 1983, Gene, 23:65-73.
Senapathy & Carter, "Molecular Cloning of Adeno-associated Virus Variant Genomes and Generation of Infectious Virus by Recombination in Mammalian Cells," 1984, J. Biol. Chem., vol. 259, No. 7, pp. 4661-4666.
Carter, "Adeno-associated virus vectors," 1992, Current Opinions in Biotechnology, 533-539.
Tratschin et al., "A Human Parvovirus, Adeno-Associated virus, as a Eucaryotic Vector: Transient Expresson and Encapsidation of the Procaryotic Gene for Chloramphenicol Acetyltransferase,"Mol. Cell. Biol. 4:2072 (1984).

(56) References Cited

OTHER PUBLICATIONS

Hermonat et al., "Use of adeno-associated virus as a mammalian DNA cloning vector: Transduction of neomycin resistance into mammalian tissue culture cells," Proc. Natl. Acad. Sci. USA, 81:6466 (1984).
Tratschin et al., "Adeno-Associated Virus Vector for High-Frequency Integration, Expression, and Rescue of Genes in Mammalian Cells," Mol. Cell. Biol. 5:3251 (1985).
McLaughlin et al., "Adeno-Associated Virus General Transduction Vectors: Analysis of Proviral Structures," J. Virol., 62:1963 (1988).
Lebkowski et al., "Adeno-Associated Virus: a Vector System for Efficient Introduction and Integratioin ofDNA into a Variety of Mammalian Cell Types," 1988 Mol. Cell. Biol., 7:349 (1988).
Samulski et al. "Helper-Free Stocks of Recombinant Adeno-Associated viruses: Normal Integration Does Not Require Viral Gene Expression," (1989, J. Virol., 63:3822-3828).
Perrin et al., "An experimental rabies vaccine produced with a new BHK-21 suspension cell culture process: use of serum-free medium and perfusion-reactor system," (1995) Vaccine 13:1244-1250.
Paul et al., "Increased viral titer through concentration of viral harvests from retroviral packaging lines," (1993) Human Gene Therapy 4:609-615.
Clark et al. (1996) Gene Therapy 3:1124-1132.
Clark et al, "Highly purified recombinant adeno-associated virus vectors are biologically active and free of detectable helper and wild-type viruses," Hum. Gene Ther., 10(6): 1031-1039 (1999).
Schnepp and Clark, "Highly Purified Recombinant Adeno-Associated Virus Vectors," Methods Mol. Med.., 69: 427-443 (2002).
Da Cruz, S. & Cleveland, D.W. Understanding the role of TDP-43 and FUS/TLS in ALS and beyond. Curr Opin Neurobiol 21, 904-919 (2011).
Rosen, D.R. et al. Mutations in Cu/Zn superoxide dismutase gene are associated with familial amyotrophic lateral sclerosis. Nature 362, 59-62 (1993).
Ilieva, H., Polymenidou, M. & Cleveland, D.W. Non-cell autonomous toxicity in neurodegenerative disorders: ALS and beyond. The Journal of cell biology 187, 761-772 (2009).
Chattopadhyay, M. & Valentine, J.S. Aggregation of copper-zinc superoxide dismutase in familial and sporadic ALS. Antioxidants & redox signaling 11, 1603-1614 (2009).
Prudencio, M., Hart, P.J., Borchelt, D.R. & Andersen, P.M. Variation in aggregation propensities among ALS-associated variants of SOD1 : correlation to human disease. Human molecular genetics 18, 3217-3226 (2009).
Boillee, S. et al. Onset and progression in inherited ALS determined by motor neurons and microglia. Science 312, 1389-1392 (2006).
Kang, S.H. et al. Degeneration and impaired regeneration of gray matter oligodendrocytes in amyotrophic lateral sclerosis. Nature neuroscience 16, 571-579 (2013).
Yamanaka, K. et al. Astrocytes as determinants of disease progression in inherited amyotrophic lateral sclerosis. Nature neuroscience 11, 251-253 (2008).
Di Giorgio, F.P., Boulting, G.L., Bobrowicz, S. & Eggan, K.C. Human embryonic stem cell-derived motor neurons are sensitive to the toxic effect of glial cells carrying an ALS-causing mutation. Cell Stem Cell 3, 637-648 (2008).
Yamanaka, K. et al. Mutant SOD1 in cell types other than motor neurons and o l igodendrocytes accelerates onset of disease in ALS mice. Proc Natl Acad Sci USA 105, 7594-7599 (2008).
Bevan, A.K. et al. Systemic gene delivery in large species for targeting spinal cord, brain, and peripheral tissues for pediatric disorders. Mol Ther 19, 1971-1980 (2011).
Bosco, D.A. et al. Wild-type and mutant SOD1 share an aberrant conformation and a common pathogenic pathway in ALS. Nature neuroscience 13, 1396-1403 (2010).
Pokrishevsky, E. et al. Aberrant localization of FUS and TDP43 is associated with misfolding of SOD1 in amyotrophic lateral sclerosis. PloS one 7, e35050 (2012).
Forsberg, K. et al. Novel antibodies reveal inclusions containing non-native SOD1 in sporadic ALS patients. PLoS One 5, el 1552 (2010).
Aggarwal, S. & Cudkowicz, M. ALS drug development: reflections from the past and a way forward. Neurotherapeutics : the journal of the American Society for Experimental Neuro Therapeutics 5, 516-527 (2008).
Gurney, M.E. et al. Benefit of vitamin E, riluzole, and gabapentin in a transgenic model of familial amyotrophic lateral sclerosis. Ann Neurol 39, 147-157 (1996).
Duque, S. et al. Intravenous administration of self-complementary AAV9 enables transgene delivery to adult motor neurons. Mol Ther 17, 1187-1196 (2009).
Zhong, Z. et al. ALS-causing SOD1 mutants generate vascular changes prior to motor neuron degeneration. Nature neuroscience 11, 420-422 (2008).
Miller, R.G., Mitchell, J.D. & Moore, D.H. Riluzole for amyotrophic lateral sclerosis (ALS)/motor neuron disease (MND). Cochrane Database Syst Rev 3, CD001447 (2012).
Smith, R.A. et al. Antisense oligonucleotide therapy for neurodegenerative disease. The Journal of clinical investigation 116, 2290-2296 (2006).
Raoul, C. et al. Lentiviral-mediated silencing of SOD1 through RNA interference retards disease onset and progression in a mouse model of ALS. Nat Med 11, 423-428 (2005).
Ralph, G.S. et al. Silencing mutant SOD1 using RNAi protects against neurodegeneration and extends survival in an ALS model. Nat Med 11, 429-433 (2005).
Miller, T.M. et al. Virus-delivered small RNA silencing sustains strength in amyotrophic lateral sclerosis. Annals of neurology 57, 773-776 (2005).
Miller, T.M. et al. A Phase I, Randomised, First-in-Human Study of an Antisense Oligonucleotide Directed Against SOD1 Delivered Intrathecally in SOD1-Familial ALS Patients. Lancet neurology 12, 435-442 (2013).
Towne, C., Raoul, C., Schneider, B.L. & Aebischer, P. Systemic AAV6 delivery mediating RNA interference against SOD1: neuromuscular transduction does not alter disease progression in fALS mice. Mol Ther 16, 1018-1025 (2008).
Towne, C., Setola, V., Schneider, B.L. & Aebischer, P. Neuroprotection by gene therapy targeting mutant SOD1 in individual pools of motor neurons does not translate into therapeutic benefit in fALS mice. Mol Ther 19, 274-283 (2011).
Mandel, R.J., Lowenstein, P.R. & Byrne, B.J. AAV6-mediated gene silencing fALS short. Mol Ther 19, 231-233 (2011).
Synofzik, M. et al. Mutant superoxide dismutase-1 indistinguishable from wild-type causes ALS. Human molecular genetics 21, 3568-3574 (2012).
Ił żcka et al., "Granzymes A and B levels in serum of patients with amyotrophic lateral Sclerosis," Clinical Biochemistry, 44(8):650-653 (2011). XP028209454.
Lewis et al., "Neuroinflammatory Response in ALS: The Roles of Microglia and T Cells," Neurology Research International, 23(12): 5197-8 (2012). XP055243845.
Trapani et al., "Functional significance of the perforin/granzyme death pathway," The Journal of Immunology, 2(10): 735-747 (2002). XP055243880.
Search Report issued in European Application No. 13837504.3 (Feb. 10, 2016).
Charcot, Jean Martin, Clinical Lectures on Diseases of the Nervous System, vol. III (1889), pp. 1 through 465.

\* cited by examiner

G

| | WT | | G93A | |
|---|---|---|---|---|
| | #1 | #2 | #1 | #2 |
| Prf1 | | | | |
| Gzmb | | | | |
| Actb | | | | |

| | Microglia | | Astrocytes | | | |
|---|---|---|---|---|---|---|
| | Primary | | Primary | | NPC derived | |
| | WT | G93A | WT | G93A | WT | G93A |
| Prf1 | | | | | | |
| Gzmb | | | | | | |
| Actb | | | | | | |

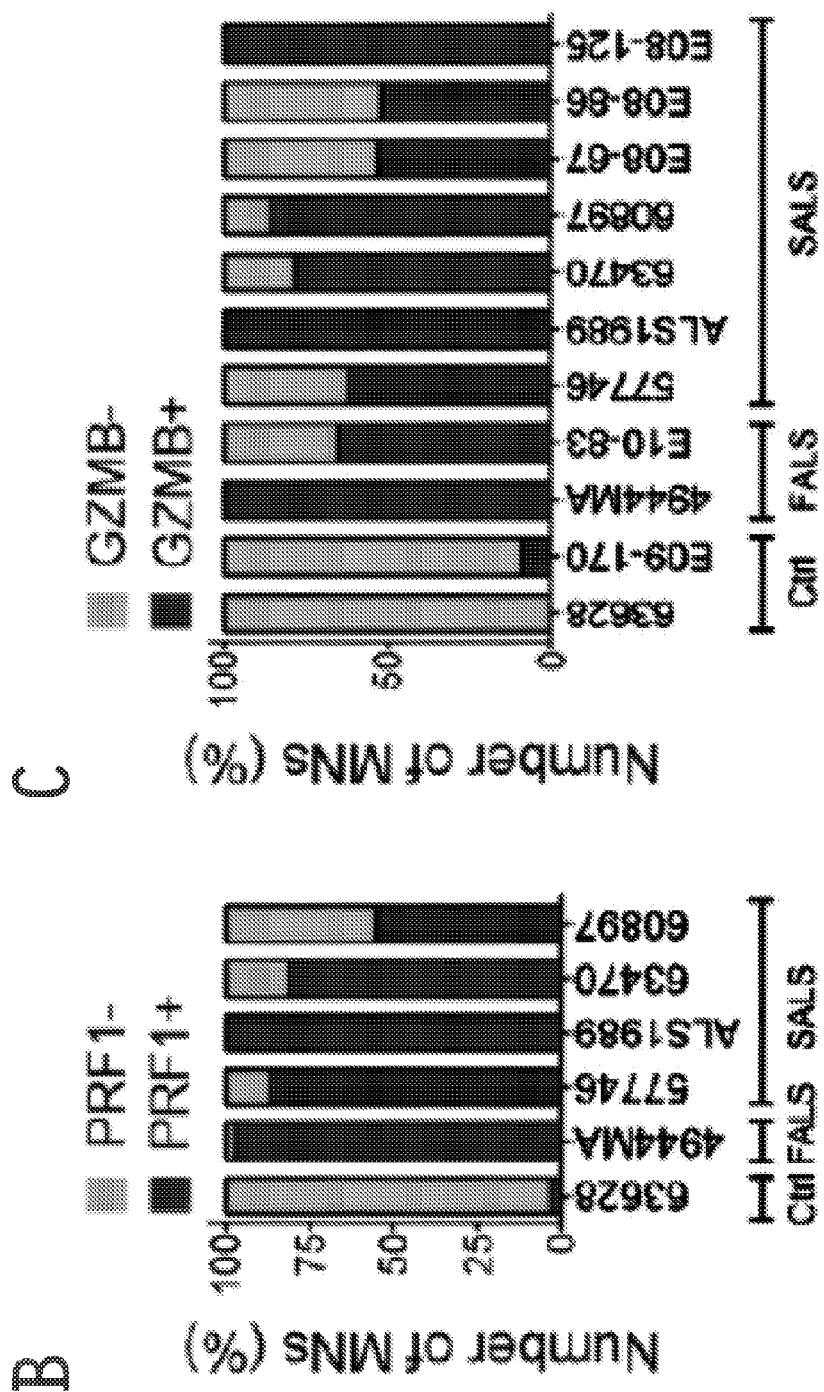

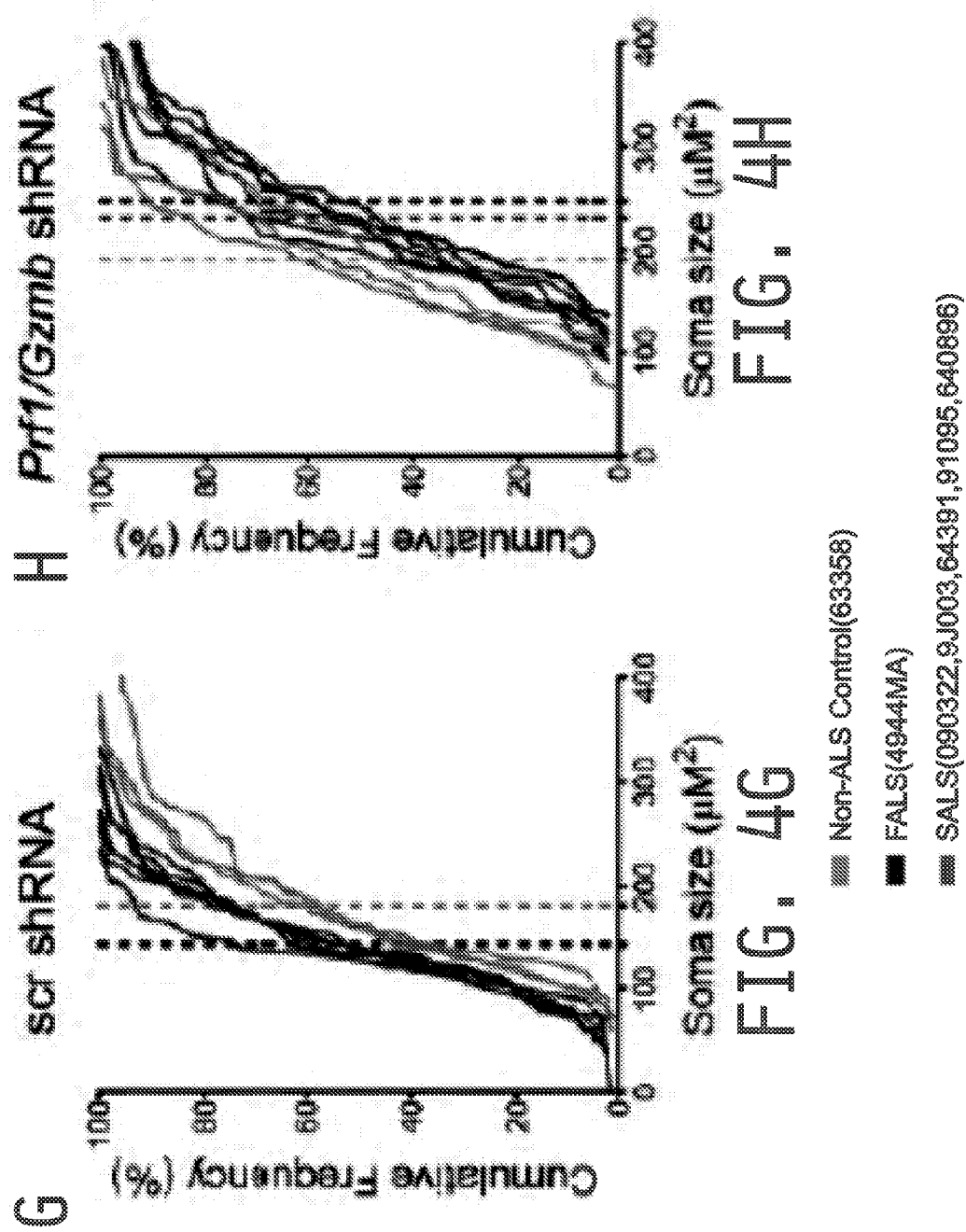

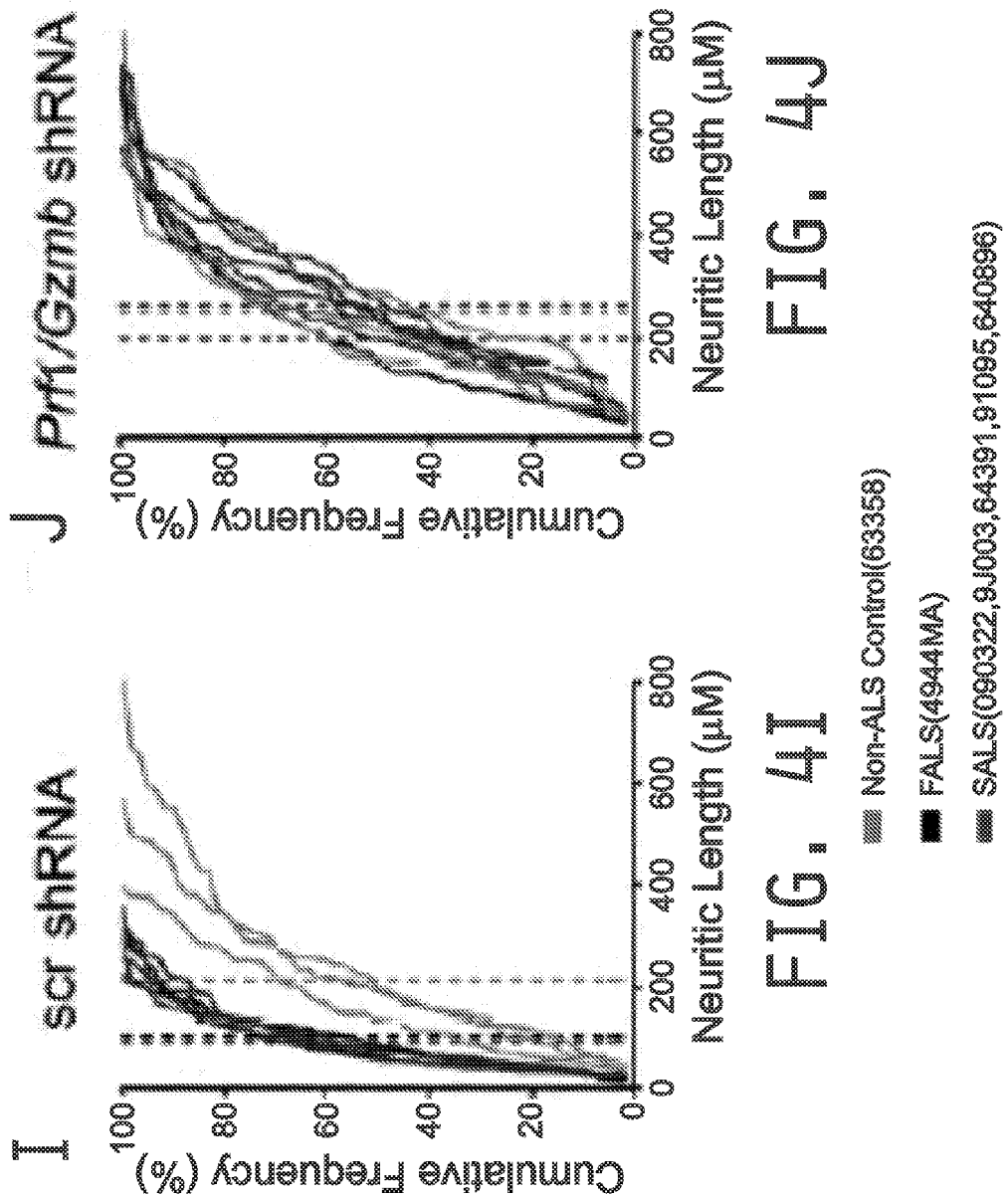

COMPOSITIONS AND METHODS FOR TREATING AMYOTROPHIC LATERAL SCLEROSIS

CROSS REFERENCE TO RELATED APPLICATIONS

This application is a national stage entry under 35 USC §371(b) of International Application No. PCT/US2013/060153, filed Sep. 17, 2013, which claims priority under 35 U.S.C. §119(e) to U.S. Provisional Application Ser. No. 61/702,030, filed Sep. 17, 2012, the disclosures of each of which are expressly incorporated by reference herein.

GOVERNMENT RIGHTS

This invention was made with government support under NRSAF31NS058224, R01 NS644912-1A1 and RC2 NS69476-01 awarded by the National Institutes of Health. The government has certain rights in the invention.

TECHNICAL FIELD

The invention relates to compositions, kits, methods, and uses for the treatment of amyotrophic lateral sclerosis. In particular, the invention relates to compositions, kits, methods, and uses for the treatment of amyotrophic lateral sclerosis by decreasing the expression of a cytoplasmic granule toxin in the astrocytes of a patient, or by increasing the expression of MHC class I in motor neurons of the patient.

BACKGROUND AND SUMMARY

Amyotrophic lateral sclerosis, commonly referred to as Lou Gehrig's disease, is characterized by selective, premature degeneration and death of motor neurons in the motor cortex, brain stem and spinal cord. The loss of motor neurons causes progressive muscle paralysis ultimately leading to death from respiratory failure. Approximately 90% of all amyotrophic lateral sclerosis cases are sporadic amyotrophic lateral sclerosis, without a family history of the disease, and the other approximately 10% of cases are cases of familial amyotrophic lateral sclerosis. Despite significant efforts to identify risk factors and potential susceptibility genes, the etiology of sporadic amyotrophic lateral sclerosis remains largely unknown.

Various rodent models carrying dominant mutations of the human superoxide dismutase (SOD1) that is causative in about 20% of familial amyotrophic lateral sclerosis cases, have been instrumental to model motor neuron toxicity in amyotrophic lateral sclerosis. These models have demonstrated that not only motor neurons, but also non-neuronal cell types including microglia and astrocytes play a significant role in disease onset and progression. Recent studies have identified astrocytes as mediators of motor neuron death in amyotrophic lateral sclerosis by a yet undetermined cytotoxic mechanism. Insight into the mechanisms underlying the acquisition of this toxic function by amyotrophic lateral sclerosis astrocytes is pertinent for the development of successful therapies for amyotrophic lateral sclerosis.

Accordingly, the present inventors have discovered the mechanism underlying the acquisition of this toxic function by amyotrophic lateral sclerosis astrocytes, and have used this knowledge to develop therapies for amyotrophic lateral sclerosis. The pharmaceutical compositions, methods and uses, and kits described herein can be used to treat sporadic or familial amyotrophic lateral sclerosis.

Several embodiments of the invention are described by the following enumerated clauses:

1. A method for treating a patient with amyotrophic lateral sclerosis by decreasing the expression of a cytoplasmic granule toxin in astrocytes of the patient, the method comprising the step of
   administering to the patient a composition comprising an effective amount of a compound that decreases the expression the cytoplasmic granule toxin in the astrocytes of the patient.
2. The method of clause 1 wherein the cytoplasmic granule toxin is a perforin.
3. The method of clause 2 wherein the perforin is perforin 1.
4. The method of clause 1 wherein the cytoplasmic granule toxin is a granzyme.
5. The method of clause 4 wherein the granzyme is granzyme B.
6. The method of any one of clauses 1 to 5 wherein the decreased expression of the cytoplasmic granule toxin results in an effect on motor neurons in the patient selected from the group consisting of an increase in the number of motor neurons, a decrease in soma atrophy, and an increase in neurite length after administration of the compound.
7. The method of any one of clauses 1 to 6 wherein the compound is selected from the group consisting of a drug, a peptide, and a nucleic acid.
8. The method of clause 7 wherein the compound is a nucleic acid.
9. The method of clause 8 wherein the nucleic acid functions by RNA interference or is an antisense RNA molecule.
10. The method of clause 8 wherein the nucleic acid is selected from the group consisting of an siRNA, an miRNA, and an shRNA.
11. The method of clause 10 wherein the nucleic acid is an shRNA.
12. The method of clause 8 wherein the nucleic acid is delivered to the patient in a bacterial vector or in a viral vector.
13. The method of clause 8 wherein the nucleic acid has the sequence of SEQ ID NO: 1.
14. The method of clause 8 wherein the nucleic acid has the sequence of SEQ ID NO: 2.
15. The method of any one of clauses 1 to 14 wherein the amyotrophic lateral sclerosis is sporadic amyotrophic lateral sclerosis.
16. The method of any one of clauses 1 to 14 wherein the amyotrophic lateral sclerosis is familial amyotrophic lateral sclerosis.
17. The method of any one of clauses 1 to 16 wherein the amount of the compound is in the range of about 1 ng/kg of patient body weight to about 1 mg/kg of patient body weight.
18. The method of any one of clauses 1 to 17 wherein the amount of the compound is in the range of about 1 ng/kg of patient body weight to about 500 ng/kg of patient body weight.
19. The method of any one of clauses 1 to 18 wherein the amount of the compound is in the range of about 1 ng/kg of patient body weight to about 100 ng/kg of patient body weight.
20. The method of any one of clauses 1 to 19 wherein the composition further comprises a carrier, an excipient, or a diluent, or a combination thereof.

21. The method of clause 20 wherein the composition comprises a pharmaceutically acceptable carrier, wherein the pharmaceutically acceptable carrier is a liquid carrier.

22. The method of clause 21 wherein the liquid carrier is selected from the group consisting of saline, glucose, alcohols, glycols, esters, amides, and a combination thereof.

23. The method of any one of clauses 1 to 22 wherein the composition is administered in a single-dose or a multiple-dose regimen.

24. A method for treating amyotrophic lateral sclerosis by increasing MHC class I expression in motor neurons of a patient, the method comprising the step of
    administering to the patient a composition comprising an effective amount of a compound that increases the expression of MHC class I in the motor neurons of the patient.

25. The method of clause 24 wherein the increased expression of the MHC class I results in an effect on motor neurons in the patient selected from the group consisting of an increase in the number of motor neurons, a decrease in soma atrophy, and an increase in neurite length after administration of the compound.

26. The method of any one of clauses 24 to 25 wherein the compound is selected from the group consisting of a drug, a peptide, and a nucleic acid.

27. The method of clause 26 wherein the compound is a nucleic acid.

28. The method of clause 27 wherein the nucleic acid is delivered to the patient in a bacterial vector or in a viral vector.

29. The method of clause 28 wherein the vector is a viral vector.

30. The method of clause 29 wherein the vector is selected from the group consisting of a lentiviral vector and an adenovirus vector.

31. The method of clause 30 wherein the nucleic acid has the sequence of SEQ ID NO: 3.

32. The method of clause 31 wherein the nucleic acid encodes the histocompatibility complex H2K.

33. The method of any one of clauses 24 to 32 wherein the amyotrophic lateral sclerosis is sporadic amyotrophic lateral sclerosis.

34. The method of any one of clauses 24 to 32 wherein the amyotrophic lateral sclerosis is familial amyotrophic lateral sclerosis.

35. The method of any one of clauses 24 to 34 wherein the amount of the compound is in the range of about 1 ng/kg of patient body weight to about 1 mg/kg of patient body weight.

36. The method of any one of clauses 24 to 35 wherein the amount of the compound is in the range of about 1 ng/kg of patient body weight to about 500 ng/kg of patient body weight.

37. The method of any one of clauses 24 to 36 wherein the amount of the compound is in the range of about 1 ng/kg of patient body weight to about 100 ng/kg of patient body weight.

38. The method of any one of clauses 24 to 37 wherein the composition further comprises a carrier, an excipient, or a diluent, or a combination thereof.

39. The method of clause 38 wherein the composition comprises a pharmaceutically acceptable carrier, wherein the pharmaceutically acceptable carrier is a liquid carrier.

40. The method of clause 39 wherein the liquid carrier is selected from the group consisting of saline, glucose, alcohols, glycols, esters, amides, and a combination thereof.

41. The method of any one of clauses 24 to 40 wherein the composition is administered in a single-dose or a multiple-dose regimen.

42. A pharmaceutical composition comprising a dosage form of a compound effective to decrease the expression a cytoplasmic granule toxin in the astrocytes of a patient with amyotrophic lateral sclerosis.

43. The composition of clause 42 wherein the compound is selected from the group consisting of a drug, a peptide, and a nucleic acid.

44. The composition of clause 43 wherein the compound is a nucleic acid.

45. The composition of clause 44 wherein the nucleic acid is selected from the group consisting of siRNA, an miRNA, and an shRNA.

46. The composition of clause 44 wherein the compound is an antisense RNA molecule.

47. The composition of clause 45 wherein the nucleic acid is an shRNA.

48. The composition of clause 44 wherein the nucleic acid has the sequence of SEQ ID NO: 1.

49. The composition of clause 44 wherein the nucleic acid has the sequence of SEQ ID NO: 2.

50. The composition of any one of clauses 42 to 49, wherein the composition further comprises one or more carriers, diluents, or excipients, or a combination thereof.

51. The composition of clause 50 wherein the composition comprises a pharmaceutically acceptable carrier, wherein the pharmaceutically acceptable carrier is a liquid carrier.

52. The composition of clause 51 wherein the liquid carrier is selected from the group consisting of saline, glucose, alcohols, glycols, esters, amides, and a combination thereof.

53. The composition of any one of clauses 42 to 52 wherein the purity of the compound is at least 98% based on weight percent.

54. The composition of any one of clauses 42 to 53 wherein the composition is in an ampoule or a sealed vial.

55. The composition of any one of clauses 42 to 50 or 53 to 54 in the form of a reconstitutable lyophilizate.

56. A pharmaceutical composition comprising a dosage form of a compound effective to increase the expression of MHC class I in the motor neurons of a patient with amyotrophic lateral sclerosis.

57. The composition of clause 56 wherein the compound is selected from the group consisting of a drug, a peptide, and a nucleic acid.

58. The composition of clause 56 wherein the compound is a nucleic acid.

59. The composition of clause 58 wherein the nucleic acid has the sequence of SEQ ID NO: 3.

60. The composition of any one of clauses 56 to 59 wherein the composition further comprises one or more carriers, diluents, or excipients, or a combination thereof.

61. The composition of clause 60 wherein the composition comprises a pharmaceutically acceptable carrier, wherein the pharmaceutically acceptable carrier is a liquid carrier.

62. The composition of clause 61 wherein the liquid carrier is selected from the group consisting of saline, glucose, alcohols, glycols, esters, amides, and a combination thereof.

63. The composition of any one of clauses 56 to 62 wherein the purity of the compound is at least 98% based on weight percent.

64. The composition of any one of clauses 56 to 63 wherein the composition is in an ampoule or a sealed vial.

65. The composition of any one of clauses 56 to 60 or 63 to 64 in the form of a reconstitutable lyophilizate.

66. The method or pharmaceutical composition of any one of clauses 1 to 65 wherein the composition is in a dosage form selected from the group consisting of an inhalation dosage form, an oral dosage form, and a parenteral dosage form.

67. The method or pharmaceutical composition of clause 66 wherein the parenteral dosage form is selected from the group consisting of an intradermal dosage form, a subcutaneous dosage form, an intramuscular dosage form, an intraperitoneal dosage form, an intravenous dosage form, and an intrathecal dosage form.

68. The composition of clause 55 or 65 in the form of a lyophilizate.

69. The composition of any one of clauses 42 to 50, 53 to 60, or 63 to 65 in the form of a solid.

70. A kit comprising a sterile vial, the composition of any one of clauses 56 to 69, and instructions for use describing use of the composition for treating a patient with amyotrophic lateral sclerosis.

71. The kit of clause 70 wherein the compound or composition is in the form of a reconstitutable lyophilizate.

72. The kit of clause 70 or 71 wherein the dose of the compound is in the range of 1 to 5 µg/kg of patient body weight.

73. The kit of any one of clauses 70 to 72 wherein the purity of the compound is at least 99% based on weight percent.

74. The kit of any one of clauses 70 to 73 wherein the compound or the composition is in a parenteral dosage form.

75. The kit of clause 74 wherein the parenteral dosage form is selected from the group consisting of an intradermal dosage form, a subcutaneous dosage form, an intramuscular dosage form, an intraperitoneal dosage form, an intravenous dosage form, and an intrathecal dosage form.

76. The kit of any one of clauses 70 to 75 wherein the composition further comprises a pharmaceutically acceptable carrier.

77. The kit of clause 76 wherein the pharmaceutically acceptable carrier is a liquid carrier selected from the group consisting of saline, glucose, alcohols, glycols, esters, amides, and a combination thereof.

78. Use of the composition of any one of clauses 42 to 69 for the manufacture of a medicament for treating amyotrophic lateral sclerosis.

79. The pharmaceutical composition of any one of clauses 42 to 69 for use in treating amyotrophic lateral sclerosis.

80. The method of any one of clauses 1 to 23 wherein the cytoplasmic granule toxin is not SOD1.

81. The method of any one of clauses 1 to 23 wherein the cytoplasmic granule toxin is not an antioxidant cytoplasmic granule toxin.

82. The composition of any one of clauses 42 to 55 wherein the cytoplasmic granule toxin is not SOD1.

83. The composition of any one of clauses 42 to 55 wherein the cytoplasmic granule toxin is not an antioxidant cytoplasmic granule toxin.

DETAILED DESCRIPTION OF ILLUSTRATIVE EMBODIMENTS

Figure 1A:
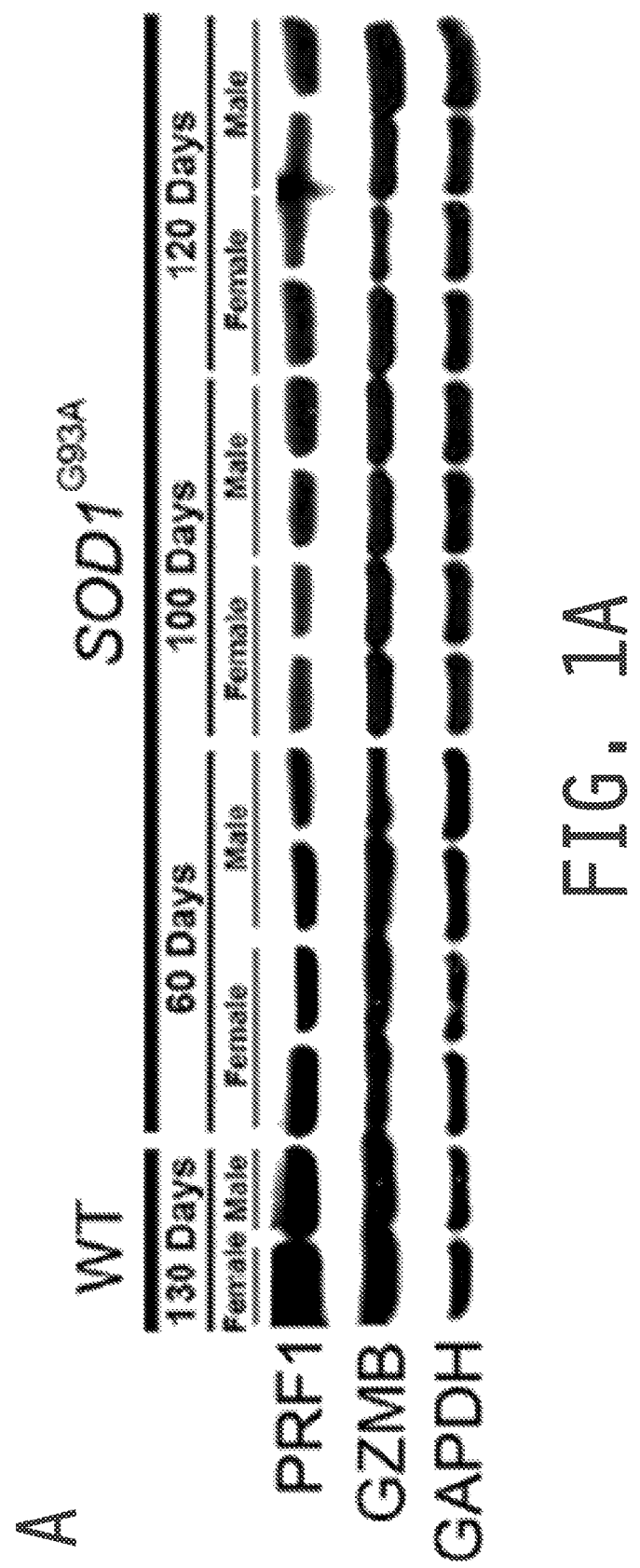
FIG. 1: (A) Western blot analysis reveals perforin (PRF1) and granzyme B (GZMB) expression in spinal cord of wild type and Sod1$^{G93A}$ mice. (B) Expression of both PRF1 and GZMB is observed in astrocytes but not in microglia. (C) Increased co-localization of PRF1 and GZMB in Sod1$^{G93A}$ astrocytes upon co-culture with MNs. Scale bars represent 5 µm. (D) Increased co-localization of PRF1 and GZMB in Sod1$^{G93A}$ astrocytes upon co-culture in spinal cords from Sod1$^{G93A}$ mice. Scale bars represent 200 µm. (E) Western blot analysis shows expression of both PRF1 and GZMB in post-mortem NPC derived astrocytes of human ALS patients and controls. (F) Co-localization of PRF1 and GZMB is only detected in spinal cords of ALS patients. Scale bars represent 200 µm. In this figure, PRF1 is shown in red, GZMB is shown in green, and GFAP is shown in blue. DAPI was used to visualize nuclei. (G) Expression of Prf1 and Gzmb RNA was found in the spinal cords of both wild-type and SOD1$^{G93A}$ mice. (H) Astrocytes, both primary and NPC derived, expressed Prf1 and Gzmb RNA, whereas microglia only expressed Gzmb. (I) Immunostaining for PRF1 and GZMB of splenocytes revealed robust and specific signal for both cytolytic proteins. Gray represents nuclear DAPI staining. (J) Sequential staining protocol for PRF1 and GZMB used as in (I). Blue represents astrocytic marker, GFAP. Scale bars represents 5 µm.

Several embodiments of the invention are described by the following enumerated clauses and each of the embodiments described in this Detailed Description section of the application applies to each of the following embodiments:

1. A method for treating a patient with amyotrophic lateral sclerosis by decreasing the expression of a cytoplasmic granule toxin in astrocytes of the patient, the method comprising the step of
  administering to the patient a composition comprising an effective amount of a compound that decreases the expression the cytoplasmic granule toxin in the astrocytes of the patient.

2. The method of clause 1 wherein the cytoplasmic granule toxin is a perforin.

3. The method of clause 2 wherein the perforin is perforin 1.

4. The method of clause 1 wherein the cytoplasmic granule toxin is a granzyme.

5. The method of clause 4 wherein the granzyme is granzyme B.

6. The method of any one of clauses 1 to 5 wherein the decreased expression of the cytoplasmic granule toxin results in an effect on motor neurons in the patient selected from the group consisting of an increase in the number of motor neurons, a decrease in soma atrophy, and an increase in neurite length after administration of the compound.

7. The method of any one of clauses 1 to 6 wherein the compound is selected from the group consisting of a drug, a peptide, and a nucleic acid.

8. The method of clause 7 wherein the compound is a nucleic acid.

9. The method of clause 8 wherein the nucleic acid functions by RNA interference or is an antisense RNA molecule.

10. The method of clause 8 wherein the nucleic acid is selected from the group consisting of an siRNA, an miRNA, and an shRNA.

11. The method of clause 10 wherein the nucleic acid is an shRNA.

12. The method of clause 8 wherein the nucleic acid is delivered to the patient in a bacterial vector or in a viral vector.

13. The method of clause 8 wherein the nucleic acid has the sequence of SEQ ID NO: 1.

14. The method of clause 8 wherein the nucleic acid has the sequence of SEQ ID NO: 2.

15. The method of any one of clauses 1 to 14 wherein the amyotrophic lateral sclerosis is sporadic amyotrophic lateral sclerosis.

16. The method of any one of clauses 1 to 14 wherein the amyotrophic lateral sclerosis is familial amyotrophic lateral sclerosis.

17. The method of any one of clauses 1 to 16 wherein the amount of the compound is in the range of about 1 ng/kg of patient body weight to about 1 mg/kg of patient body weight.

18. The method of any one of clauses 1 to 17 wherein the amount of the compound is in the range of about 1 ng/kg of patient body weight to about 500 ng/kg of patient body weight.

19. The method of any one of clauses 1 to 18 wherein the amount of the compound is in the range of about 1 ng/kg of patient body weight to about 100 ng/kg of patient body weight.

20. The method of any one of clauses 1 to 19 wherein the composition further comprises a carrier, an excipient, or a diluent, or a combination thereof.

21. The method of clause 20 wherein the composition comprises a pharmaceutically acceptable carrier, wherein the pharmaceutically acceptable carrier is a liquid carrier.

22. The method of clause 21 wherein the liquid carrier is selected from the group consisting of saline, glucose, alcohols, glycols, esters, amides, and a combination thereof.

23. The method of any one of clauses 1 to 22 wherein the composition is administered in a single-dose or a multiple-dose regimen.

24. A method for treating amyotrophic lateral sclerosis by increasing MHC class I expression in motor neurons of a patient, the method comprising the step of
  administering to the patient a composition comprising an effective amount of a compound that increases the expression of MHC class I in the motor neurons of the patient.

25. The method of clause 24 wherein the increased expression of the MHC class I results in an effect on motor neurons in the patient selected from the group consisting of an increase in the number of motor neurons, a decrease in soma atrophy, and an increase in neurite length after administration of the compound.

26. The method of any one of clauses 24 to 25 wherein the compound is selected from the group consisting of a drug, a peptide, and a nucleic acid.

27. The method of clause 26 wherein the compound is a nucleic acid.

28. The method of clause 27 wherein the nucleic acid is delivered to the patient in a bacterial vector or in a viral vector.

29. The method of clause 28 wherein the vector is a viral vector.

30. The method of clause 29 wherein the vector is selected from the group consisting of a lentiviral vector and an adenovirus vector.

31. The method of clause 30 wherein the nucleic acid has the sequence of SEQ ID NO: 3.

32. The method of clause 31 wherein the nucleic acid encodes the histocompatibility complex H2K.

33. The method of any one of clauses 24 to 32 wherein the amyotrophic lateral sclerosis is sporadic amyotrophic lateral sclerosis.

34. The method of any one of clauses 24 to 32 wherein the amyotrophic lateral sclerosis is familial amyotrophic lateral sclerosis.

35. The method of any one of clauses 24 to 34 wherein the amount of the compound is in the range of about 1 ng/kg of patient body weight to about 1 mg/kg of patient body weight.

36. The method of any one of clauses 24 to 35 wherein the amount of the compound is in the range of about 1 ng/kg of patient body weight to about 500 ng/kg of patient body weight.

37. The method of any one of clauses 24 to 36 wherein the amount of the compound is in the range of about 1 ng/kg of patient body weight to about 100 ng/kg of patient body weight.

38. The method of any one of clauses 24 to 37 wherein the composition further comprises a carrier, an excipient, or a diluent, or a combination thereof.

39. The method of clause 38 wherein the composition comprises a pharmaceutically acceptable carrier, wherein the pharmaceutically acceptable carrier is a liquid carrier.

40. The method of clause 39 wherein the liquid carrier is selected from the group consisting of saline, glucose, alcohols, glycols, esters, amides, and a combination thereof.

41. The method of any one of clauses 24 to 40 wherein the composition is administered in a single-dose or a multiple-dose regimen.

42. A pharmaceutical composition comprising a dosage form of a compound effective to decrease the expression a cytoplasmic granule toxin in the astrocytes of a patient with amyotrophic lateral sclerosis.

43. The composition of clause 42 wherein the compound is selected from the group consisting of a drug, a peptide, and a nucleic acid.

44. The composition of clause 43 wherein the compound is a nucleic acid.

45. The composition of clause 44 wherein the nucleic acid is selected from the group consisting of siRNA, an miRNA, and an shRNA.

46. The composition of clause 44 wherein the compound is an antisense RNA molecule.

47. The composition of clause 45 wherein the nucleic acid is an shRNA.

48. The composition of clause 44 wherein the nucleic acid has the sequence of SEQ ID NO: 1.

49. The composition of clause 44 wherein the nucleic acid has the sequence of SEQ ID NO: 2.

50. The composition of any one of clauses 42 to 49, wherein the composition further comprises one or more carriers, diluents, or excipients, or a combination thereof.

51. The composition of clause 50 wherein the composition comprises a pharmaceutically acceptable carrier, wherein the pharmaceutically acceptable carrier is a liquid carrier.

52. The composition of clause 51 wherein the liquid carrier is selected from the group consisting of saline, glucose, alcohols, glycols, esters, amides, and a combination thereof.

53. The composition of any one of clauses 42 to 52 wherein the purity of the compound is at least 98% based on weight percent.

54. The composition of any one of clauses 42 to 53 wherein the composition is in an ampoule or a sealed vial.

55. The composition of any one of clauses 42 to 50 or 53 to 54 in the form of a reconstitutable lyophilizate.

56. A pharmaceutical composition comprising a dosage form of a compound effective to increase the expression of MHC class I in the motor neurons of a patient with amyotrophic lateral sclerosis.

57. The composition of clause 56 wherein the compound is selected from the group consisting of a drug, a peptide, and a nucleic acid.

58. The composition of clause 56 wherein the compound is a nucleic acid.

59. The composition of clause 58 wherein the nucleic acid has the sequence of SEQ ID NO: 3.

60. The composition of any one of clauses 56 to 59 wherein the composition further comprises one or more carriers, diluents, or excipients, or a combination thereof.

61. The composition of clause 60 wherein the composition comprises a pharmaceutically acceptable carrier, wherein the pharmaceutically acceptable carrier is a liquid carrier.

62. The composition of clause 61 wherein the liquid carrier is selected from the group consisting of saline, glucose, alcohols, glycols, esters, amides, and a combination thereof.

63. The composition of any one of clauses 56 to 62 wherein the purity of the compound is at least 98% based on weight percent.

64. The composition of any one of clauses 56 to 63 wherein the composition is in an ampoule or a sealed vial.

65. The composition of any one of clauses 56 to 60 or 63 to 64 in the form of a reconstitutable lyophilizate.

66. The method or pharmaceutical composition of any one of clauses 1 to 65 wherein the composition is in a dosage form selected from the group consisting of an inhalation dosage form, an oral dosage form, and a parenteral dosage form.

67. The method or pharmaceutical composition of clause 66 wherein the parenteral dosage form is selected from the group consisting of an intradermal dosage form, a subcutaneous dosage form, an intramuscular dosage form, an intraperitoneal dosage form, an intravenous dosage form, and an intrathecal dosage form.

68. The composition of clause 55 or 65 in the form of a lyophilizate.

69. The composition of any one of clauses 42 to 50, 53 to 60, or 63 to 65 in the form of a solid.

70. A kit comprising a sterile vial, the composition of any one of clauses 56 to 69, and instructions for use describing use of the composition for treating a patient with amyotrophic lateral sclerosis.

71. The kit of clause 70 wherein the compound or composition is in the form of a reconstitutable lyophilizate.

72. The kit of clause 70 or 71 wherein the dose of the compound is in the range of 1 to 5 µg/kg of patient body weight.

73. The kit of any one of clauses 70 to 72 wherein the purity of the compound is at least 99% based on weight percent.

74. The kit of any one of clauses 70 to 73 wherein the compound or the composition is in a parenteral dosage form.

75. The kit of clause 74 wherein the parenteral dosage form is selected from the group consisting of an intradermal dosage form, a subcutaneous dosage form, an intramuscular dosage form, an intraperitoneal dosage form, an intravenous dosage form, and an intrathecal dosage form.

76. The kit of any one of clauses 70 to 75 wherein the composition further comprises a pharmaceutically acceptable carrier.

77. The kit of clause 76 wherein the pharmaceutically acceptable carrier is a liquid carrier selected from the group consisting of saline, glucose, alcohols, glycols, esters, amides, and a combination thereof.

78. Use of the composition of any one of clauses 42 to 69 for the manufacture of a medicament for treating amyotrophic lateral sclerosis.

79. The pharmaceutical composition of any one of clauses 42 to 69 for use in treating amyotrophic lateral sclerosis.

In any of the various embodiments described herein, the following features may be present where applicable, providing additional embodiments of the invention. For all of the embodiments, any applicable combination of embodiments is also contemplated. Any applicable combination of the above-described embodiments in the enumerated clauses is also considered to be in accordance with the invention.

In one embodiment there is provided a method for treating a patient with amyotrophic lateral sclerosis by decreasing the expression of a cytoplasmic granule toxin in astrocytes of the patient. The method comprises the step of administering to the patient a composition comprising an effective amount of a compound that decreases the expression of the cytoplasmic granule toxin in the astrocytes of the patient. In one illustrative embodiment, the cytoplasmic granule toxin is not SOD1. In another illustrative embodiment, the cytoplasmic granule toxin is a non-antioxidant cytoplasmic granule toxin.

In another embodiment, a method for treating amyotrophic lateral sclerosis by increasing MHC class I expression in motor neurons of a patient is provided. The method comprises the step of administering to the patient a composition comprising an effective amount of a compound that increases the expression of MHC class I in the motor neurons of the patient. In any of these method embodiments, or any corresponding use, the decreased expression of the cytoplasmic granule toxin in astrocytes of the patient, or the increased expression of MHC class I in motor neurons of the patient, results in an effect on motor neurons of the patient selected from, but not limited to, the group consisting of an increase in the number of motor neurons, a decrease in soma atrophy, and an increase in neurite length after administration of the compound. In various embodiments, the motor neurons may be in the motor cortex, brain stem, or spinal cord of the patient, or combinations thereof.

In another illustrative aspect, a pharmaceutical composition is provided, comprising a dosage form of a compound effective to decrease the expression of a cytoplasmic granule toxin in the astrocytes of a patient with amyotrophic lateral sclerosis. In still another illustrative embodiment, a pharmaceutical composition is provided, comprising a dosage form of a compound effective to increase the expression of MHC class I in the motor neurons of a patient with amyotrophic lateral sclerosis. Kits comprising these pharmaceutical compositions are also provided. In other aspects, uses of these pharmaceutical compositions for the manufacture of a medicament for treating amyotrophic lateral sclerosis are provided. In yet other embodiments, these pharmaceutical compositions are provided, for use in treating amyotrophic lateral sclerosis.

The methods, kits, uses, and pharmaceutical compositions described herein can be used to treat either sporadic or familial amyotrophic lateral sclerosis, and can be used for both human clinical medicine and veterinary medicine. In one embodiment, the compounds described herein that can be used to treat sporadic or familial amyotrophic lateral sclerosis are compounds that are effective to decrease the expression, or reduce the activity, of a cytoplasmic granule toxin in the astrocytes of a patient with amyotrophic lateral sclerosis. In another embodiment, the compounds described herein that can be used to treat sporadic or familial amyotrophic lateral sclerosis, are compounds that are effective to increase the expression of MHC class I in the motor neurons of a patient with amyotrophic lateral sclerosis. The compounds are selected from the group consisting of drugs, peptides, and nucleic acids, or combinations thereof.

A cytoplasmic granule toxin that is targeted can be any astrocyte cytoplasmic granule toxin that is toxic to motor neurons, including but not limited to, perforins (e.g., perforin 1) and granzymes (e.g., granzyme B). In one embodiment, the granzyme is not granzyme A. Expression or activity of perforins and granzymes can be reduced, for example, by treatment of a patient with a drug, peptide, or nucleic acid, or a combination thereof, that reduces the expression or the activity of a cytoplasmic granule toxin in the astrocytes of a patient with amyotrophic lateral sclerosis. For example, compounds that reduce activity of a cytoplasmic granule toxin, such as perforin, include Ca2+-complexing agents. In another embodiment, expression a cytoplasmic granule toxin in the astrocytes of a patient with amyotrophic lateral sclerosis can be reduced by treatment of the patient with a pharmaceutical composition comprising a nucleic acid such as an antisense RNA molecule, an siRNA, an shRNA, or an miRNA that inhibits expression of a cytoplasmic granule toxin, such as a perforin or a granzyme. Inhibitors of perforin expression or activity also include concanamycin A (vacuolar type H(+)-ATPase (V-ATPase) inhibitors), bafilomycin A1(vacuolar type H(+)-ATPase (V-ATPase) inhibitors), destruxin E (vacuolar type H(+)-ATPase (V-ATPase) inhibitors), prodigiosin 25-C (vacuolar type H(+)-ATPase (V-ATPase) inhibitors. cytochalasin D (an inhibitor of actin polymerization), antimycin A and oligomycin A (respiratory inhibitors), calphostin C (protein kinase inhibitor), herbimycin A (protein kinase inhibitor), K252a (protein kinase inhibitor), staurosporine (protein kinase inhibitor). Dihydrofuro[3,4-c]pyridinones, 1-amino-2,4-dicyanopyrido[1,2-a]benzimidazoles, isobenzofuran-1(3H)-ones (small-molecule inhibitors of perforin-induced lysis). Apolipoprotein B (perforin inhibitor protein in human serum), Suramin, and glycosaminoglycans (abolishes binding of LDL to its receptor to inhibit the lytic activities of perforin). Inhibitors of granzyme B expression also include Granzyme B Inhibitor I (Z-AAD-CMK, C19H24C1N3O7, A weak inhibitor of the human and murine granzyme B), Granzyme B Inhibitor II (Ac-IETD-CHO (SEQ ID NO: 4), C21H34N4O10, A potent, reversible inhibitor of granzyme B and caspase-8), Granzyme B Inhibitor II Cell permeable (Ac-AAVALLPAVLLALLAP-IETD-CHO (SEQ ID NO: 5), C95H162N20O26, A potent, cell-permeable, and reversible inhibitor of caspase-8 and Granzyme B), Granzyme B Inhibitor III (Z-IE(OMe)TD(OMe)-FMK (SEQ ID NO: 6), C30H43FN4O11, A potent, cell-permeable, and irreversible inhibitor of caspase-8 and granzyme B), Granzyme B Inhibitor IV (Ac-IEPD-CHO (SEQ ID NO: 7), C22H34N4O9, A reversible inhibitor of granzyme B and caspase-8), Granzyme B inhibitor (Ac-ESMD-CHO (SEQ ID NO: 8), C19H30N4O10S, Reversible Inhibitor of granzyme B and caspase-8), Human proteinase inhibitor 9 (PI-9)(8- 10), and Serine protease inhibitor 6 (Sip6).

Suitable methods for delivery of antisense RNA molecules, siRNAs, shRNAs, or miRNAs to a patient include bacterial or viral vectors, such as lentiviral vectors or adenovirus vectors. Exemplary of such RNA molecules are the nucleic acids with SEQ ID NO: 1 and SEQ ID NO: 2 shown by the present inventors to efficiently ablate expression of perforin 1 or granzyme B, respectively, in SOD1$^{G93A}$ astrocytes or in astrocytes derived from familial or sporadic amyotrophic lateral sclerosis patients, resulting in effective suppression of motor neuron toxicity in motor neurons exposed to the astrocytes (see Example 4).

In another embodiment, the compounds described herein that can be used to treat amyotrophic lateral sclerosis, are compounds that are effective to increase the expression of MHC class I in the motor neurons of a patient with amyotrophic lateral sclerosis. The compounds are selected from the group consisting of drugs, peptides, and nucleic acids, or combinations thereof. In an illustrative embodiment, the nucleic acid with SEQ ID NO: 3, encoding the histocompatibility complex H2K, shown herein to cause sustained expression of MHC class I in motor neurons, protecting motor neurons from the toxic effects of SOD1$^{G93A}$ astrocytes (see Example 6), can be used to treat amyotrophic lateral sclerosis.

In accordance with these embodiments, pharmaceutical compositions are provided comprising a purified nucleic acid comprising, or consisting of, a sequence of SEQ ID NO: 1, SEQ ID NO: 2, or SEQ ID NO: 3 (see Table 1). A purified nucleic acid is also provided comprising a complement of SEQ ID NO: 1, SEQ ID NO: 2, or SEQ ID NO: 3, or a sequence that hybridizes under highly stringent conditions to a complement of a sequence consisting of SEQ ID NO: 1, SEQ ID NO: 2, or SEQ ID NO: 3. In accordance with the invention "highly stringent conditions" means hybridization at 65° C. in 5X SSPE and 50% formamide, and washing at 65° C. in 0.5X SSPE. Conditions for high, low, and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

TABLE 1

SEQ ID NO: 1 ACCTGAATCATGGCCACCTAA

SEQ ID NO: 2 CATTGTCTCCTATGGACGAAA

SEQ ID NO: 3 Sequence in Example 25 between and including the underlined ATG and the underlined TGA The invention encompasses isolated or substantially purified nucleic acids. An "isolated" or "purified" nucleic acid molecule is substantially free of chemical precursors or other chemicals when chemically synthesized, or is substantially free of cellular material if made by recombinant DNA techniques. In various embodiments described herein, the nucleic acids for use in the methods, compositions, and kits described herein may be double-stranded (e.g., antisense RNAs) or single-stranded, but the nucleic acids are typically single-stranded.

The nucleic acids for use in the methods, uses, pharmaceutical compositions, and kits described herein can be modified by substitution, deletion, truncation, and/or can be fused with other nucleic acid molecules wherein the resulting nucleic acids hybridize specifically under highly stringent conditions to the complements of nucleic acids of SEQ ID NO: 1, SEQ ID NO: 2, or SEQ ID NO: 3, and wherein the modified nucleic acids are useful in the methods or uses described herein. Derivatives can also be made such as phosphorothioate, phosphotriester, phosphoramidate, and methylphosphonate derivatives (Goodchild, et al., Proc. Natl. Acad. Sci. 83:4143-4146 (1986), incorporated herein by reference).

In another embodiment, nucleic acid molecules are provided having about 60%, about 70%, about 75%, about 80%, about 85%, about 90%, about 95%, about 96%, about 97%, about 98%, or about 99% homology to SEQ ID NO: 1, SEQ ID NO: 2, or SEQ ID NO: 3. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

Techniques for synthesizing the nucleic acids described herein, such as nucleic acids of SEQ ID NO: 1, SEQ ID NO: 2, or SEQ ID NO: 3, or fragments thereof, are well-known in the art and include chemical syntheses. Such techniques are described in Sambrook et al., "Molecular Cloning: A Laboratory Manual", 3rd Edition, Cold Spring Harbor Laboratory Press, (2001), incorporated herein by reference. Nucleic acids for use in the methods described herein can be made commercially. Techniques for purifying or isolating the nucleic acids described herein are well-known in the art. Such techniques are described in Sambrook et al., "Molecular Cloning: A Laboratory Manual", 3rd Edition, Cold Spring Harbor Laboratory Press, (2001), incorporated herein by reference.

In one embodiment, the compounds described herein for ablating expression of perforins or granzymes in astrocytes or inducing expression of MHC class I in motor neurons (i.e., drugs, peptides, or nucleic acids) may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of the compound, or additional therapeutic agents to be administered with the compound, and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In one embodiment, a pharmaceutically acceptable carrier may be selected from any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions, and sterile powders for the preparation of sterile injectable solutions or dispersions. Supplementary active compounds can also be incorporated into the pharmaceutical compositions of the invention.

In various embodiments, liquid formulations may include suspensions and solutions. Such formulations may comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, such as a lyophilizate. Thus, in one embodiment, the lyophilizate can be a reconstitutable lyophilizate.

In one illustrative aspect, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents. In other embodiments, isotonic agents, for example, sugars, polyalcohols such as mannitol, sorbitol, or sodium chloride can be included in the pharmaceutical composition.

In one embodiment the excipient comprises a buffer. In one embodiment, the pH of the buffer is about 5.0 to about 8.0. The buffer may be any acceptable buffer for the indicated pH range and physiological compatibility. In addition a buffer may additionally act as a stabilizer. In one embodiment, the buffer comprises an ascorbate, sorbate, formate, lactate, fumarate, tartrate, glutamate, acetate, citrate, gluconate, histidine, malate, phosphate or succinate buffer.

In one aspect, a compound (i.e., a drug, a peptide, or a nucleic acid), or additional therapeutic agent as described herein, may be administered directly into the blood stream, into muscle, or into an internal organ. Suitable routes for parenteral administration include intravenous, intraarterial, intraperitoneal, intrathecal, epidural, intracerebroventricular, intrasternal, intracranial, intramuscular, and subcutaneous delivery. Suitable means for parenteral administration include needle (including microneedle) injectors, needle-free injectors and infusion techniques. Examples of parenteral dosage forms include aqueous solutions of the active agent, in an isotonic saline, glucose (e.g., 5% glucose solutions), or other well-known pharmaceutically acceptable liquid carriers such as liquid alcohols, glycols, esters, and amides. Prolonged absorption of the injectable compositions can be brought about by including in the composition an agent which delays absorption, for example, monostearate salts and gelatin.

Also contemplated herein are kits comprising the pharmaceutical composition described herein. In another embodiment, a kit comprising a sterile vial, the pharmaceutical composition of any one of the preceding embodiments, and instructions for use describing use of the composition for treating a patient with amyotrophic lateral sclerosis is described.

In another embodiment, the kit of the preceding embodiment wherein the compound or the composition is in the form of a reconstitutable lyophlizate is described.

In another embodiment, any of the preceding kit embodiments wherein the dose of the compound in the pharmaceutical composition is in the range of 1 to 5 µg/kg is described.

In another embodiment, any of the preceding kit embodiments wherein the dose of the compound in the pharmaceutical composition is in the range of 1 to 3 µg/kg is described.

In another embodiment, the kit of any of the preceding kit embodiments is described wherein the purity of the compound is at least 90% based on weight percent. In another embodiment, the kit of any of the preceding embodiments is described wherein the purity of the compound is at least 95% based on weight percent. In another embodiment, the kit of any of the preceding kit embodiments is described wherein the purity of the compound is at least 98% based on weight percent. In another embodiment, the kit of any of the preceding kit embodiments is described wherein the purity of the compound is at least 99% based on weight percent.

In another illustrative aspect, the kit of any of the preceding kit embodiments is described wherein the compound or the composition is in a parenteral dosage form. The parenteral dosage form can be selected from the group consisting of an intradermal dosage form, a subcutaneous dosage form, an intramuscular dosage form, an intraperitoneal dosage form, an intravenous dosage form, and an intrathecal dosage form. In yet another embodiment, the kit can comprise the composition and the composition can further comprise a pharmaceutically acceptable carrier. The pharmaceutically acceptable carrier can be a liquid carrier selected from the group consisting of saline, glucose, alcohols, glycols, esters, amides, and a combination thereof.

Any effective regimen for administering the compound can be used. For example, the compound can be administered as a single dose, or can be divided and administered as a multiple-dose daily regimen. Further, a staggered regimen, for example, one to five days per week can be used as an alternative to daily treatment, and for the purpose of the pharmaceutical compositions, kits, methods, and uses described herein, such intermittent or staggered daily regimen is considered to be equivalent to every day treatment and is contemplated. In one illustrative embodiment the patient is treated with multiple injections of the compound to eliminate the disease state (i.e., amyotrophic lateral sclerosis) or to reduce or stabilize the symptoms of disease. In one embodiment, the patient is injected multiple times (preferably about 2 up to about 50 times), for example, at 12-72 hour intervals or at 48-72 hour intervals. Additional injections of the compound can be administered to the patient at an interval of days or months after the initial injections(s), and the additional injections can prevent recurrence of the disease or can prevent an increase in the severity of the symptoms of disease.

The unitary daily dosage of the compound can vary significantly depending on the patient condition, the disease state being treated, the purity of the compound and its route of administration and tissue distribution, and the possibility of co-usage of other therapeutic treatments. The effective amount to be administered to a patient is based on body surface area, mass, and physician assessment of patient condition. Effective doses can range, for example, from about 1 ng/kg to about 1 mg/kg, from about 1 µg/kg to about 500 µg/kg, and from about 1 µg/kg to about 100 µg/kg. These doses are based on an average patient weight of about 70 kg, and the kg are kg of patient body weight (mass). In one embodiment, the compound or pharmaceutical composition is in a multidose form. In another embodiment, the compound or pharmaceutical composition is a single dose form (i.e., a unit dose form or a dosage unit).

In one embodiment, the compound can be administered in a dose of from about 1.0 ng/kg to about 1000 µg/kg, from about 10 ng/kg to about 1000 µg/kg, from about 50 ng/kg to about 1000 µg/kg, from about 100 ng/kg to about 1000 µg/kg, from about 500 ng/kg to about 1000 µg/kg, from about 1 ng/kg to about 500 µg/kg, from about 1 ng/kg to about 100 µg/kg, from about 1 µg/kg to about 50 µg/kg, from about 1 µg/kg to about 10 µg/kg, from about 5 µg/kg to about 500 µg/kg, from about 10 µg/kg to about 100 µg/kg, from about 20 µg/kg to about 200 µg/kg, from about 10 µg/kg to about 500 µg/kg, or from about 50 µg/kg to about 500 µg/kg. The total dose may be administered in single or divided doses and may, at the physician's discretion, fall outside of the typical range given herein. These dosages are based on an average patient weight of about 70 kg and the "kg" are kilograms of patient body weight. The physician will readily be able to determine doses for subjects whose weight falls outside this range, such as infants and the elderly.

In another embodiment, the compound can be administered at a dose of from about 1 µg/m$^2$ to about 500 mg/m$^2$, from about 1 µg/m$^2$ to about 300 mg/m$^2$, or from about 100 µg/m$^2$ to about 200 mg/m$^2$. In other embodiments, the compound can be administered at a dose Of from about 1 mg/m$^2$, from about 1 mg/m$^2$ to about 300 mg/m$^2$, from about 1 mg/m$^2$ to about 200 mg/m$^2$, from about 1 mg/m$^2$ to about 100 mg/m$^2$, from about 1 mg/m$^2$ to about 50 mg/m$^2$, or from about 1 mg/m$^2$ to about 600 mg/m$^2$. The total dose may be administered in single or divided doses and may, at the physician's discretion, fall outside of the typical range given herein. These dosages are based on m$^2$ of body surface area.

In another embodiment, the pharmaceutical compositions and/or dosage forms of the compound for administration are prepared from compounds with a purity of at least about 90%, or about 95%, or about 96%, or about 97%, or about 98%, or about 99%, or about 99.5%. In another embodiment, pharmaceutical compositions and or dosage forms of the compound for administration are prepared from compounds with a purity of at least 90%, or 95%, or 96%, or 97%, or 98%, or 99%, or 99.5%. The purity of the compound may be measured using any conventional technique, including various chromatography or spectroscopic techniques, such as high pressure or high performance liquid chromatography, nuclear magnetic resonance spectroscopy, TLC, UV absorbance spectroscopy, fluorescence spectroscopy, and the like.

As used herein, purity determinations may be based on weight percentage, mole percentage, and the like. In addition, purity determinations may be based on the absence or substantial absence of certain predetermined components. It is also to be understood that purity determinations are applicable to solutions of the compounds and pharmaceutical compositions prepared by the methods described herein. In those instances, purity measurements, including weight percentage and mole percentage measurements, are related to the components of the solution exclusive of the solvent. In another embodiment, the compound or the pharmaceutical composition is provided in a sterile container (e.g., a vial) or package, for example, an ampoule or a sealed vial.

In another embodiment, the methods, pharmaceutical compositions, uses, and kits, described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Example 1

ALS Astrocytes Express and Show Increased Co-Localization of the Cytoplasmic Granule Toxins Perforin and Granzyme Cytoplasmic granule toxins of the granule exocytosis pathway comprise perforin (e.g., PRF1), a membrane-disrupting protein, and granzymes, a family of structurally related serine proteases with cytotoxic activity, of which granzyme B (GZMB) is an example and has been identified as potent pro-apoptotic factor. The present example analyzed if cytolytic compounds of the granule cell death pathway are expressed in cells of the spinal cord. As shown in FIG. 1A, both PRF1 and GZMB protein were readily detected in spinal cords of wild type and SOD1$^{G93A}$ mice (an accepted animal model for amyotrophic lateral sclerosis (ALS)) by Western blot analysis, and the presence of transcripts was confirmed by RT-PCR. Global expression levels of PRF1 or GZMB did not change with disease progression in SOD1$^{G93A}$ mice (FIG. 1A).

Figure 1B:
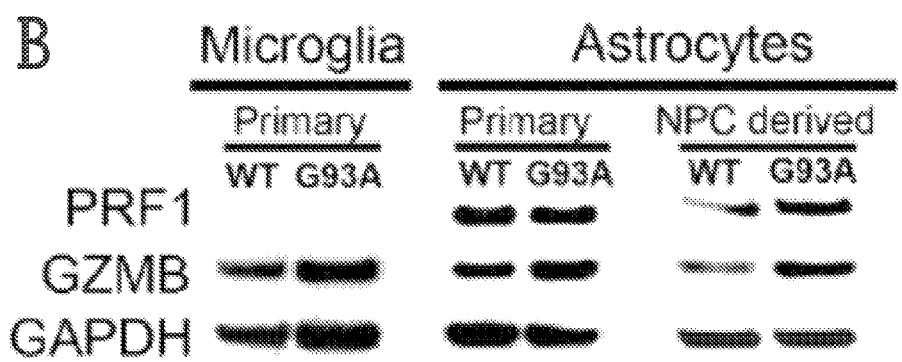
Figure 1C:
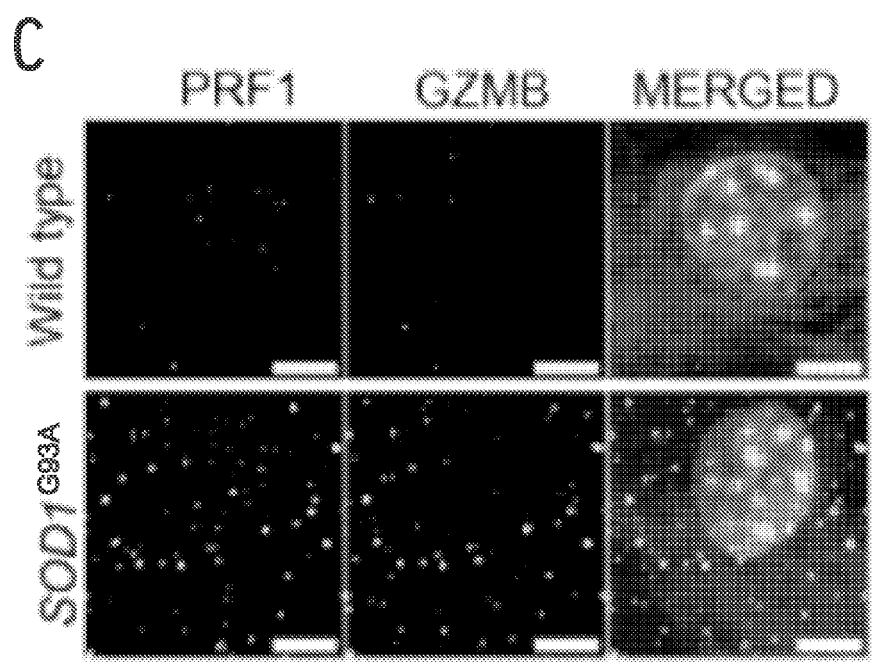

As both astrocytes and microglia exhibit cytotoxicity towards motor neurons (MNs), the cell-type specific expression of GZMB and PRF1 was determined. Microglia expressed GZMB but lacked PRF1. However, co-expression of both proteins was detected in astrocytes, and RT-PCR analyses confirmed these findings on the transcript level (see FIG. 1B). RNA analysis revealed expression of both Prf1 and Gzmb in astrocytes, but lack of Prf1 in microglia. Expression of Prf1 and Gzmb was found in the spinal cords of both wild-type and SOD1$^{G93A}$ mice (see FIG. 1G). Astrocytes, both primary and NPC derived, expressed Prf1 and Gzmb, whereas microglia only expressed Gzmb (see FIG. 1H). Surprisingly, PRF1 and GZMB co-localized in the cytoplasm of SOD1$^{G93A}$ astrocytes but not in wild type astrocytes (see FIG. 1C). Cytoplasmic co-localization of PRF1 and GZMB indicates storage of both cytolytic factors in intracellular vesicles, suggesting a prerequisite for an active granule exocytosis pathway that relies on synergistic action of both factors upon granule release.

Figure 1D:
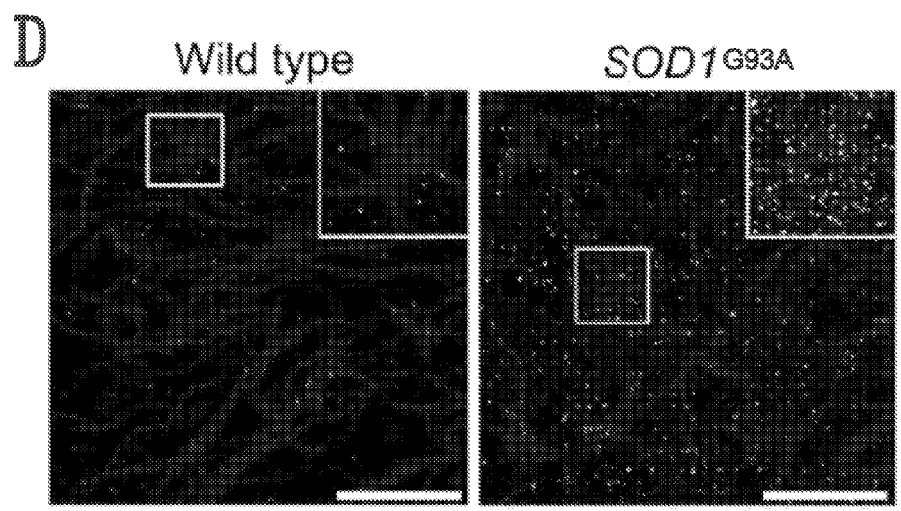
Figure 1E:
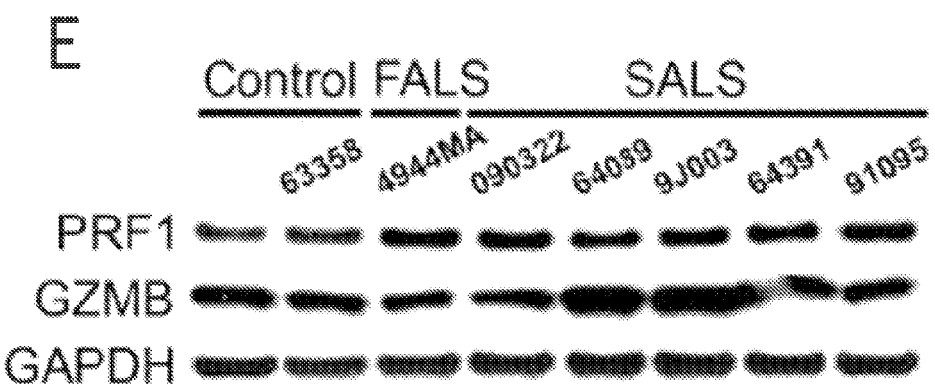
Figure 1F:
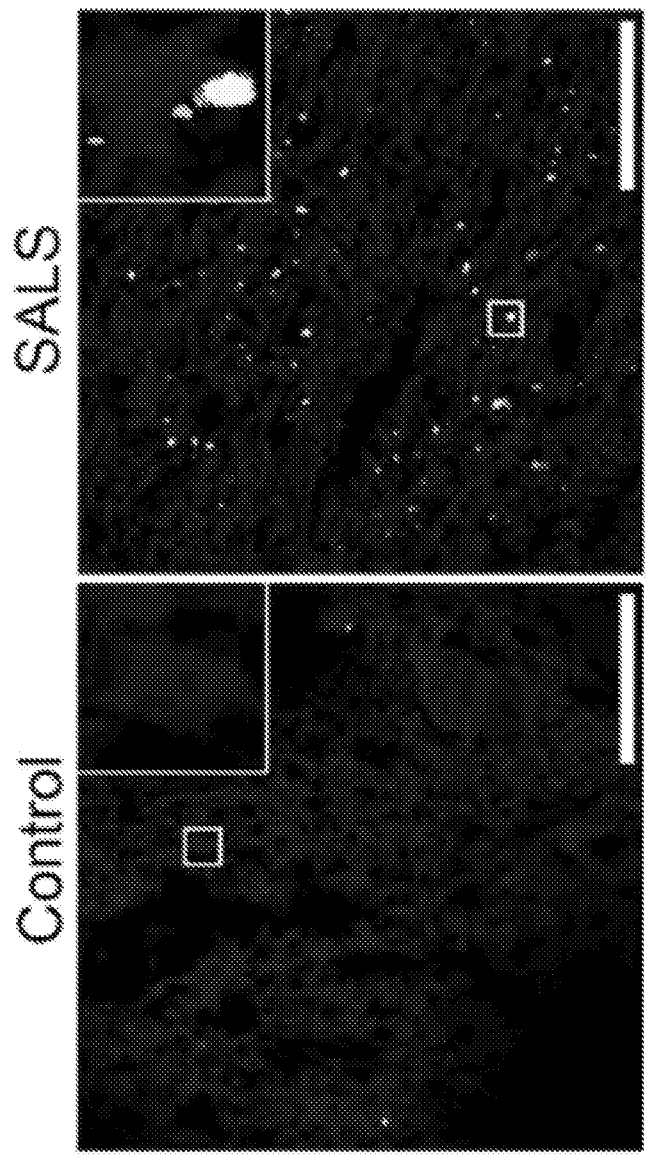
Figure 1I:
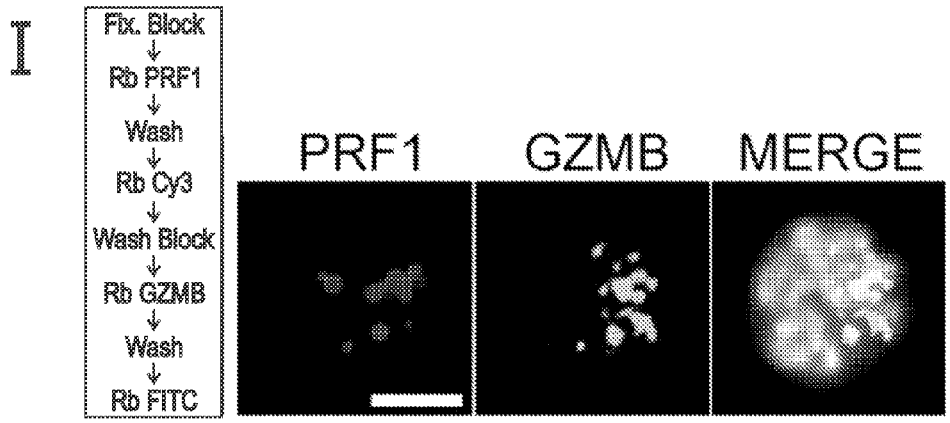
Figure 1J:
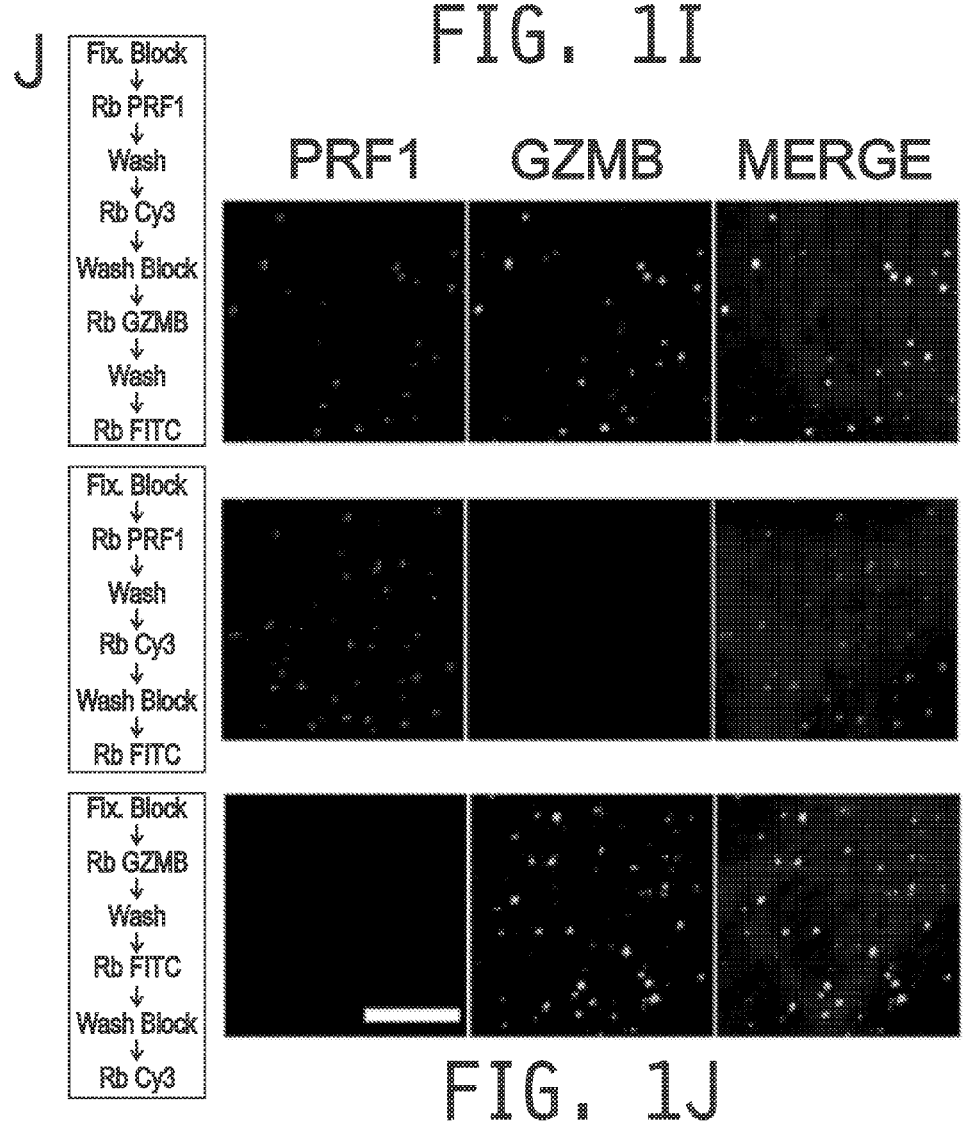

Increased levels of PRF1 and GZMB were also observed in vivo in astrocytes located in the spinal cord of SOD1$^{G93A}$ mice, with substantial co-localization of these two proteins (see FIG. 1D). Immunostaining for PRF1 and GZMB of splenocytes revealed robust and specific signal for both cytolytic proteins (see FIG. 1I). A sequential staining protocol for PRF1 and GZMB allowed the detection of these two cytolytic proteins in SOD1$^{G93A}$ astrocytes (see FIG. 1J). Since both antibodies, PRF1 and GZMB, were raised in rabbit, sequential staining allowed these two antibodies to be combined and to be detected specifically. Importantly, human post-mortem NPC derived astrocytes from controls and ALS patients exhibited expression of PRF1 and GZMB (see FIG. 1E), including ALS patient-derived astrocytes with known capacity to convey toxicity to MNs. Similar to astrocytes from SOD1$^{G93A}$ mice, astrocytes in the spinal cords of ALS patients contained PRF1 and GZMB in patterns consistent with cytoplasmic granules, while both proteins were virtually absent in unaffected controls (see FIG. 1F). In summary, this example demonstrates that murine and human astrocytes contain the cytolytic proteins PRF1 and GZMB in a subcellular localization pattern consistent with an active granule cell death pathway.

Figure 14A:
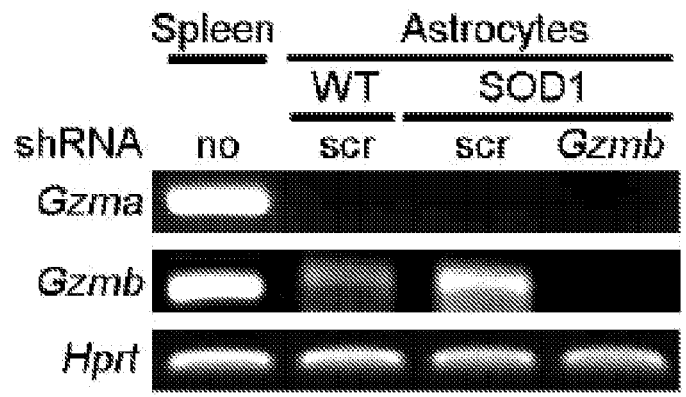
FIG. 14: (A-B) SOD1 astrocytes express high levels of Gzmb but low levels of Gzma as shown by semi-quantitative RT-PCR (A) and quantitative RT-PCR (B; n=2 for all groups). Gzmb levels were also higher in SOD1 astrocytes compared to WT astrocytes (A-B).
Figure 14B:
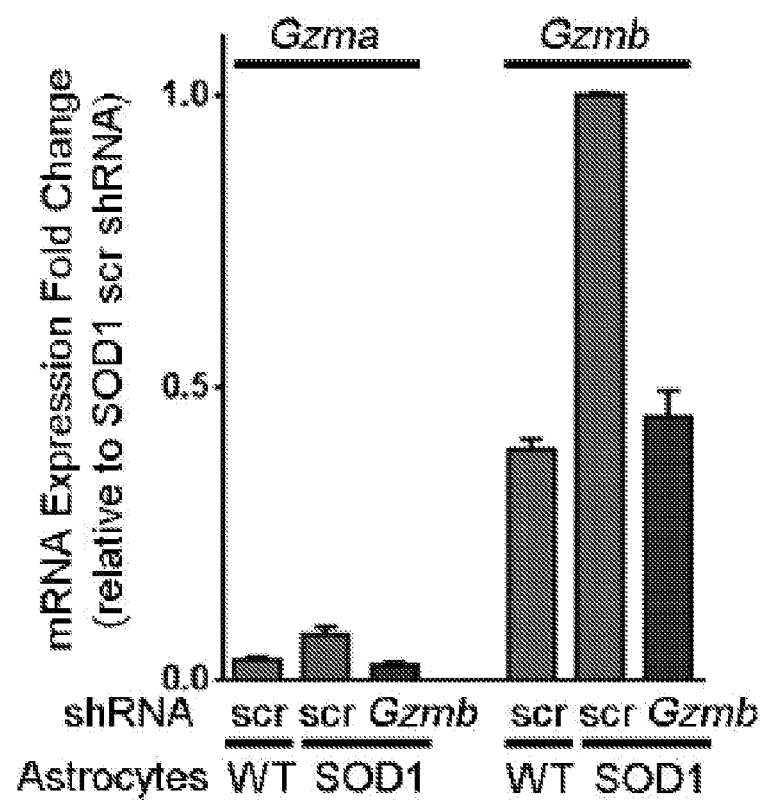

Furthermore, levels of expression of Gzma and Gzmb in astrocytes were analyzed. SOD1 astrocytes expressed high levels of Gzmb but low levels of Gzma as shown by semi-quantitative RT-PCR (FIG. 14A) and quantitative RT-PCR (FIG. 14B; n=2 for all groups). Gzmb levels were also higher in SOD1 astrocytes compared to WT astrocytes (FIGS. 14A and B).

Example 2

ALS Astrocytes Release Perforin and Granzyme B into Motor Neurons

Figure 2A:
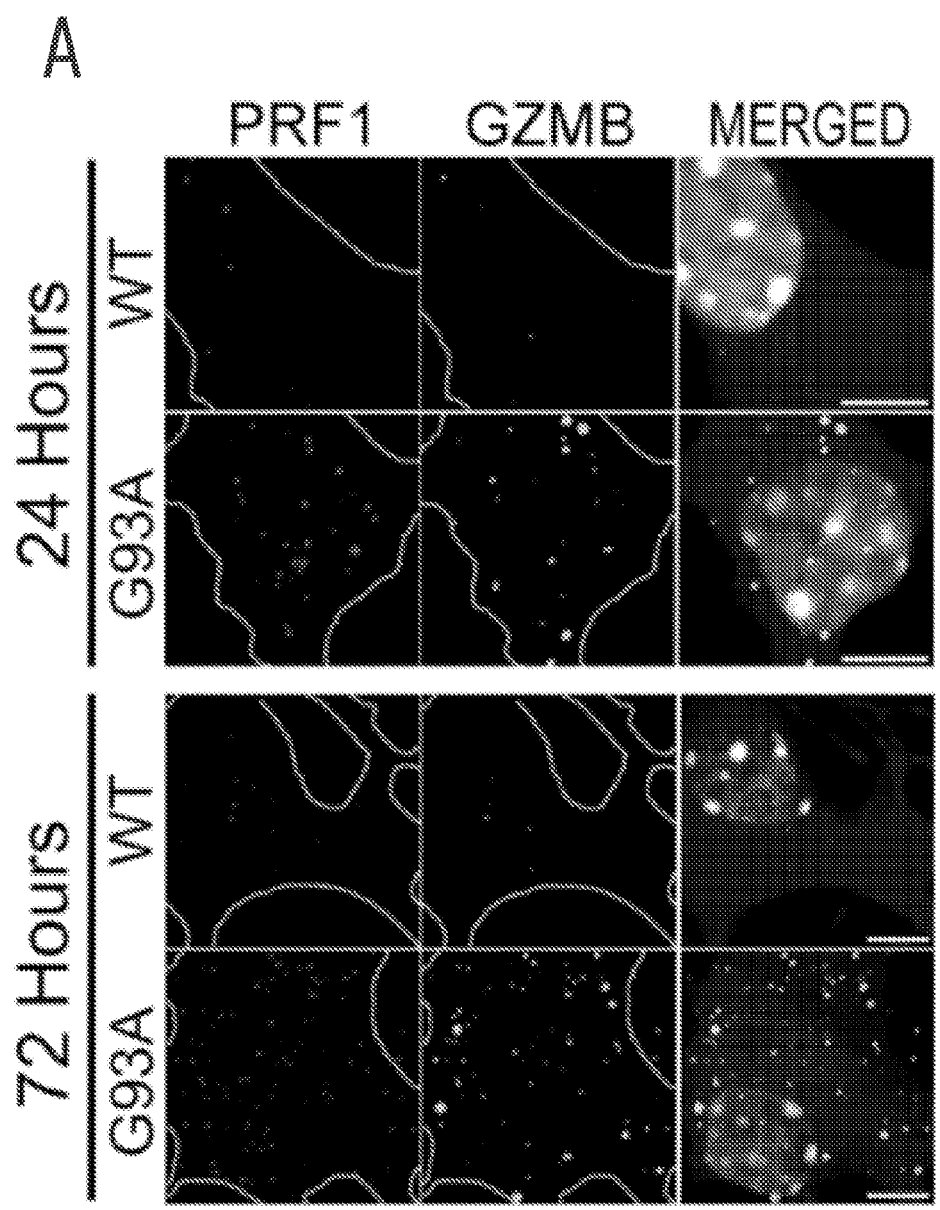
FIG. 2: (A) PRF1 and GZMB are seen in MNs as early as 24 hours upon co-culture with SOD1$^{G93A}$ astrocytes. PRF1 and GZMB incidence in MNs co-cultured with SOD1$^{G93A}$ astrocytes gradually increase with time but remain absent in MNs co-cultured with wild-type astrocytes. PRF1 is shown in red, GZMB is shown in green, Hb9-GFP is shown in blue. \*\*\*, p<0.001. Scale bar represents 5 µm. (B) Three dimensional confocal image generated from FIG. 2A shows that multimer perforin pore-like structures extend from the surface of Sod1$^{G93A}$ astrocytes into the cytoplasm of MNs. PRF1 is shown in red; Hb9-GFP$^+$ is shown in green; EAAT2 is shown in blue. (C) In Sod1$^{G93A}$ mice, PRF1 and GZMB are commonly found. PRF1 is shown in red; GZMB is shown in green; ChAT is shown in blue. Scale bars represent 50 µm. (D) In Sod1$^{G93A}$ mice, PRF1 and GZMB can be detected in MNs. PRF1 is shown in red; GZMB is shown in green; ChAT is shown in blue. (E) The level of degranularization as evaluated by expression of the lysosomal-associated membrane protein, CD107A, increases with disease progression in the spinal cord of Sod1$^{G93A}$ mice. CD107A is shown in red; EAAT2 is shown in green; ChAT is shown in blue. (F) The level of degranularization as evaluated by expression of the lysosomal-associated membrane protein, CD107A, is pronounced on astrocytes that surround MNs in Sod1$^{G93A}$ mice. CD107A is shown in red; EAAT2 is shown in green; ChAT is shown in blue. Scale bars represent 200 µm. (G-H) Levels of PRF1 (G) and GZMB (H) found at different time points in MNs co-cultured with wild-type or SOD1$^{G93A}$ astrocytes as shown in (A). (I) Non-ALS control astrocytes (1800) overexpressing SOD1 G93A or A4V mutant proteins release PRF1 and GZMB into MNs, but PRF1 and GZMB remain absent in MNs co-cultured with non-ALS control astrocytes after 120 hours of culture. PRF1 is shown in red, GZMB is shown in green, Hb9-GFP is shown in blue. Scale bar represents 5 µm. (J) Shows three dimensional images obtained with a confocal microscope showing lack of PRF1 staining (red) in MNs upon co-culture with wild-type astrocytes. EAAT2 (blue), an astrocyte surface marker, was used to visualize astrocyte membrane; Hb9-GFP (green) was used to visualize MN. Scale bar represents 100 µm. (K) Western blot analysis revealed that both primary and NPC derived SOD1$^{G93A}$ astrocytes show higher level of CD107A expression, an indicator of degranulation of cytolytic proteins compared to wild-type astrocytes. (L) Immunofluorescence staining of MNs co-cultured with astrocytes showed that CD107A expression is pronounced on SOD1$^{G93A}$ astrocytes surrounding MNs. CD107A is shown in red, Hb9-GFP is shown in green, EAAT2 is shown in blue. Scale bar represents 100 μm.

This example investigated whether SOD1$^{G93A}$ astrocytes have the ability to release PRF1 and GZMB into MNs by using an in vitro culture system to demonstrate the toxicity of astrocytes towards co-cultured MNs. MNs were derived from mES cells expressing GFP under the control of the motor-neuron specific HB9 promoter, permitting visual distinction of MNs and astrocytes in co-cultures. In MNs cultured on a confluent layer of astrocytes isolated from SOD1$^{G93A}$ mice, cytosolic and membrane-associated PRF1 and GZMB protein were visualized as early as 24 hours after plating, while MNs co-cultured with wild type astrocytes did not exhibit any signal at this time point. This difference was maintained over the time course of co-culture, leading to substantial accumulation of PRF1 and GZMB protein in MNs cultured on top of SOD1$^{G93A}$ astrocytes after 120 hours of culture, whereas both proteins remained essentially absent from MNs cultured on wild type astrocytes (see FIG. 2A). Levels of PRF1 (FIG. 2G) and GZMB (FIG. 2H) were analyzed at different time points in MNs co-cultured with wild-type or SOD1$^{G93A}$ astrocytes as shown in FIG. 2A.

Non-ALS control astrocytes overexpressing SOD1 mutations release PRF1 and GZMB into motor neurons. Non-ALS control astrocytes (1800) overexpressing SOD1 G93A or A4V mutant proteins, which have been shown to convey toxicity to MNs, release PRF1 and GZMB into MNs. PRF1 and GZMB remain absent in MNs co-cultured with non-ALS control astrocytes after 120 hours of culture (see FIG. 2I).

Perforin-mediated transfer of GZMB from effector to target cells is believed to involve the formation pore-resembling structures in the membrane of the target cell. Thus, the interaction between SOD1$^{G93A}$ astrocytes and MNs using confocal microscopy technology with three-dimensional imaging capability was examined.

Figure 2B:
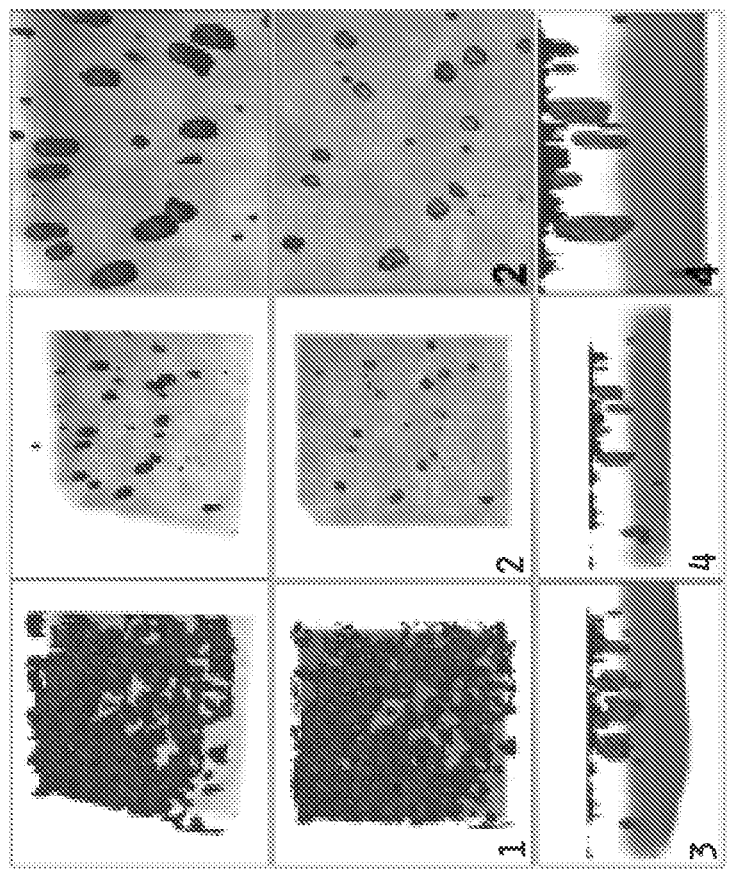
Figure 2B:
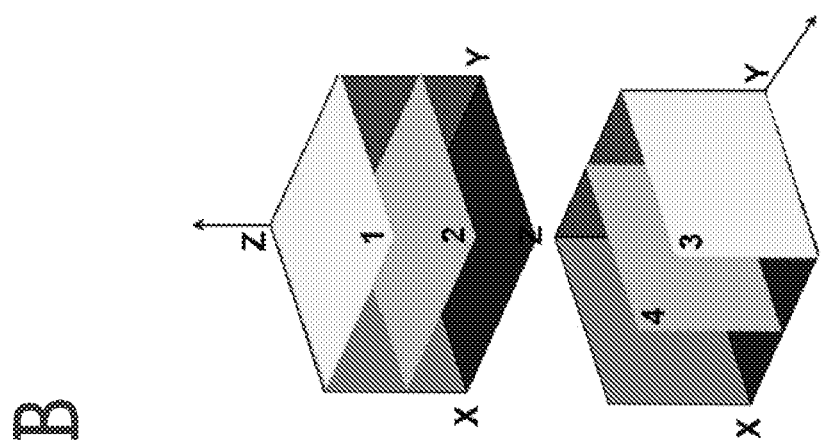
Figure 2C:
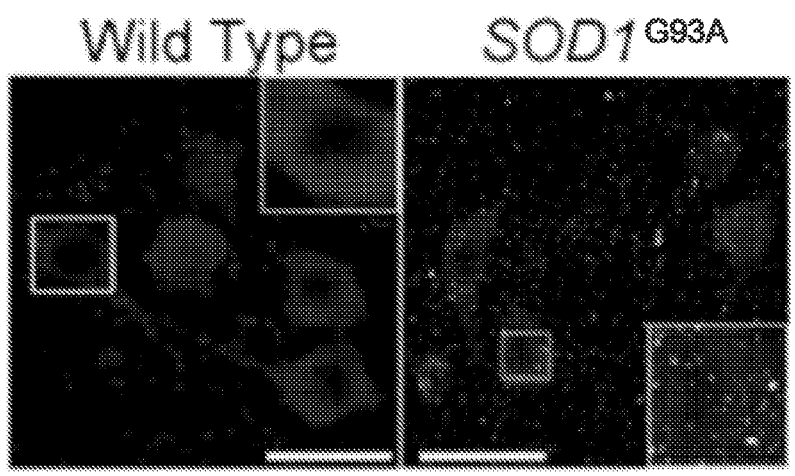
Figure 2D:
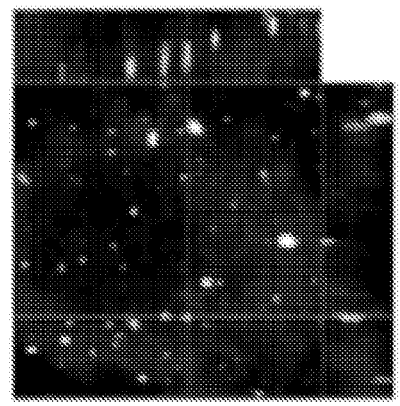
Figure 2E:
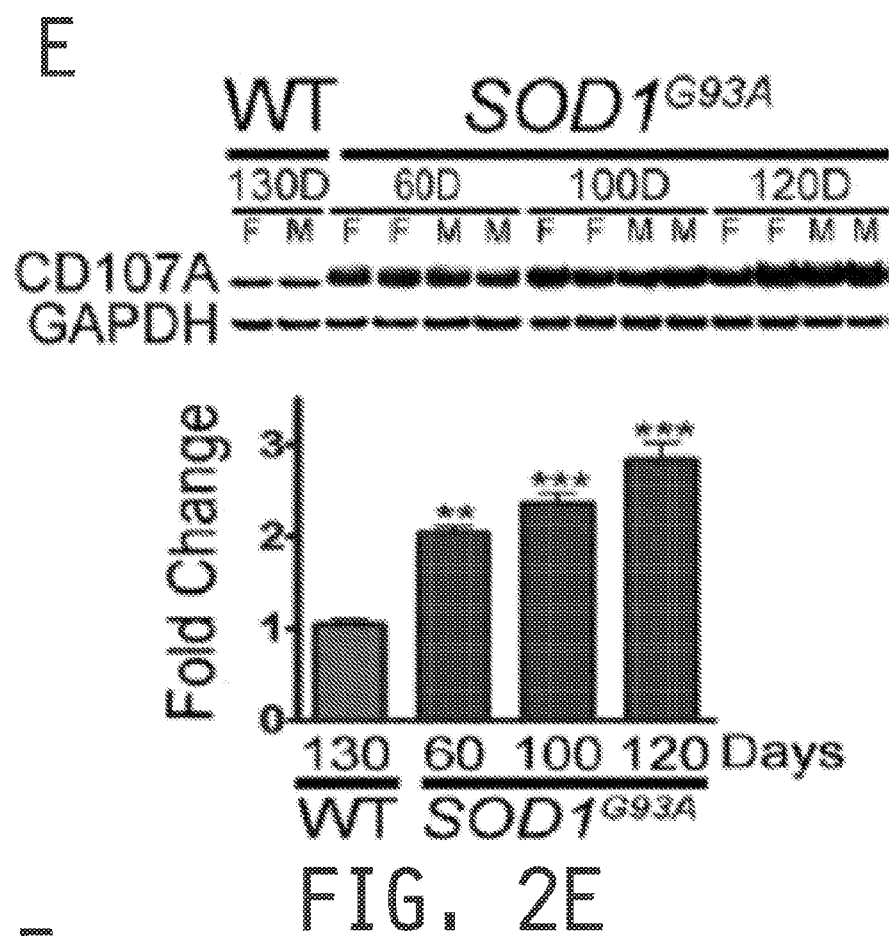
Figure 2F:
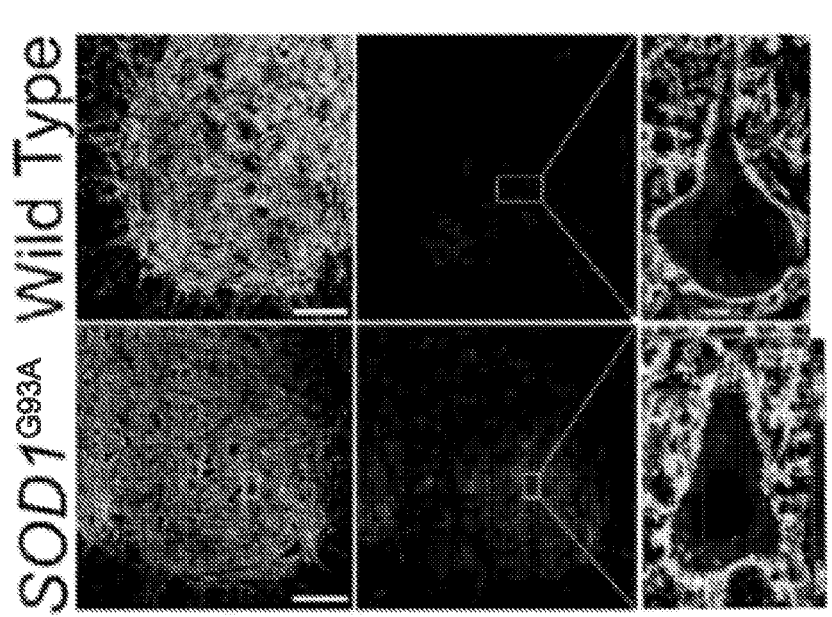
Figure 2G:
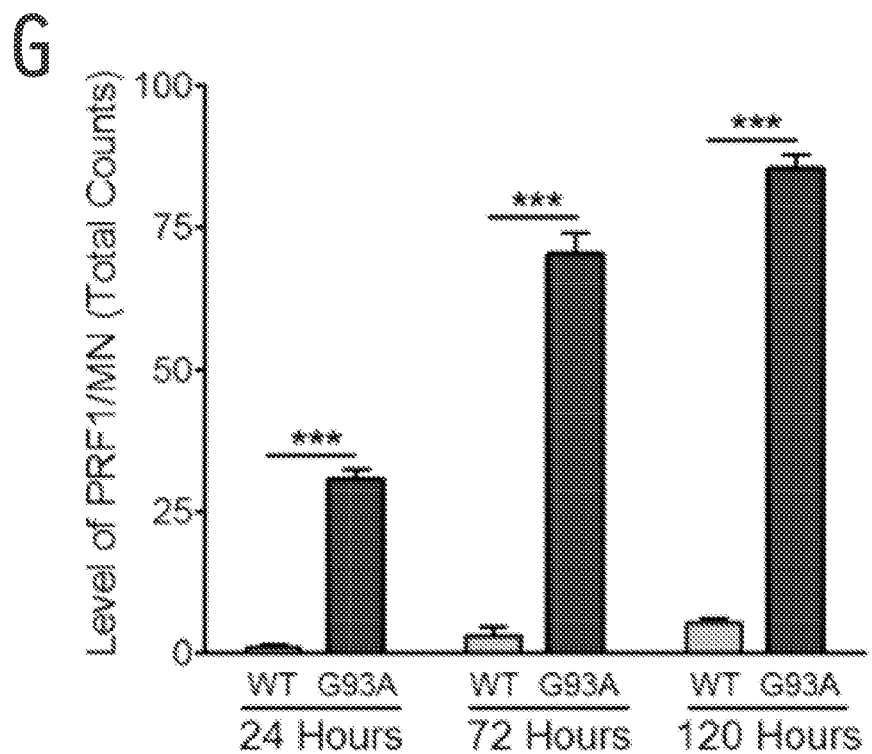
Figure 2H:
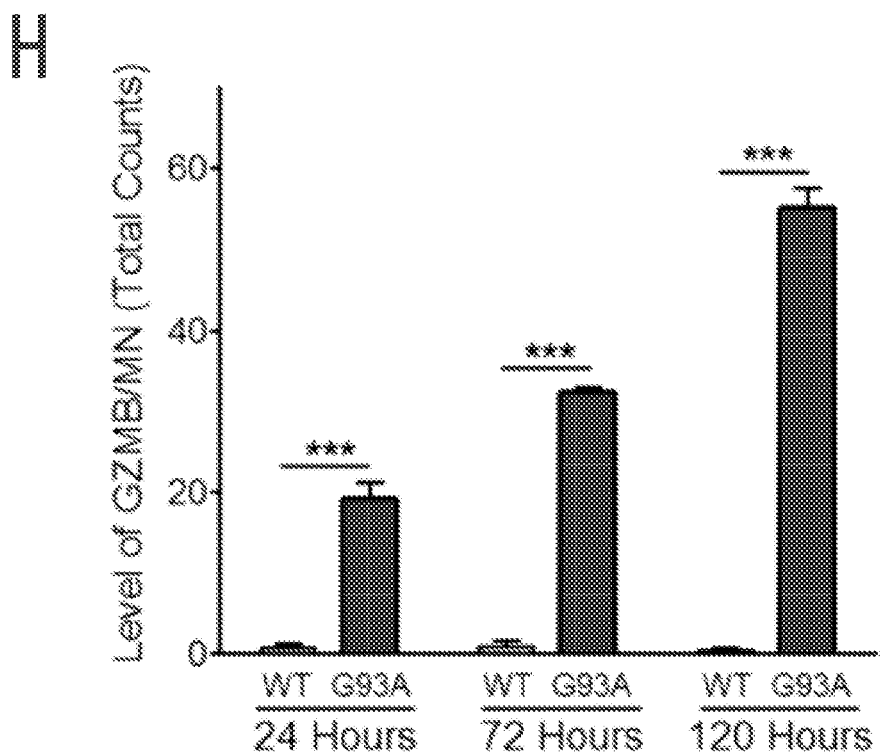
Figure 2I:
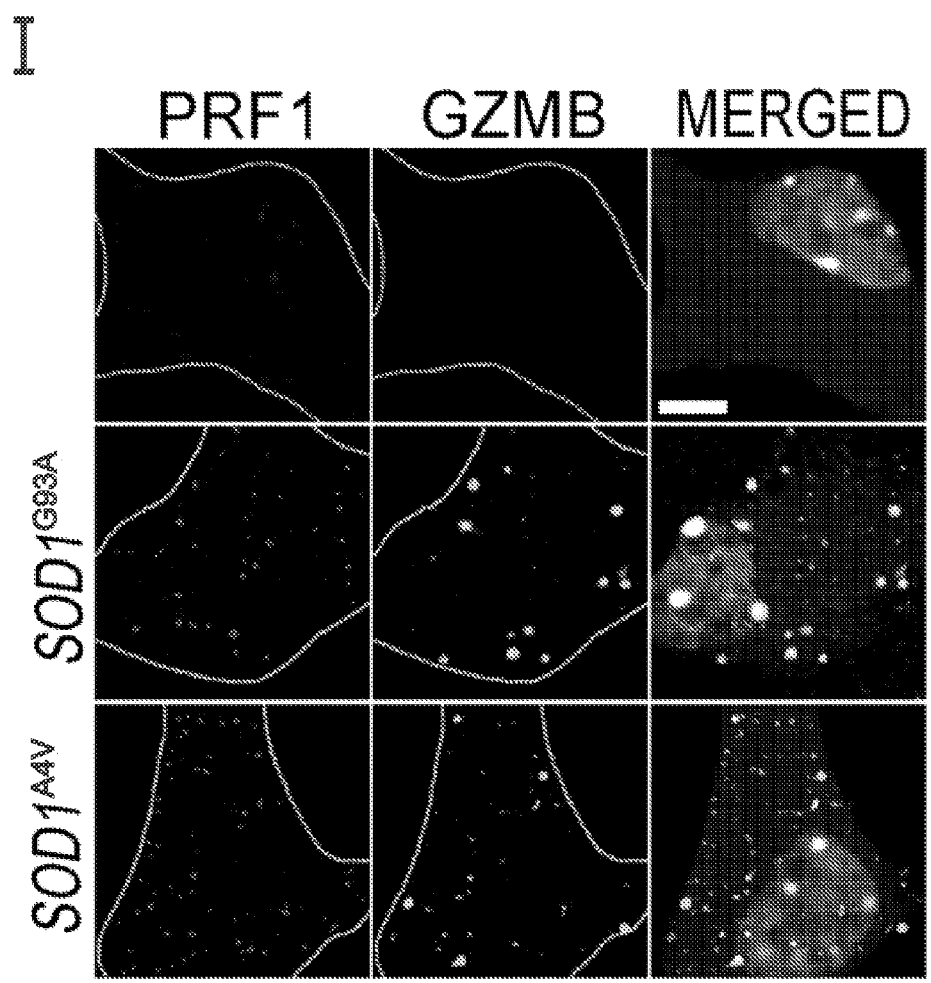
Figure 2J:
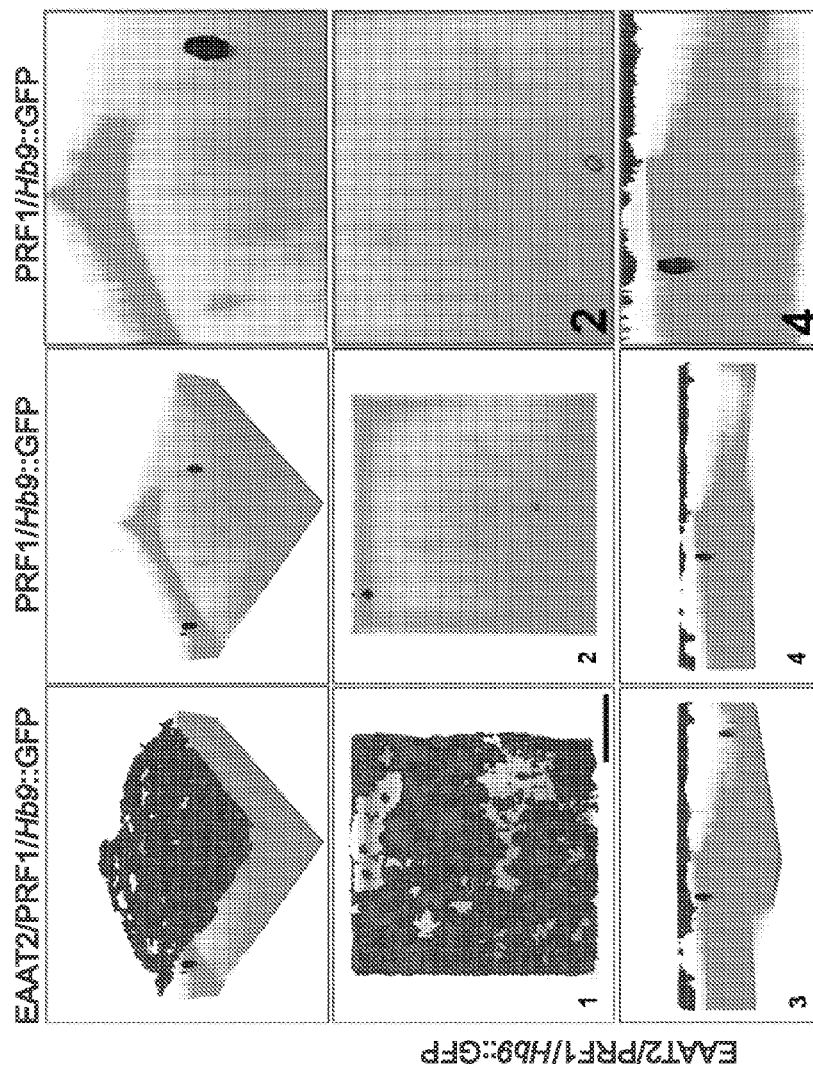
Figure 2J:
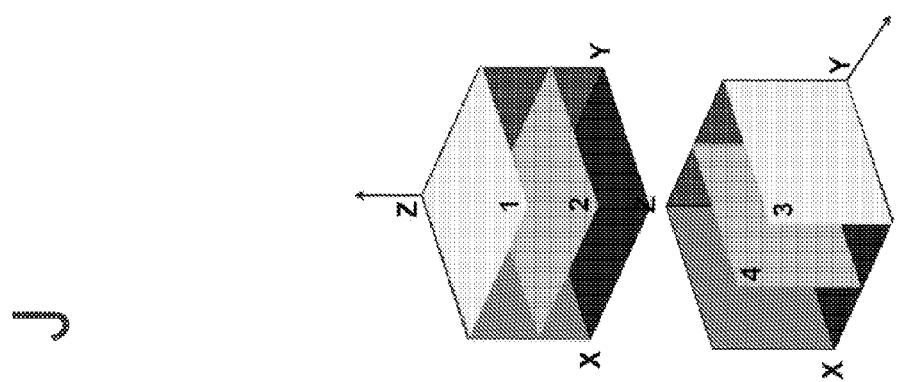

As shown in FIG. 2B, PRF1-staining co-localized with pore-like structures in the intercellular space between SOD1$^{G93A}$ astrocytes and the targeted MNs. In co-cultures of wild type astrocytes with MNs, such structures were absent. In spinal cord sections, PRF1 and GZMB were present within MNs of SOD1$^{G93A}$ but not in wild type mice, thus confirming the findings in vivo (see FIGS. 2C and 2D). Three dimensional images were obtained with a confocal microscope showing lack of PRF1 staining in MNs upon co-culture with wild-type astrocytes (see FIG. 2J).

Figure 2K:
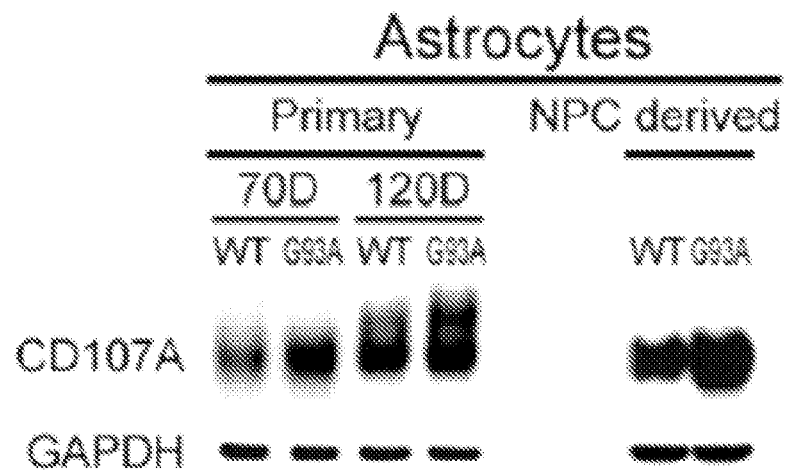
Figure 2L:
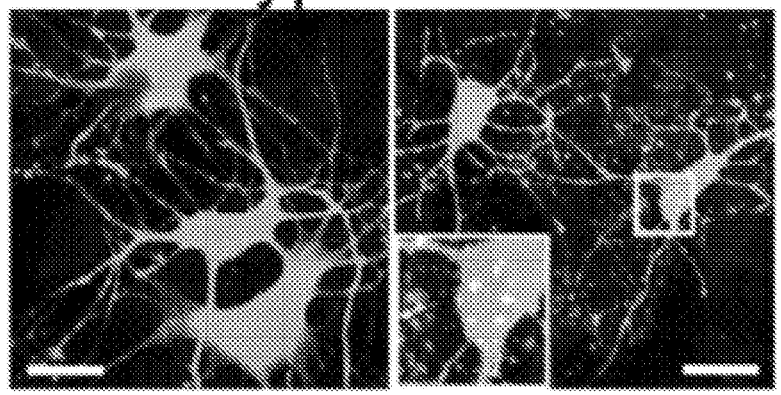

To verify active exocytosis of PRF1 and GZMB by ALS astrocytes, the expression of the lysosomal-associated membrane glycoprotein LAMP-1/CD107A (i.e., a prototypic marker of this process in cytotoxic lymphocytes) was determined. LAMP-1/CD107A was substantially upregulated in SOD1$^{G93A}$ spinal cord cells compared to wild type cells, thus indicative of active degranulation (see FIG. 2E). Consistent with this observation, CD107A levels increased with disease progression in SOD1$^{G93A}$ mice. Importantly, surface CD107A was prominent only on SOD1$^{G93A}$ astrocytes, both in vitro and in vivo, but not on wild-type cells (see FIG. 2F). Increased degranulation was observed in SOD1$^{G93A}$ astro-cytes upon co-culture with motor neurons. Western blot analysis revealed that both primary and NPC derived SOD1$^{G93A}$ astrocytes show higher level of CD107A expression, an indicator of degranulation of cytolytic proteins compared to wild-type astrocytes (see FIG. 2K). Immunofluorescence staining of MNs co-cultured with astrocytes showed that CD107A expression is pronounced on SOD1$^{G93A}$ astrocytes surrounding MNs (see FIG. 2L).

Example 3

Figure 3A:
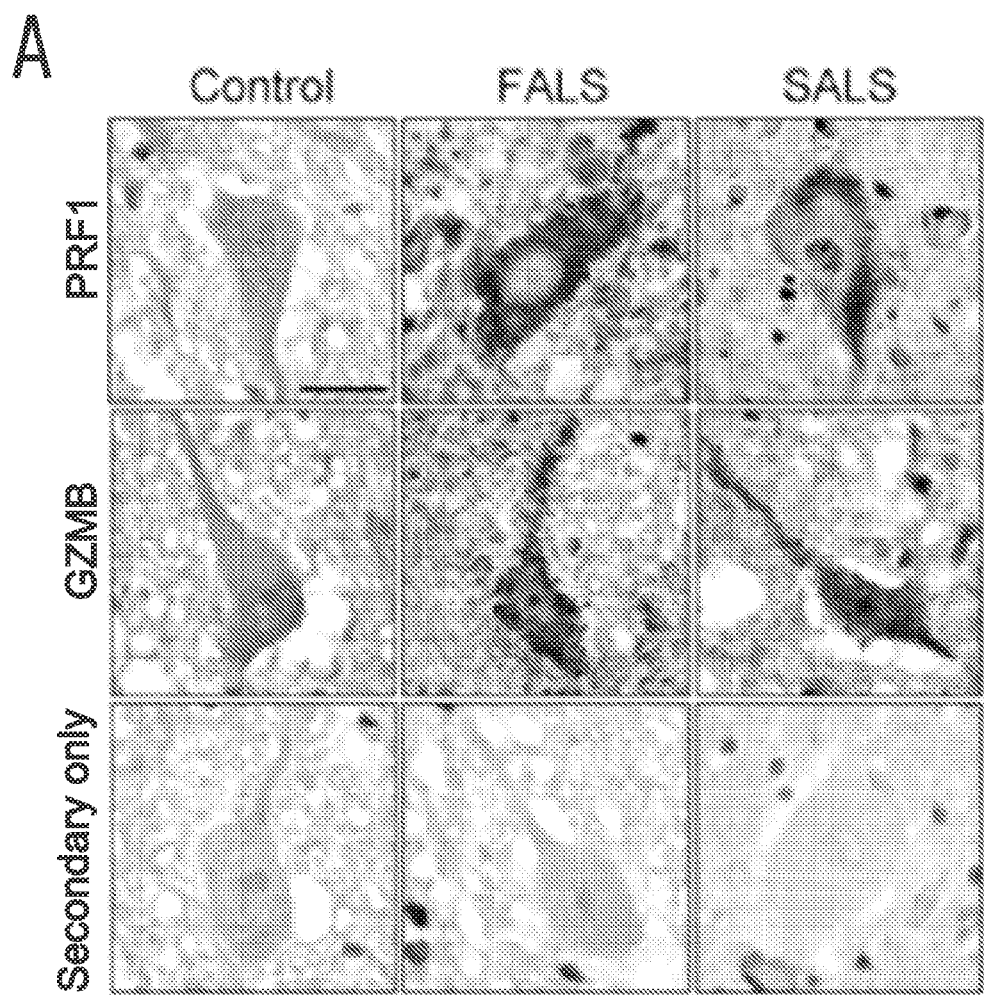
FIG. 3: (A) Detection of PRF1 and GZMB in MNs found in spinal cords of human ALS as assayed by 3,3'-Diaminobenzidine (DAB) immunostaining. (B) Quantification of the number of motor neurons positive for PRF1 as shown in FIG. 3A. Scale bars represent 20 μm. (C) Quantification of the number of motor neurons positive for GZMB as shown in FIG. 3A. Scale bars represent 20 μm.

Perforin and Granzyme B are Specifically Found in Motor Neurons of Human ALS Spinal Cords Consistent with outcomes in the mouse model, substantial amounts of PRF1 and GZMB were detected in MNs of the spinal cord of FALS and SALS patients but not in unaffected controls (see FIG. 3A). Quantitative analysis of the number of MNs positive for PRF1 or GZMB in human spinal cord demonstrated a high prevalence of positive MNs in both FALS and SALS, with up to 100% of cells containing both proteins in several samples (see FIGS. 3B and 3C). These observations, derived from in vitro co-culture systems of ALS astrocytes with MNs and from both murine and human ALS spinal cords, suggest that ALS astrocytes actively degranulate PRF1 and GZMB, followed by perforin-mediated uptake of these cells into MNs.

Example 4

ALS Astrocytes Utilize Perforin and Granzyme B to Kill Motor Neurons

Figure 4A:
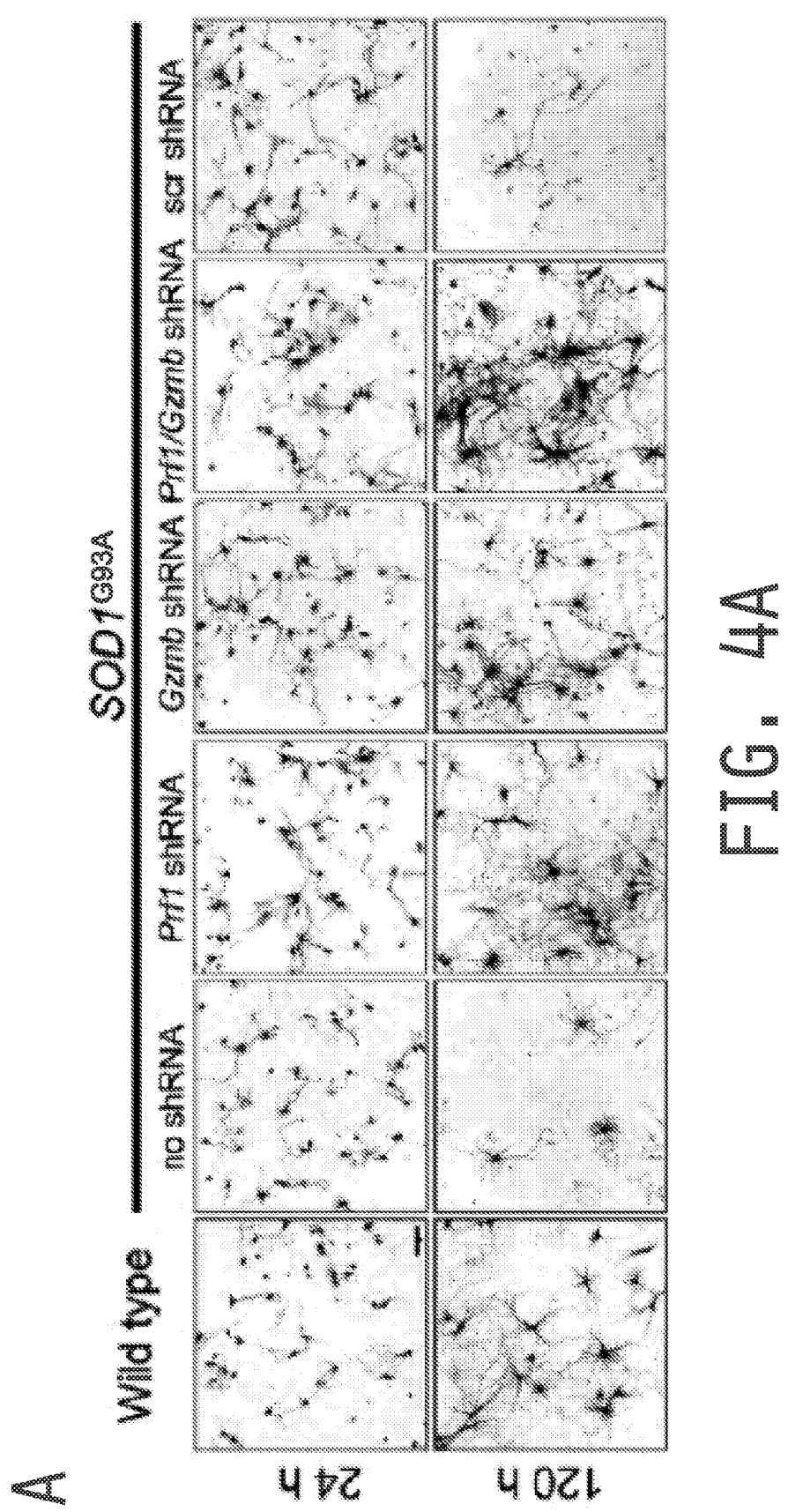
FIG. 4: (A) Knockdown of Prf1 and GzmB expression in Sod1$^{G93A}$ astrocytes rescues co-cultured MNs. (B) Knockdown of Prf1 and GzmB expression in Sod1$^{G93A}$ astrocytes rescues total counts of HB9-GFP$^+$ cells. (C) Knockdown of Prf1 and GzmB expression in Sod1$^{G93A}$ astrocytes prevents atrophy of the MN soma. (D) Knockdown of Prf1 and GzmB expression in Sod1$^{G93A}$ astrocytes prevents shortening of neurites. (E) Knockdown of Prf1 and GzmB in FALS and SALS astrocytes rescues co-cultured MNs. (F) Knockdown of Prf1 and GzmB in FALS and SALS astrocytes rescues total counts of HB9-GFP$^+$ cells. (G-H) Knockdown of Prf1 and GzmB expression in FALS and SALS astrocytes prevents atrophy of the MN soma. (I-J) Knockdown of Prf1 and GzmB expression in FALS and SALS astrocytes prevents shortening of neurites. (*=p<0.05; =p<0.01; *, p<0.001; ns=non-significant; Scr=scramble). (K-L) Western blot analysis showed reduced expression of PRF1 and GZMB in mouse SOD1$^{G93A}$ astrocytes upon lentiviral transduction with Prf1 shRNA (K) and Gzmb shRNA (L). (M) Prf1 shRNA and Gzmb shRNAs suppressed PRF1 and GZMB expression in all human astrocytes used. GAPDH was used as a loading control. 'a' represents astrocytes transduced with scrambled shRNA, 'b' represents astrocytes transduced with Prf1 shRNA and Gzmb shRNA. Scr represents scrambled shRNA.
Figure 4B:
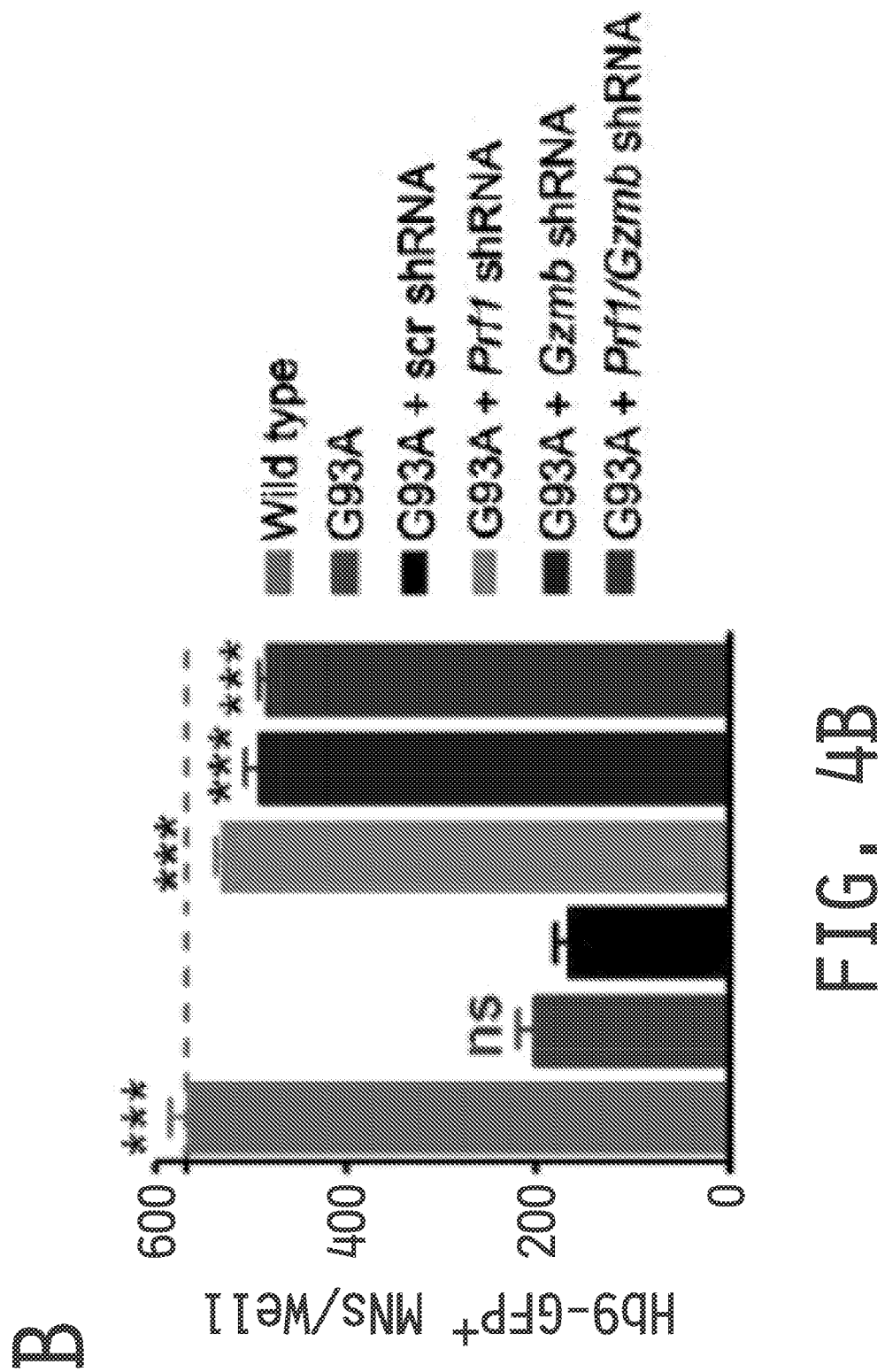
Figures 4C, 4D:
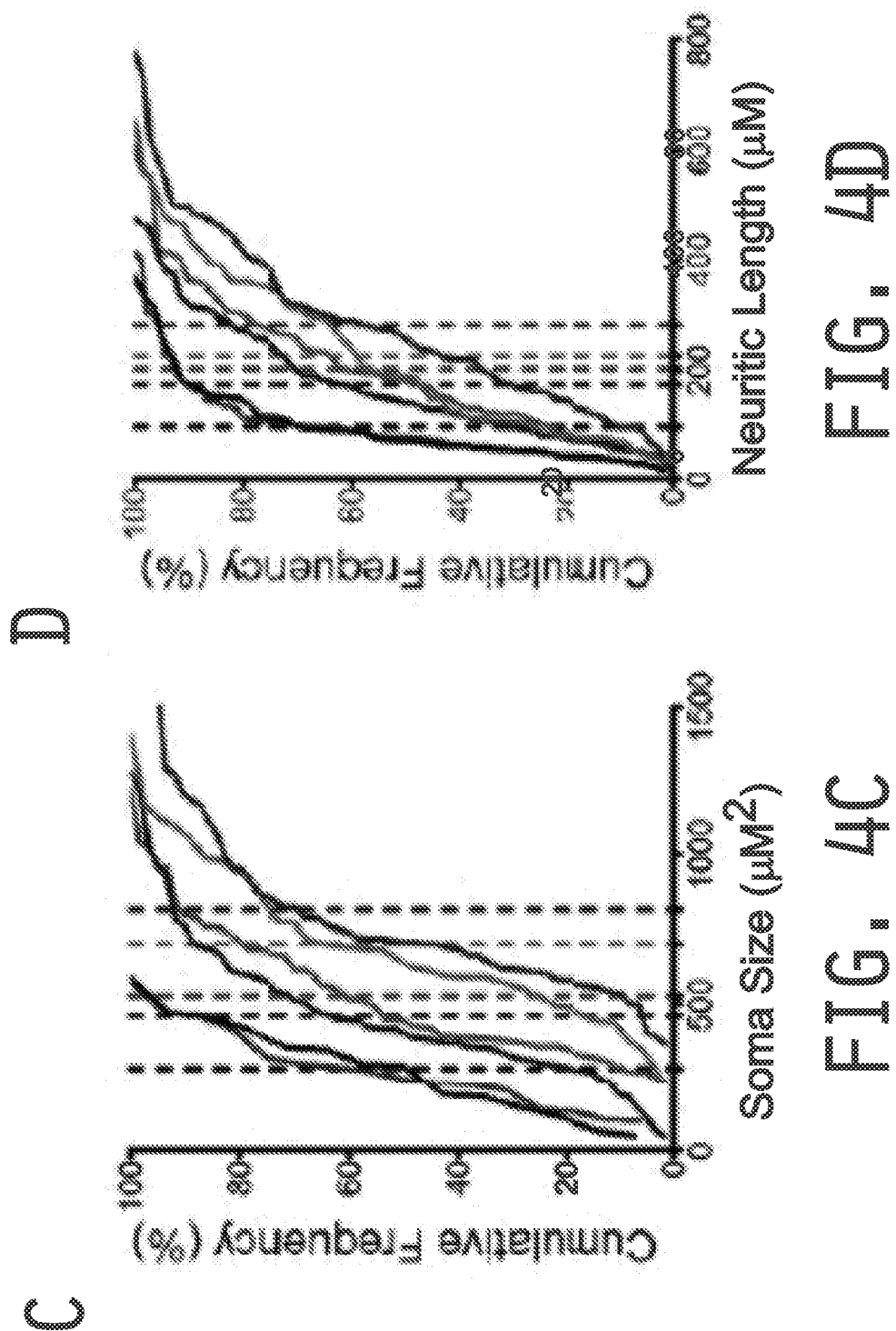
Figure 4E:
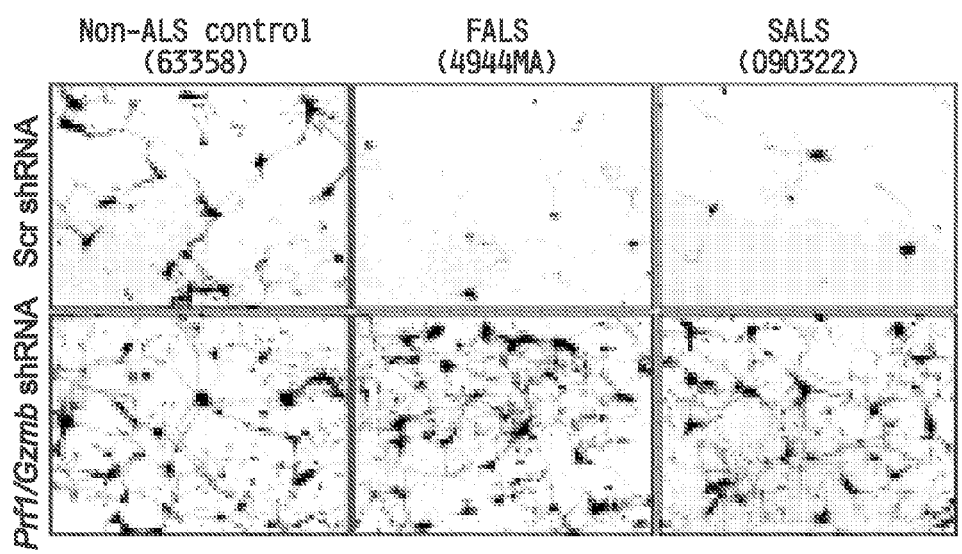
Figure 4F:
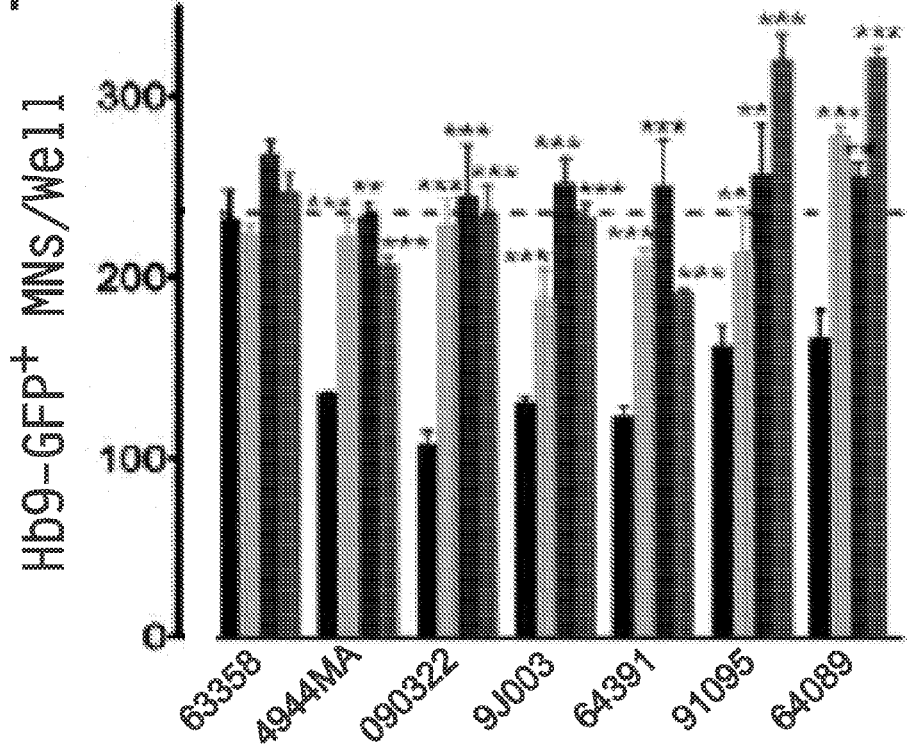

In this example, the functional significance of the PRF1/GZMB pathway in ALS astrocyte-mediated MN toxicity was determined. First, shRNAs that were capable of efficiently ablating expression of Prf1 and Gzmb in astrocytes were identified. Ablation of Prf1 and Gzmb expression in SOD1$^{G93A}$ astrocytes resulted in an almost complete protection of MNs during co-culture (see FIGS. 4A and B). This protective effect manifested in a larger number of surviving MNs (see FIG. 4B), less soma atrophy (see FIG. 4C), and increased neuritic length (see FIG. 4D). The specificity of this protective effect was confirmed by unaltered MN-directed toxicity of SOD1$^{G93A}$ astrocytes treated with a scrambled shRNA control, resulting in death of 80% of MNs within 20 hours of co-culture.

Figure 4K:
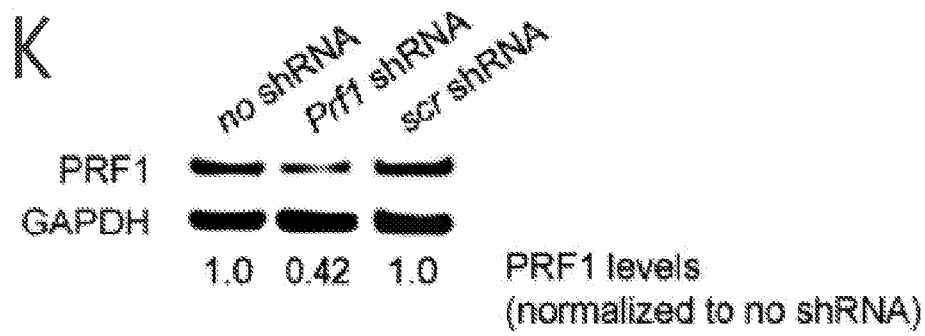
Figure 4L:
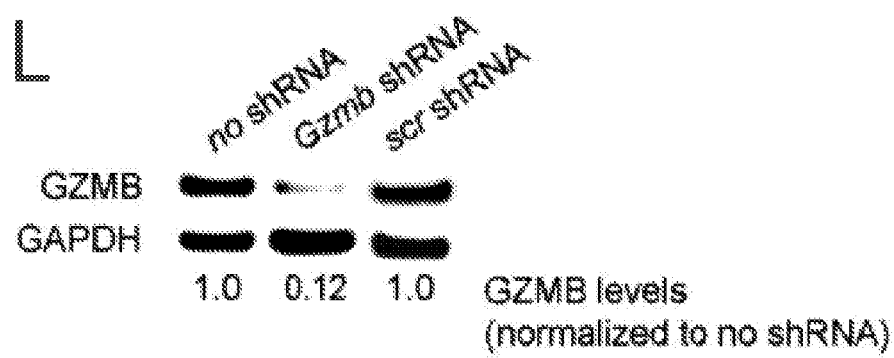
Figure 4M:
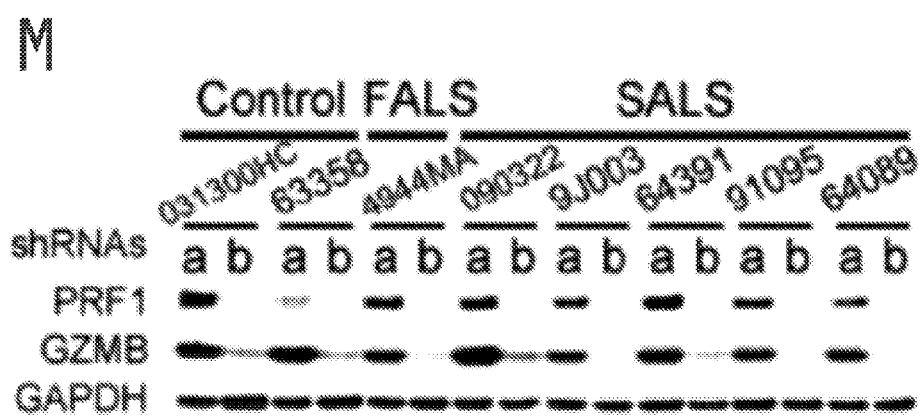

ShRNA knockdown of perforin and granzyme B was detected in Astrocytes. Western blot analysis showed reduced expression of PRF1 and GZMB protein in mouse SOD1$^{G93A}$ astrocytes upon lentiviral transduction with Prf1 shRNA (FIG. 4K) and Gzmb shRNA (FIG. 4L). Prf1 shRNA and Gzmb shRNAs suppressed PRF1 and GZMB expression in all human astrocytes used (FIG. 4M).

Furthermore, shRNA-mediated ablation of Prf1 and GzmB expression in astrocytes derived from FALS and SALS patients effectively protected MNs in co-culture, with significant effects on soma atrophy and shortening of neurites (see FIGS. 4E-4J). Collectively, these results indicate that both murine and human FALS and SALS astrocytes utilize the cytolytic proteins PRF1 and GZMB to kill MNs. Suppressing the expression of these proteins in astrocytes attenuates ALS astrocyte-derived MN toxicity.

Figure 10A:
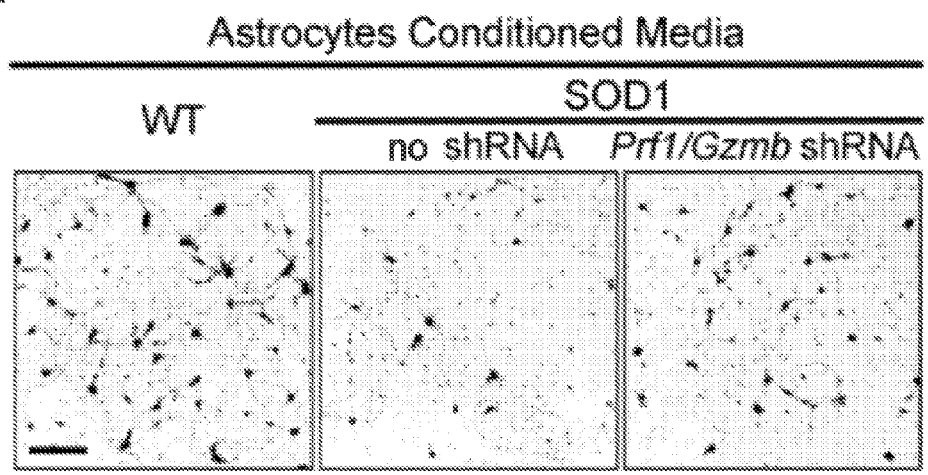
FIG. 10: Knockdown of Prf1 and Gzmb expression in SOD1 astrocytes increased MN survival (A-B) (B; n=3 for all groups, each n was run in triplicate) and prevented neurite (C) and soma size (D) retraction commonly observed when MNs are cultured in the presence of SOD1 astrocyte conditioned medium (C, D; n=100 for all groups). (E-F) In the presence of SOD1 astrocytes conditioned media, PRF1 and GZMB was detected in the soma of MNs. (G), Dose dependent increase in MN survival was observed in the presence of PRF1 and GZMB neutralizing antibodies added to SOD1 astrocyte conditioned medium. SOD1 astrocyte conditioned medium without antibody supplementation was used as the reference group for statistical analysis. Dotted lines represent 50% frequency (C, D). Scale bars, 200 μm (A), 5 μm (E). Error bars denote s.e.m. P<0.01, **P<0.0001. n.s, non-significant. Scr, scrambled shRNA.
Figure 10B:
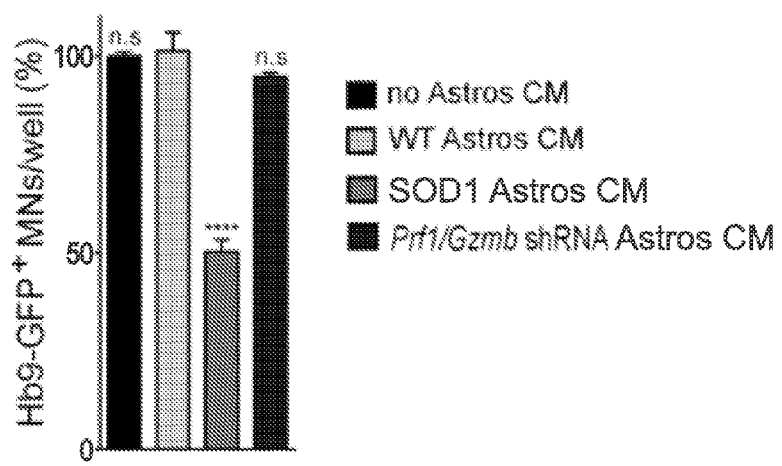
Figure 10C:
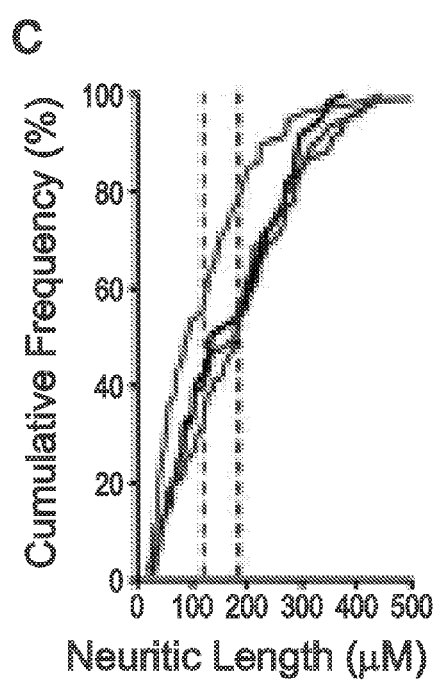
Figure 10D:
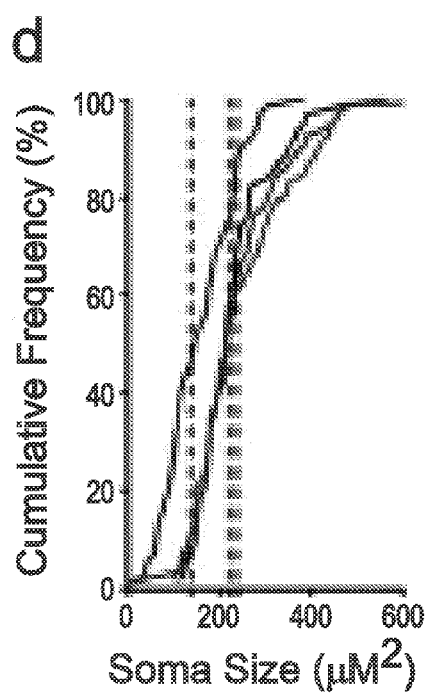
Figure 10E:
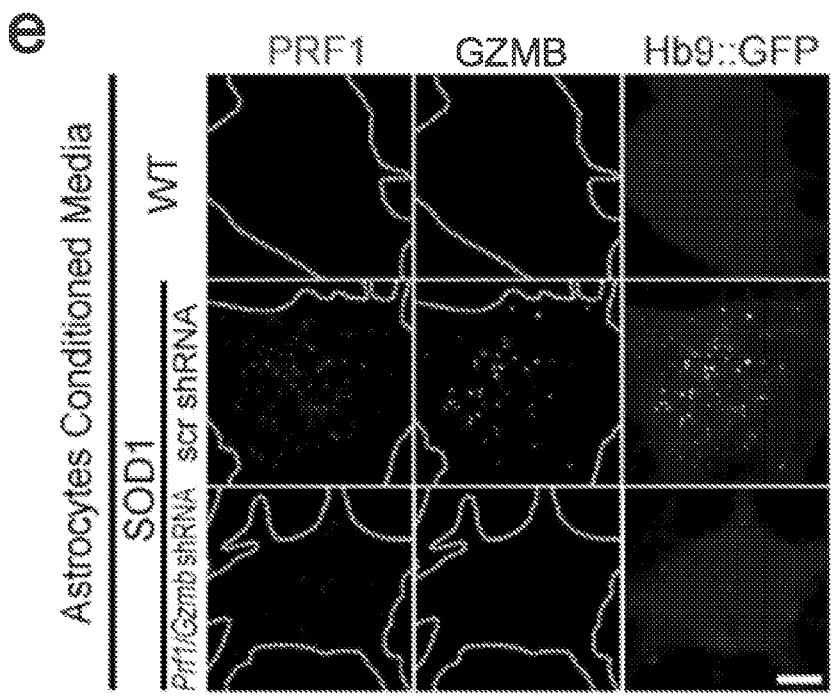
Figure 10F:
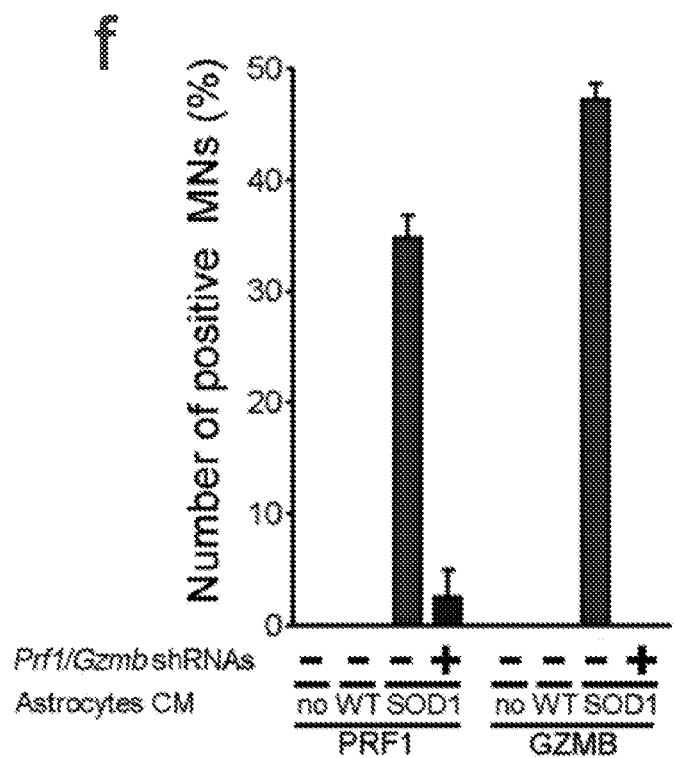
Figure 10G:
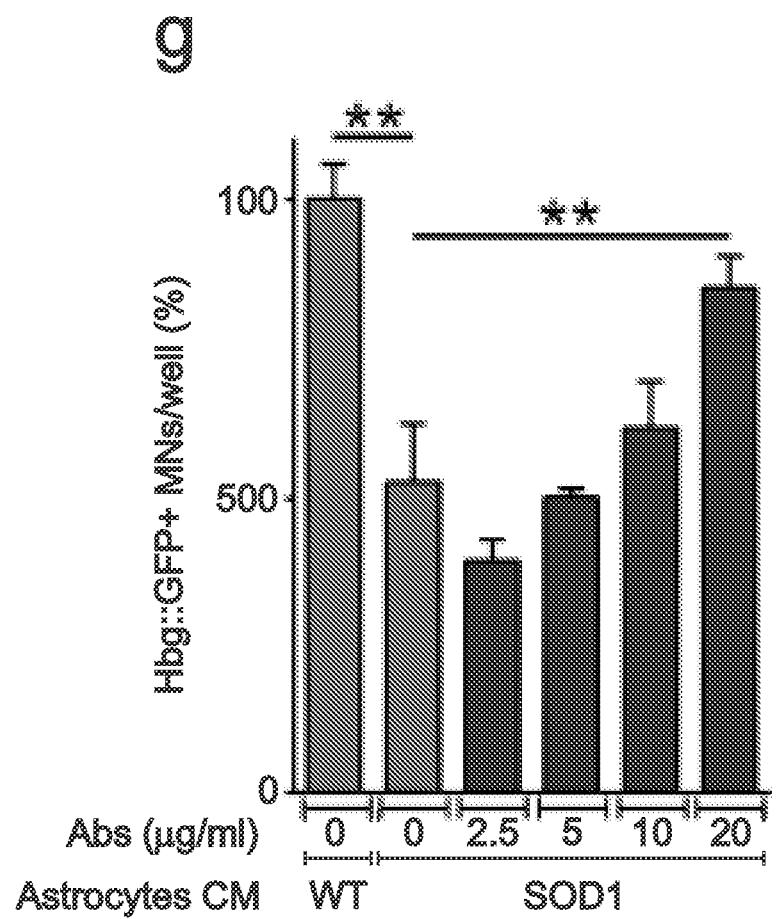

In addition, PRF1 and GZMB in ALS astrocytes conditioned medium were toxic to MNs. Knockdown of Prf1 and Gzmb expression in SOD1 astrocytes increased MN survival (FIGS. 10A and 10B) (B; n=3 for all groups, each n was run in triplicate) and prevents neurite (FIG. 10C) and soma size (FIG. 10D) retraction commonly observed when MNs are cultured in the presence of SOD1 astrocyte conditioned medium (FIGS. 10C and D; n=100 for all groups). In the presence of SOD1 astrocytes conditioned media, PRF1 and GZMB was readily detected in the soma of MNs (FIGS. 10E-F). Dose depended increase in MN survival observed in the presence of PRF1 and GZMB neutralizing antibodies added to SOD1 astrocyte conditioned medium (FIG. 10G). SOD1 astrocyte conditioned medium without antibody supplementation was used as a reference group for statistical analysis. Dotted lines represent 50% frequency (FIGS. 10C and D). Scale bars, 200 µm (FIG. 10A), 5 µm (FIG. 10E). Error bars denote s.e.m. P<0.01, **P<0.0001. n.s, non-significant. Scr, scrambled shRNA.

Figure 12A:
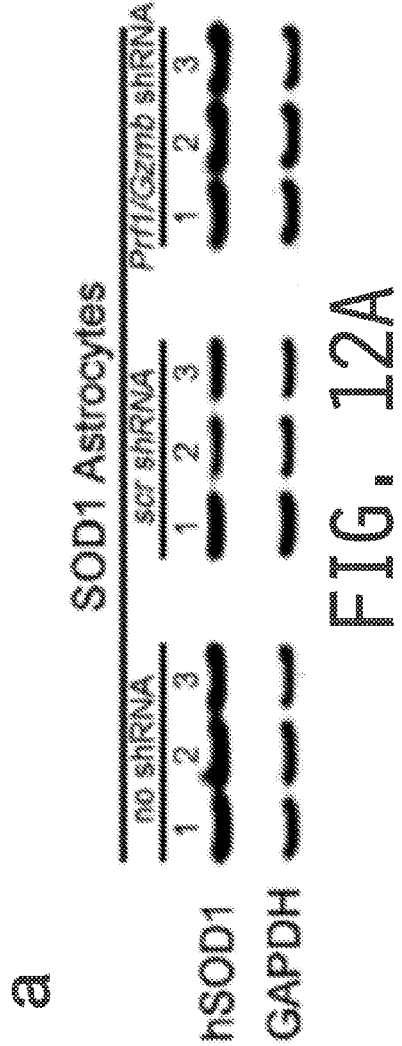
FIG. 12: (A) Western blot analysis showed similar levels of human SOD1 upon expression of PRF1 and GZMB shRNAs in SOD1 astrocytes. (B) Inflammatory gene array showed no overt changes in the inflammatory profile of SOD1 astrocytes upon knockdown of PRF1 and GZMB. Heatmap represents the average fold changes of two gene arrays using samples collected independently.
Figure 12B:
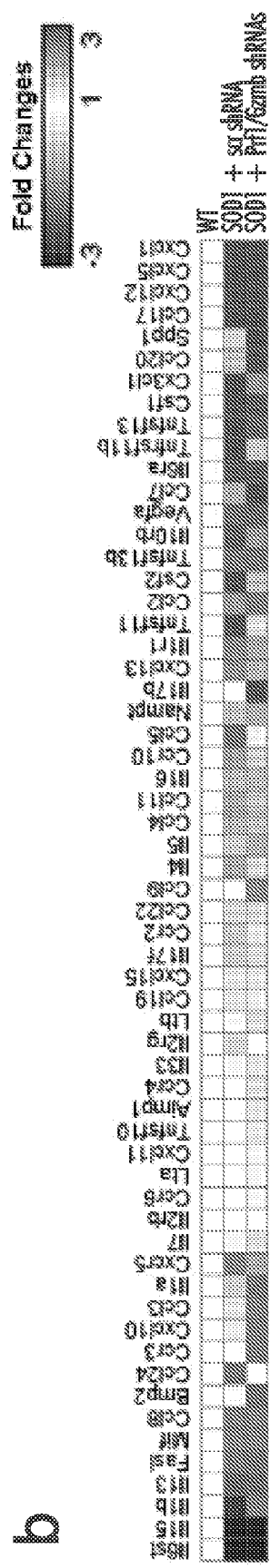

Furthermore, down-regulation of PRF and GZMB levels in astrocytes did not alter levels of human SOD1 nor the inflammatory profile observed in SOD1 astrocytes. Western blot analysis showed similar levels of human SOD1 upon expression of PRF1 and GZMB shRNAs in SOD1 astrocytes (FIG. 12A). An inflammatory gene array showed no overt changes in inflammatory profile of SOD1 astrocytes upon knockdown of PRF1 and GZMB (FIG. 12B). Heatmap represents the average fold changes of two gene arrays using samples collected independently.

Figure 13A:
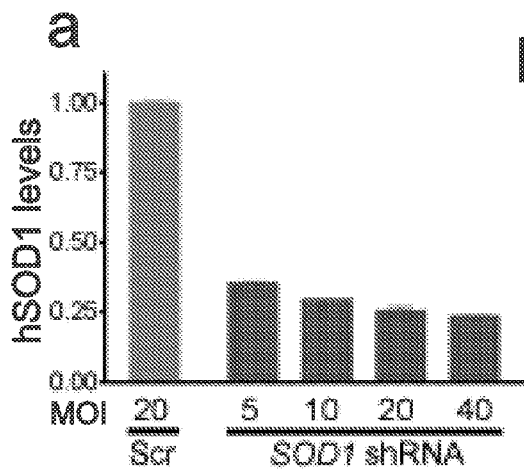
FIG. 13: (A) Levels of human SOD1 expression knockdown achieved in SOD1 astrocytes upon shRNA delivery via viral vectors shown by ELISA (A; n=2 for all groups) and Western analysis (B). (C-H) upon SOD1 shRNA expression, levels of PRF1 and GZMB co-localization were significantly decreased both in vitro (C-E) and in vivo (F-H)) without impacting on the total number of individual granules per cell (D, G)). White arrow head indicates PRF1 and GZMB co-localized granule. Scale bars, 5 µm. Error bars denote s.e.m. ****P<0.0001. n.s, non-significant. Scr, scrambled shRNA.
Figure 13B:
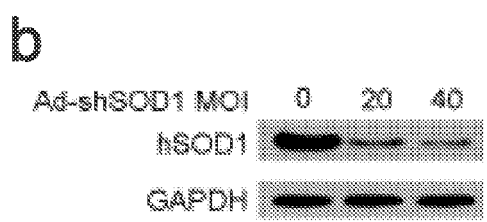
Figure 13C:
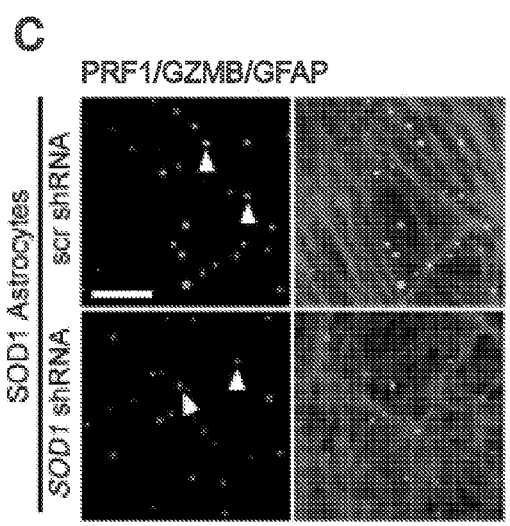
Figure 13D:
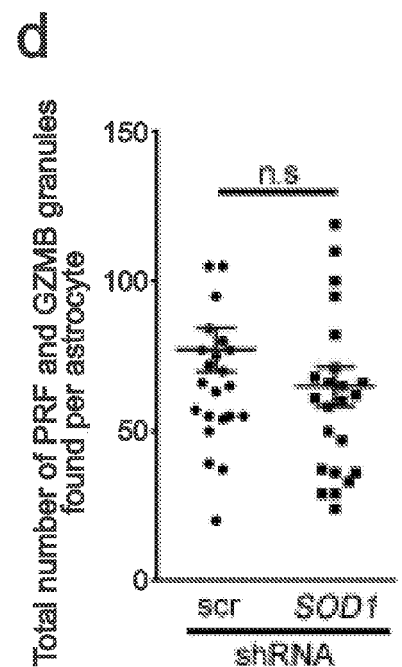
Figure 13E:
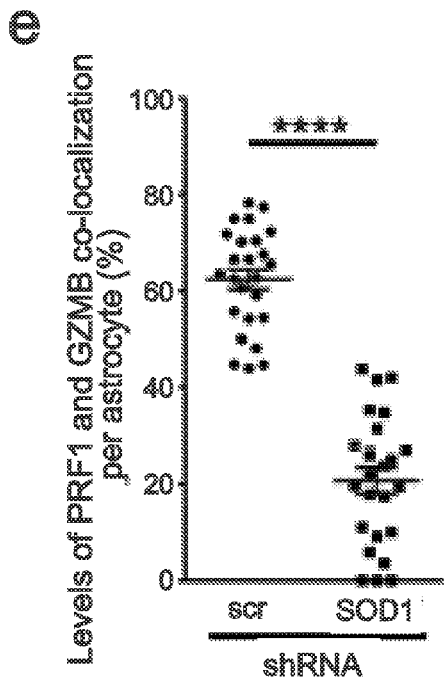
Figure 13F:
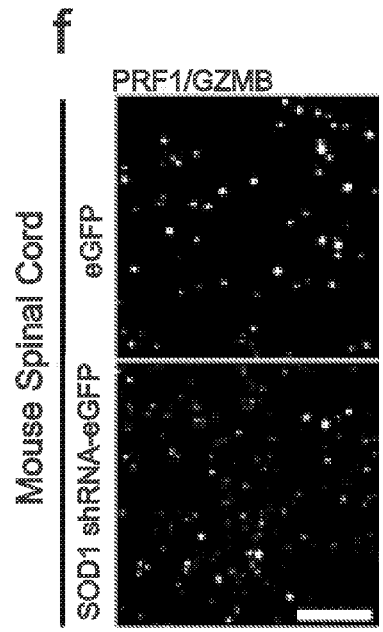
Figure 13G:
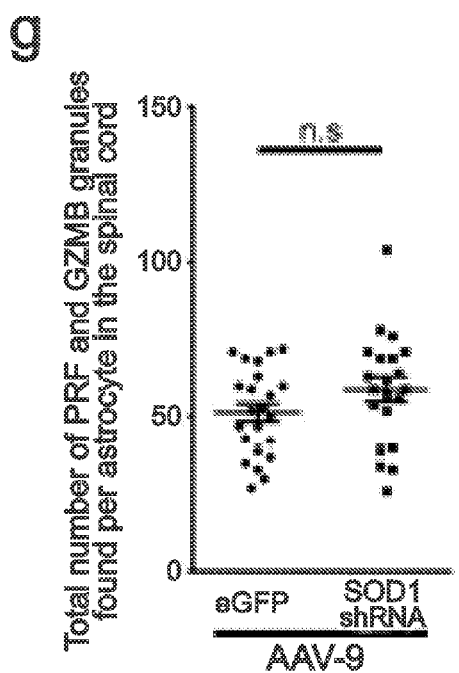
Figure 13H:
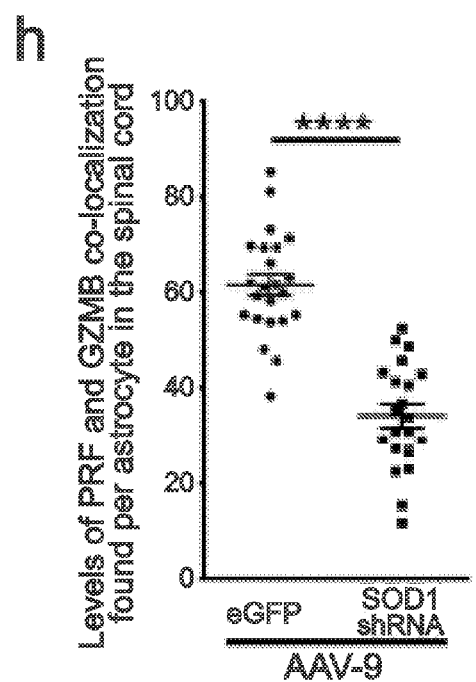

Moreover, human SOD1 targeting in SOD1$^{G93A}$ astrocytes resulted in decreased levels of co-localization of PRF1 and GZMB. Levels of human SOD1 expression knockdown achieved in SOD1 astrocytes upon shRNA delivery via viral vectors were shown by ELISA (FIG. 13A; n=2 for all groups) and Western analysis (FIG. 13B). Upon SOD1 shRNA expression, levels of PRF1 and GZMB co-localization were significantly decrease both in vitro (FIG. 13C-E) and in vivo (FIG. 13F-H) without impacting on the total number of individual granules per cell (FIGS. 13D and G). White arrow head indicates PRF1 and GZMB co-localized granule. Scale bars, 5 µm. Error bars denote s.e.m. ****P<0.0001. n.s, non-significant. Scr, scrambled shRNA.

Example 5

ALS Astrocytes Display NK-Like Cell Properties

Figure 5A:
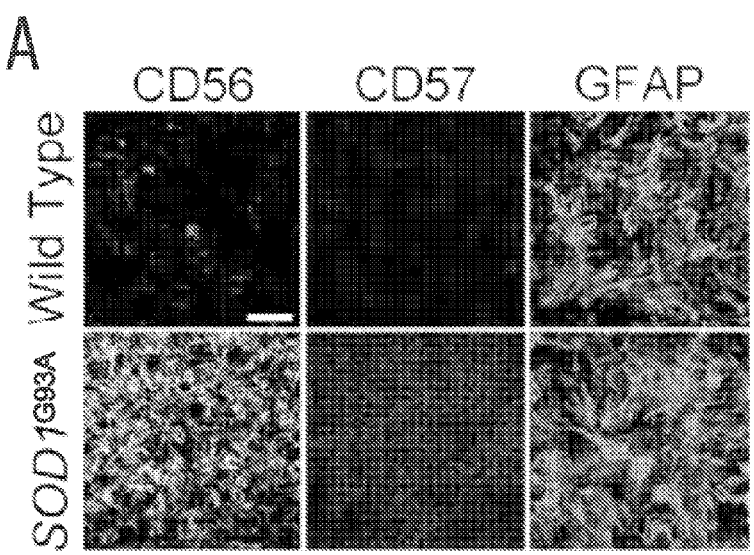
FIG. 5: (A) Similar to NK cells, Sod1$^{G93A}$ astrocytes express CD56 and CD57. Scale bars represent 100 μm. (B) Similar to NK cells, Sod1$^{G93A}$ astrocytes exhibit upregulation of markers commonly associated with NK cells. (C) Sod1$^{G93A}$ astrocytes express MHC class I receptors, evident from the robust expression of LY49C and LY49I in vitro. LY49C+I is shown in red; GFAP is shown in green. Scale bars represent 200 μm. (D) Sod1$^{G93A}$ astrocytes express MHC class I receptors, evident from the robust expression of LY49C and LY49I in vivo at disease end-stage in the spinal cord of Sod1$^{G93A}$ mice. LY49C+I is shown in red; GFAP is shown in green. Scale bars represent 500 μm and 200 μm (inset). (E) The MHC class I receptor, KIR3DL2 is expressed in FALS and SALS astrocytes. Scale bars represent 200 μm. (F) Screening of human MHC class I receptor variants by RT-PCR identified KIR3DL2 as being highly and commonly expressed in FALS and SALS astrocytes in vitro. Scale bars represent 200 μm and 5 μm (inset). (G) Screening of human MHC class I receptor variants by RT-PCR identified KIR3DL2 as being highly and commonly expressed in FALS and SALS astrocytes in vivo. (H) Ingenuity pathway analysis of fold changes were observed between wild-type and SOD1$^{G93A}$ astrocytes using the Mouse Natural Killer Cell 96 StellARay. Molecules in red represent transcripts that were upregulated. Molecules in green represent transcripts that were downregulated. The different shades represent the different fold changes from higher (>4) to lower (<3). Molecules in white did not display a significant fold change, while molecules in black represent genes that were not included in the array and were not further investigated.
Figure 5B:
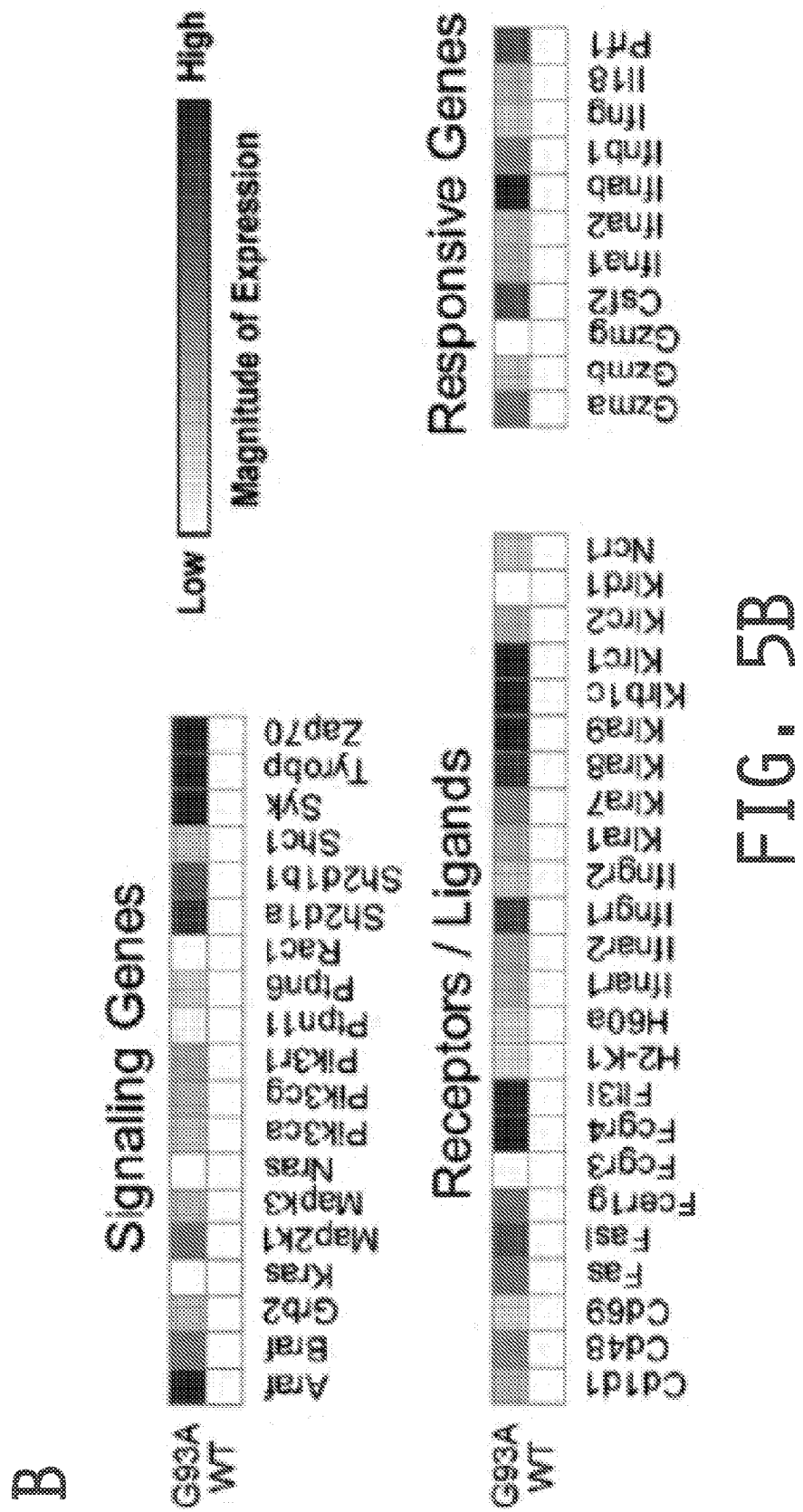

With the active use of the PRF1/GZMB cell death pathway, ALS astrocytes have adopted a functional property of NK cells. To characterize the extent of this apparent change in cell phenotype, this example evaluated the expression levels of a large series of NK cell associated markers in ALS astrocytes. SOD1$^{G93A}$ astrocytes expressed robust levels of two prototypical NK markers, CD56 and CD57, which are minimally expressed in wild type astrocytes (see FIG. 5A). Furthermore, qRT-PCR analysis of a large set of genes that included receptors, ligands, and intermediary signaling proteins known to be involved in NK activation, revealed upregulation of the majority of these genes in SOD1$^{G93A}$ astrocytes but in not wild-type controls (see FIG. 5B).

Figure 5C:
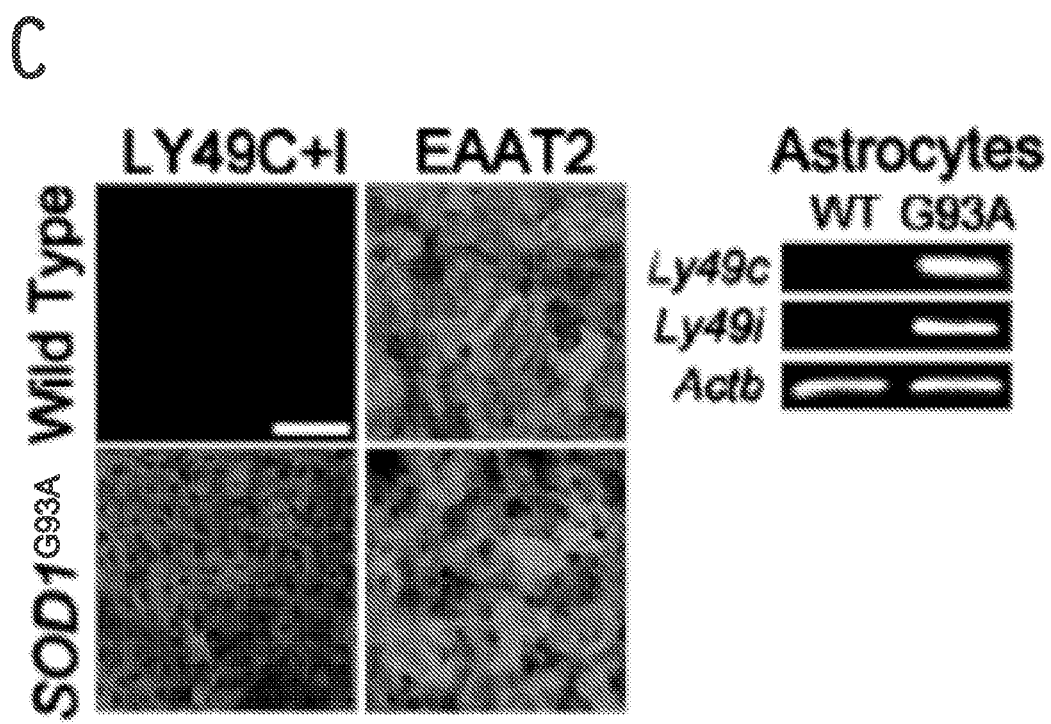

NK cells have evolved specific mechanisms to effectively mediate host defense mechanisms against viral infection that require the ability to identify infected from uninfected cells. Normally, the interaction of inhibitory receptors on the surface of NK cells with major histocompatibility complex (MHC) class I antigens presented by endogenous cells leads to suppression of NK cell activity. However, infection with certain viruses, such as Herpes Simplex Virus (HSV), suppresses MHC class I antigen presentation on the surface of the infected cell, triggering NK cytotoxicity. To determine if ALS astrocytes had acquired similar properties, including the ability to interact with MHC class I antigens, the presence of the MHC class I inhibitory receptors LY49C and LY49I was evaluated. Both receptors were highly expressed in SOD1$^{G93A}$ astrocytes cultured in vitro, but were absent from wild type astrocytes (see FIG. 5C). Gene expression analysis revealed activation of the NK cell signaling pathway in SOD1$^{G93A}$ astrocytes (see FIG. 5H).

Figure 5D:
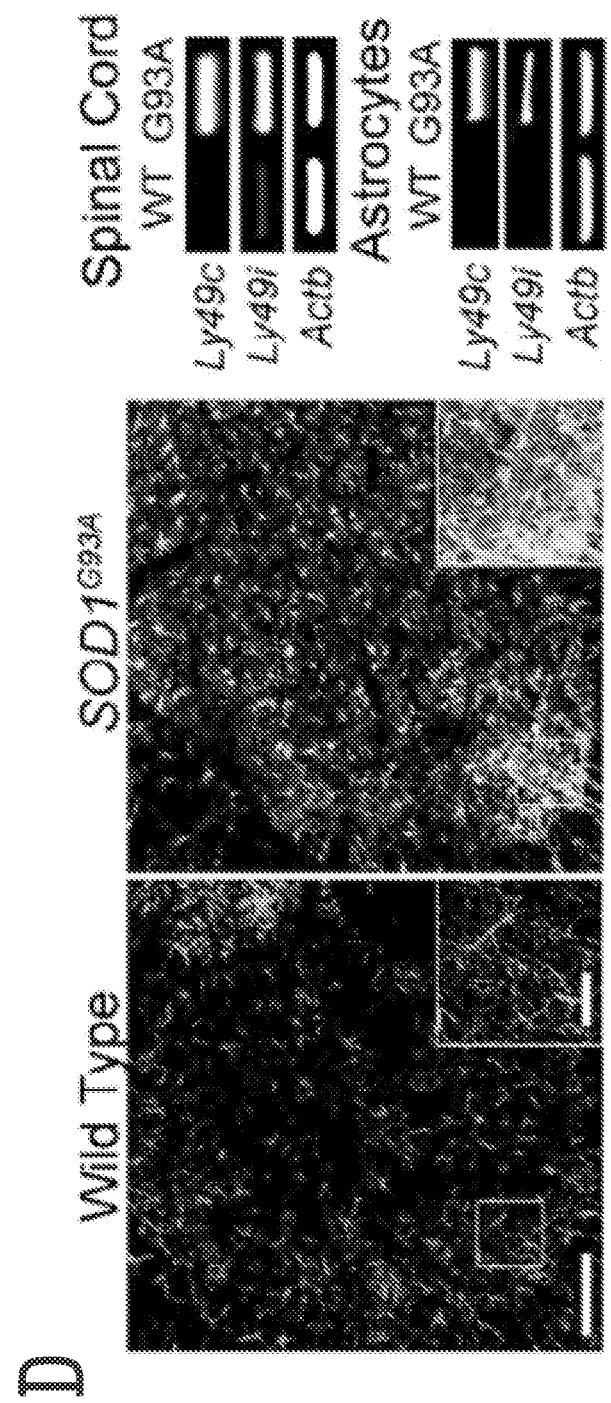
Figures 5E, 5F:
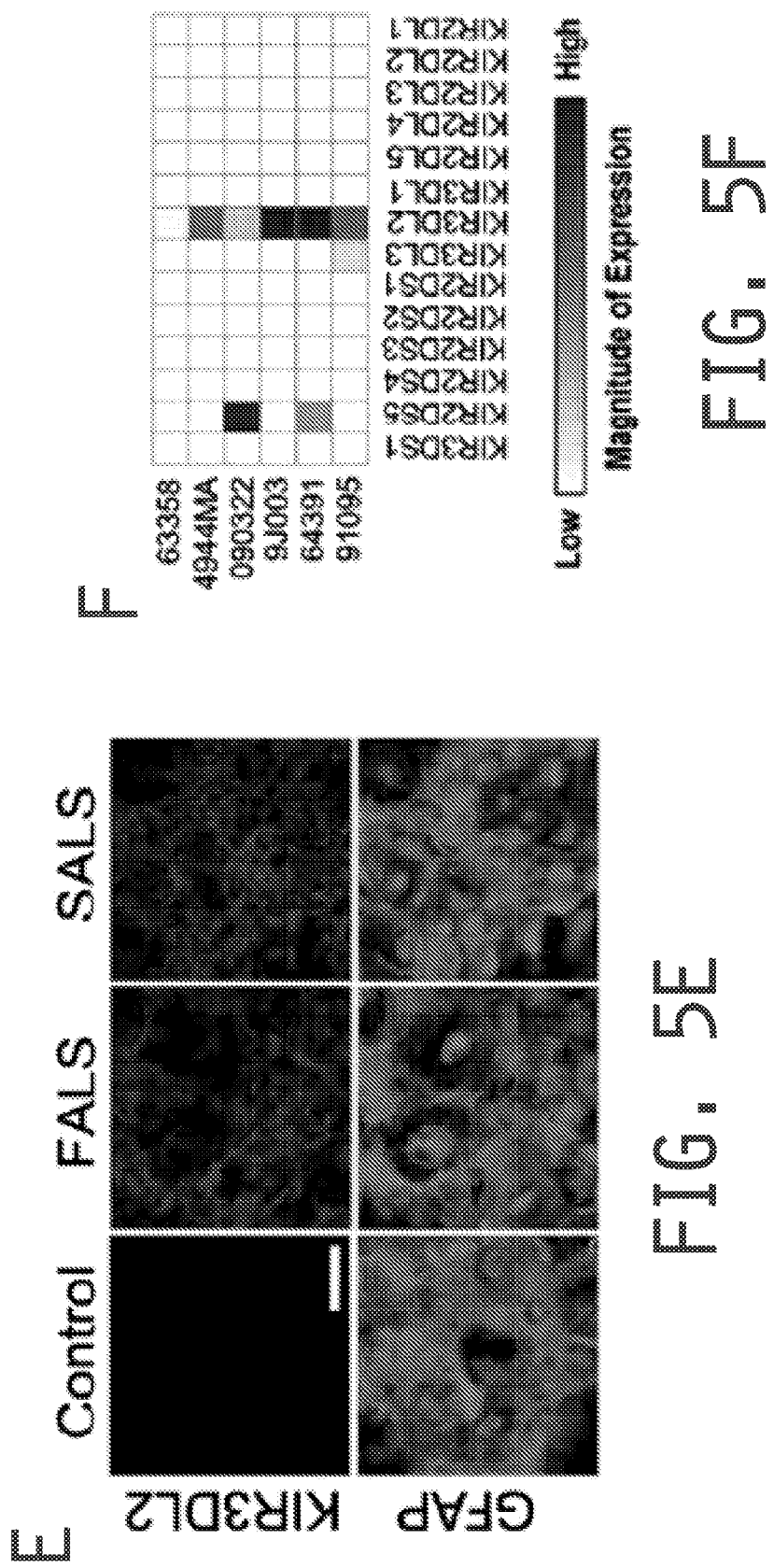
Figure 5G:
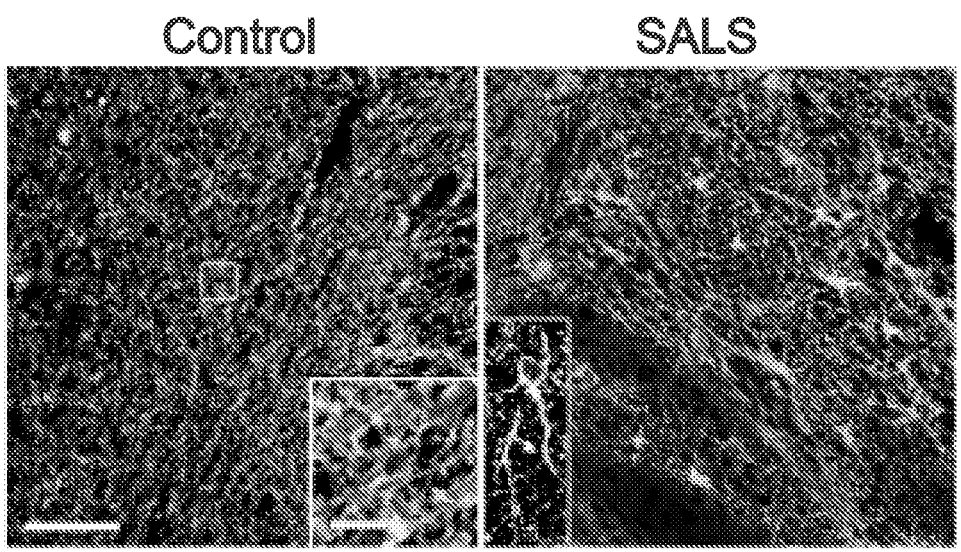
Figure 5H:
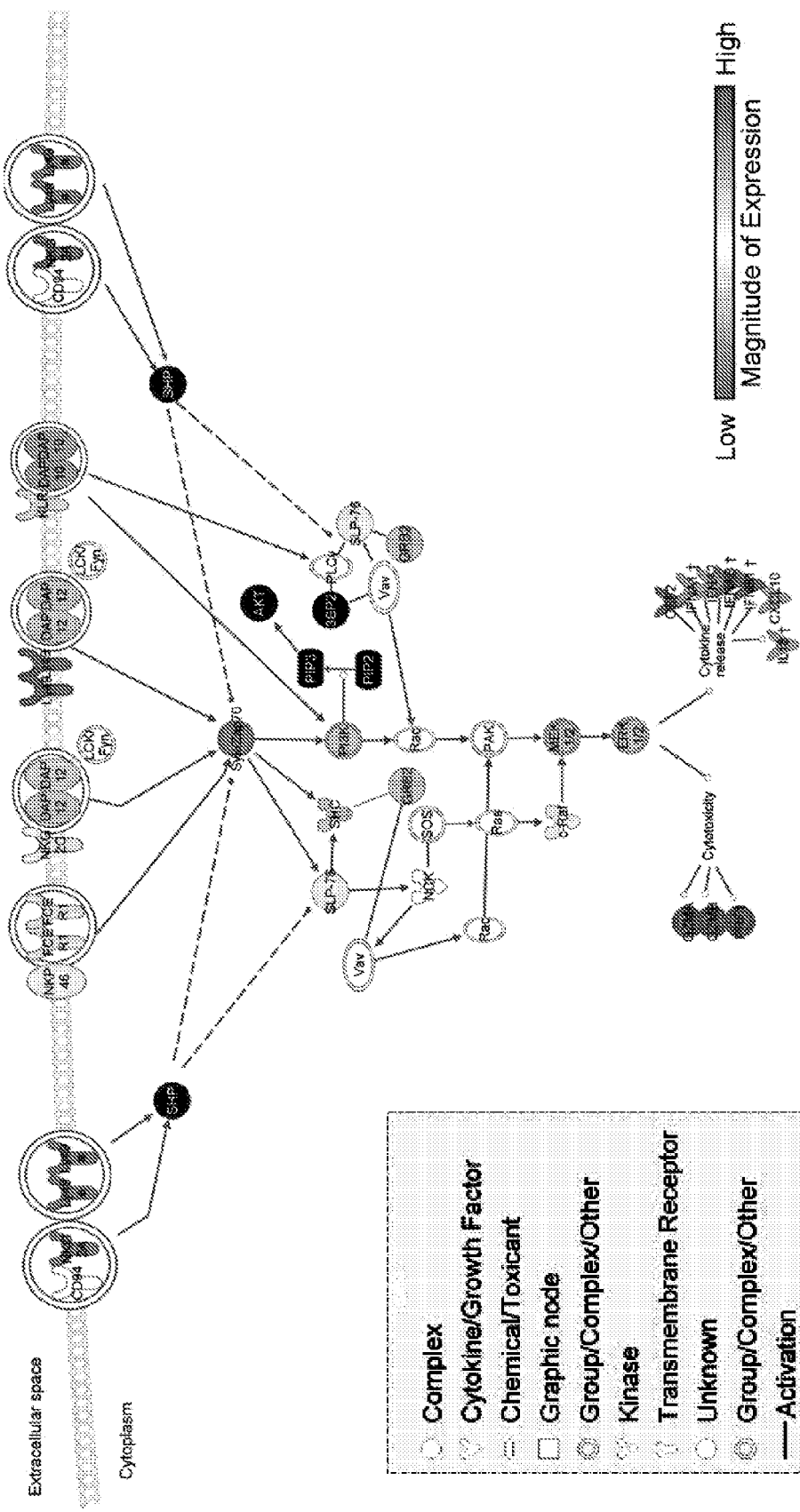

In vivo analyses on both protein and transcript level confirmed substantial expression of LY49C and LY49I in the spinal cords and within astrocytes of SOD1$^{G93A}$ mice while being absent from these tissues in control mice (see FIG. 5D). MHC class I receptors were present in NPC derived astrocytes obtained from post-mortem samples from FALS and SALS patients (see FIGS. 5E and 5F). The expression of fourteen MHC class I receptors in human ALS astrocytes was evaluated. Killer cell immunoglobulin-like receptor 3DL2 (KIR3DL2), a MHC class I inhibitory receptor was expressed specifically and highly in all FALS and SALS astrocyte lines evaluated but not in normal control cells (see FIG. 5F). Immunostaining confirmed high levels of KIR3DL2 in astrocytes within the spinal cord of ALS patients but not of healthy controls. These results suggest that ALS astrocytes not only activate the perforin/granzyme cell death pathway similar to NK cells, but also adopt many other NK cell properties including expression of MHC class I inhibitory receptors.

Example 6

Down-Regulation of MHC Class I is Associated with Motor Neuron Death

Figure 6A:
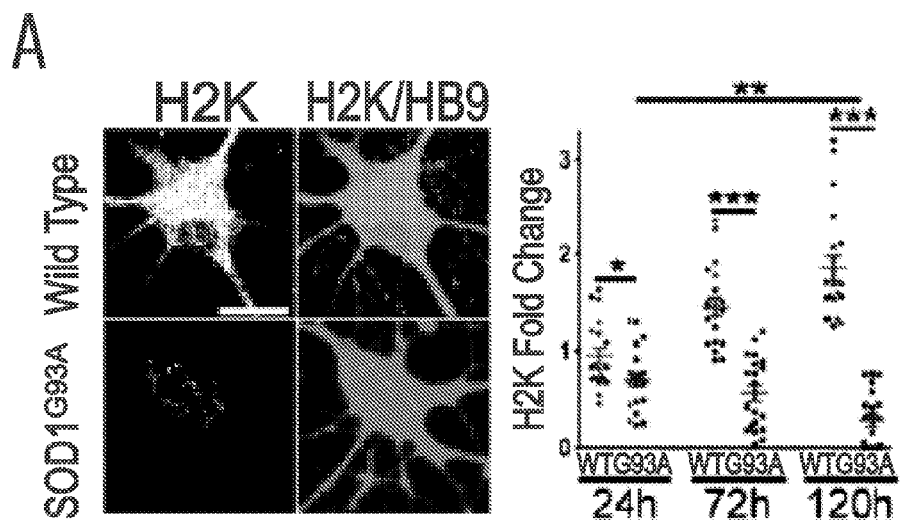
FIG. 6: (A) Time dependent down-regulation of MHC class I, evident from the intensity of H2K expression, in MNs upon co-culture with Sod1$^{G93A}$ astrocytes. Scale bars represent 10 μm. (B) Sod1$^{G93A}$ astrocytes do not induce MHC class I down-regulation in GABAergic neurons. Scale bars represent 5 μm. (C) Decreased expression of MHC class I in MNs at disease end-stage in Sod1$^{G93A}$ mice. H2K is shown in red; ChAT is shown in green. Asterisks in ALS panel mark MNs. Scale bars represent 2 mm and 10 μm (inset). (D) Decreased expression of MHC class I in MNs at disease end-stage in spinal cord of ALS patients. MHC class I is visualized by 3,3'-Diaminobenzidine (DAB) staining. Asterisks in ALS panel mark MNs. Scale bars represent 20 μm. (E) Quantification of MHC class I expression in MNs of human spinal cords shown in FIG. 6D. (F-G) Overexpression of MHC class I in MN prevents cell death (see panel 6F) as evident from HB9-GFP$^+$ cell numbers (see panel 6G). Scale bars represent 100 μm. (H) Sustained MHC class I expression in MNs upon co-culture with Sod1$^{G93A}$ astrocytes after lentiviral transduction. H2K is shown in red; Hb9 is shown in green. (I) MHC class I overexpression prevents atrophy of the MN soma. (J) MHC class I overexpression prevents shortening of neurites. *=p<0.05; =p<0.01; *=p<0.001; ns=non-significant. (K) Upon co-cultured with SOD1$^{G93A}$ astrocytes, surface MHC class I staining shows reduced expression of MHC class I on MNs transduced with Lv-RFP, but sustained expression of MHC class I on MN transduced with Lv-H2K. Scale bar represents 20 □M.

MHC class I inhibitory receptors expressed on the surface of ALS astrocytes may mediate an NK-cell like interaction with target cells, with reduced presentation of MHC class I by MNs triggering ALS astrocyte toxicity. First, levels of MHC class I receptors on the surface of MNs were monitored upon co-culture with astrocytes. While MNs cultured on top of wild type astrocytes sustained robust MHC class I expression for over 120 hours, MNs co-cultured with SOD1$^{G93A}$ astrocytes exhibited a rapid and marked decrease of MHC class I antigen (see FIG. 6A). This reduction was significant at 24 hours and became more marked with longer time in co-culture, with lowest MHC class I expression at 120 hours of co-culture (see FIG. 6A). Of note, the decrease in MHC class I expression on MN co-cultured with SOD1$^{G93A}$ astrocytes inversely correlated to the observed increase in the levels of PRF1/GZMB within MNs (see FIG. 2A).

Figure 6B:
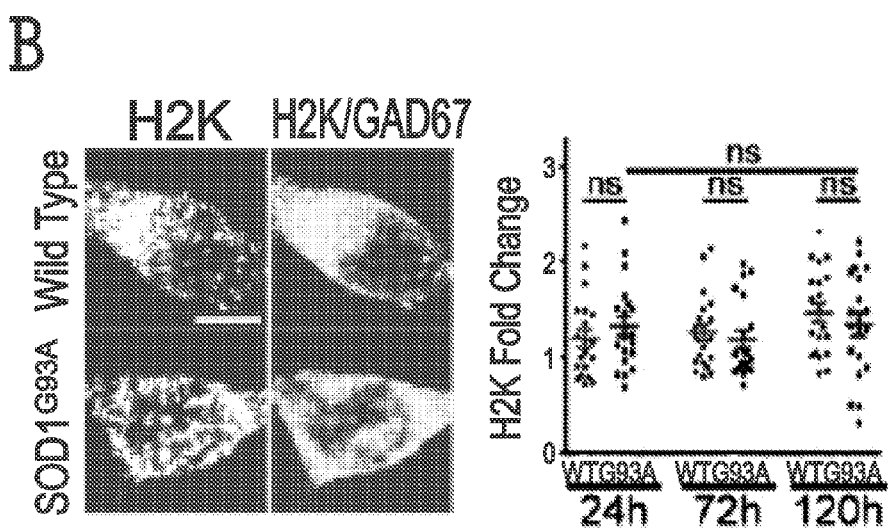

Since ALS astrocytes exert toxicity predominantly towards MNs but not towards other neuronal cell types such as GABA-ergic neurons, the levels of MHC class I on the surface of GABAergic neurons were evaluated. In contrast to the observed expression changes in MNs, MHC class I antigen levels in GABAergic neurons remained constant during extended co-cultured with wild type and SOD1$^{G93A}$ astrocytes (see FIG. 6B). These findings indicate that, similar to NK cells, ALS astrocytes recognize the levels of MHC class I expression by potential target cells. Furthermore, contact with ALS astrocytes appears to cause downregulation of MHC class I receptors specifically in MNs but not other neuronal cell types, rendering these cells the primary target cells for astrocyte mediated cytotoxicity in ALS.

Figure 6C:
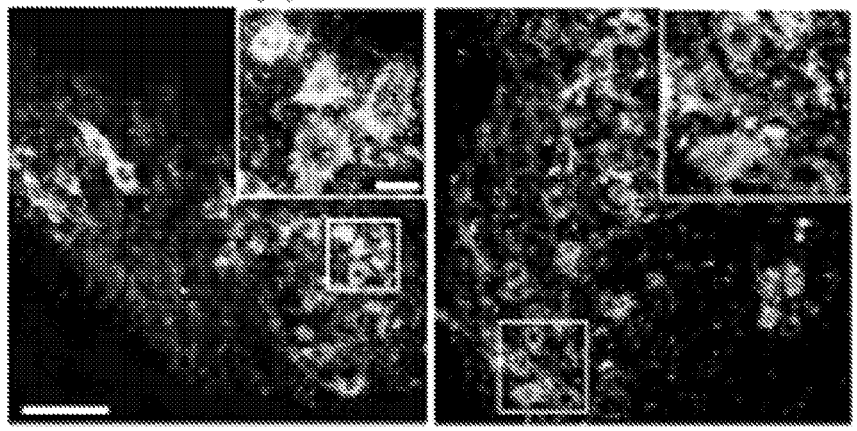
Figure 6D:
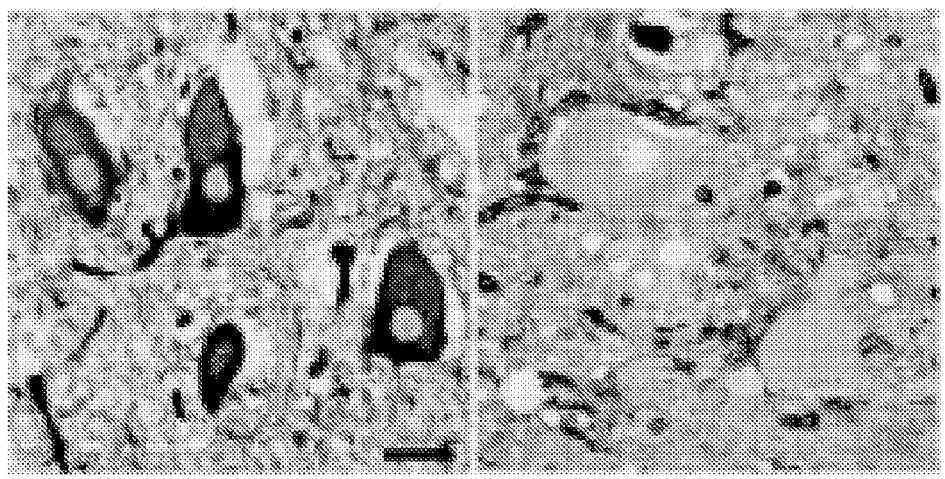
Figure 6E:
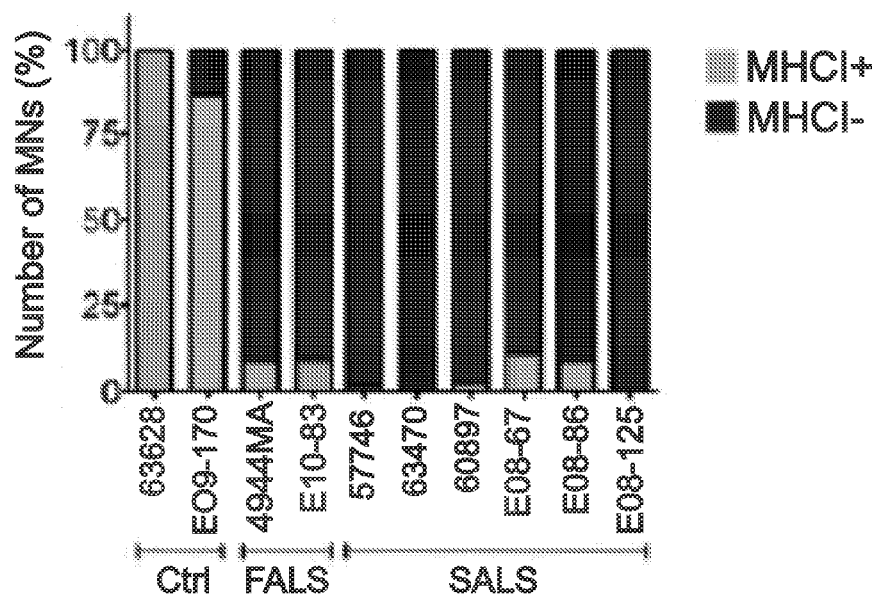

Second, in vivo confirmation of this specific decrease of MHC class I expression in MNs was investigated in both murine and human spinal cord specimens. Consistent with the in vitro results, MHC class I staining revealed widespread and substantial reduction of MHC class I expression in MNs only in the spinal cord of ALS patients or SOD1$^{G93A}$ mice, but not in normal tissues (see FIGS. 6C and 6D). Dramatic down-regulation of MHC class I in MNs was detected similarly in spinal cord samples of FALS and SALS patients, with absence of MHC class I receptors in 80 to 100% of MNs across samples (see FIG. 6E).

Figure 6F:
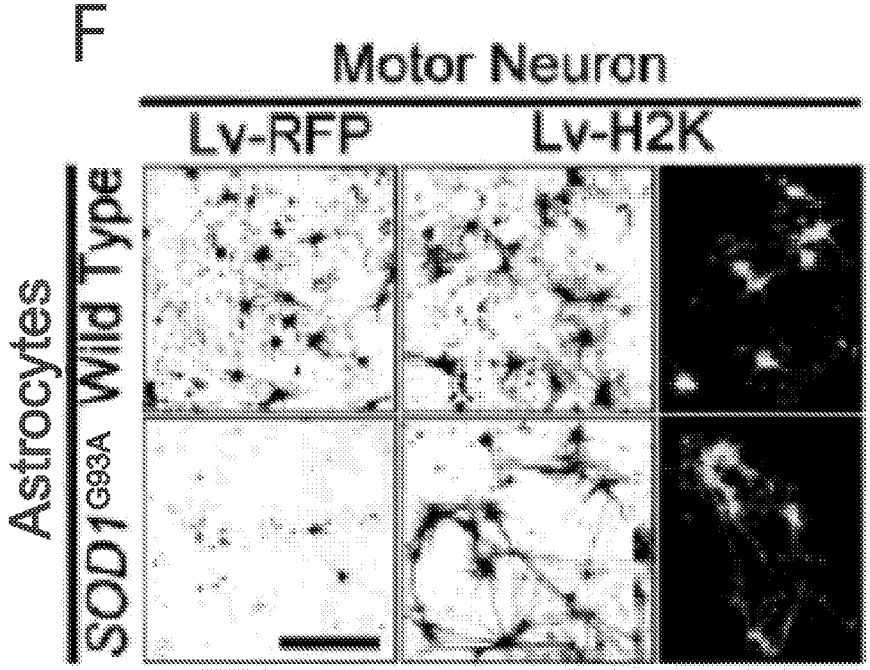
Figure 6G:
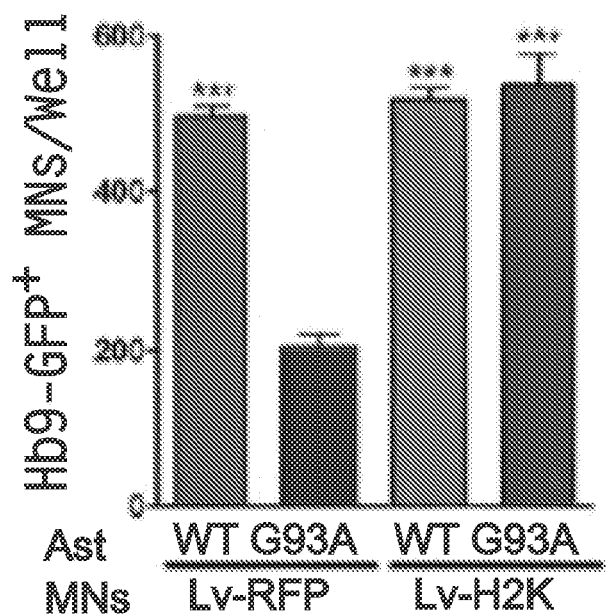
Figure 6H:
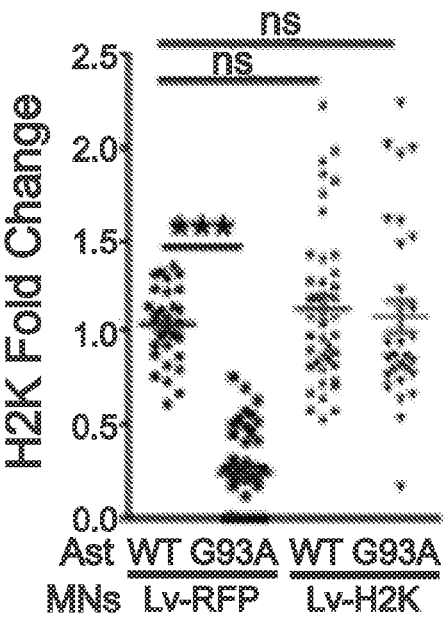
Figure 6I:
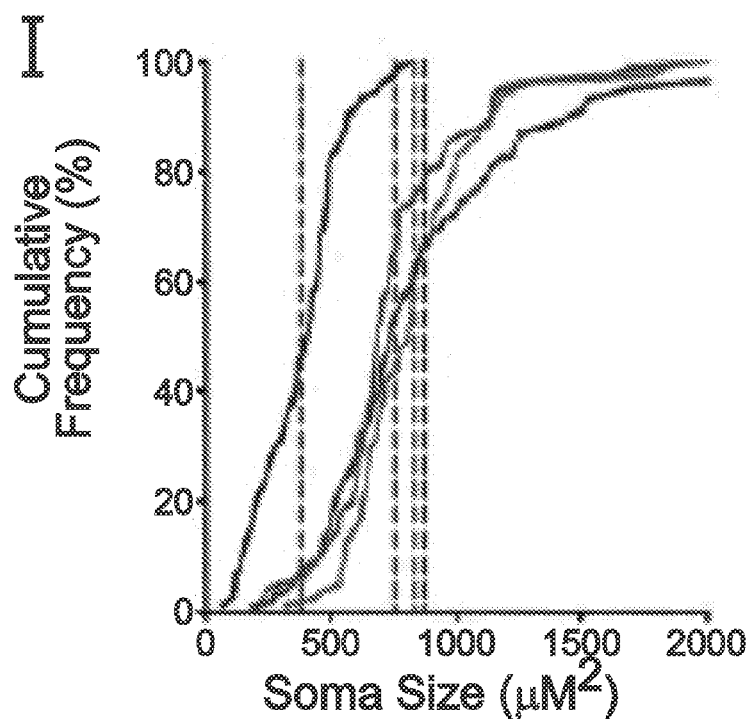
Figure 6J:
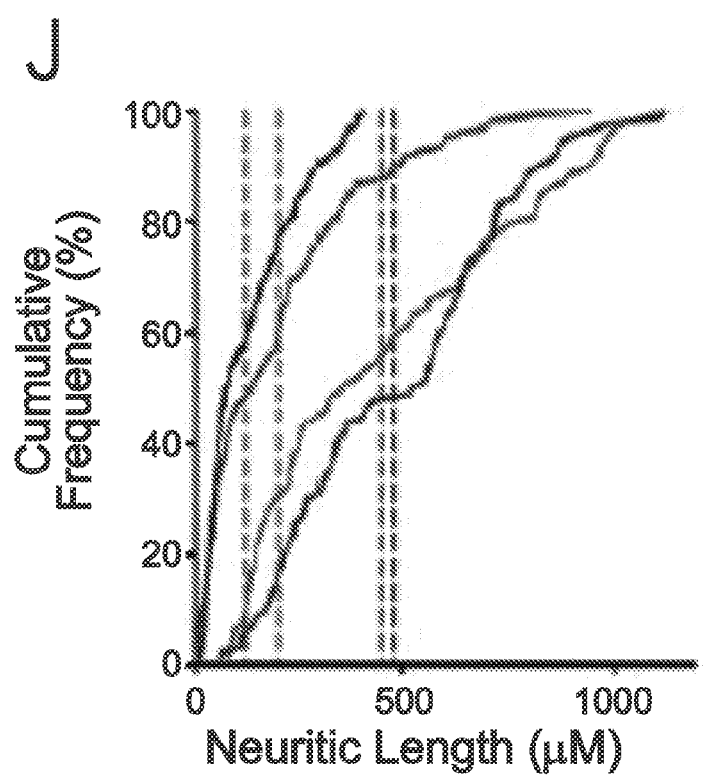
Figure 6K:
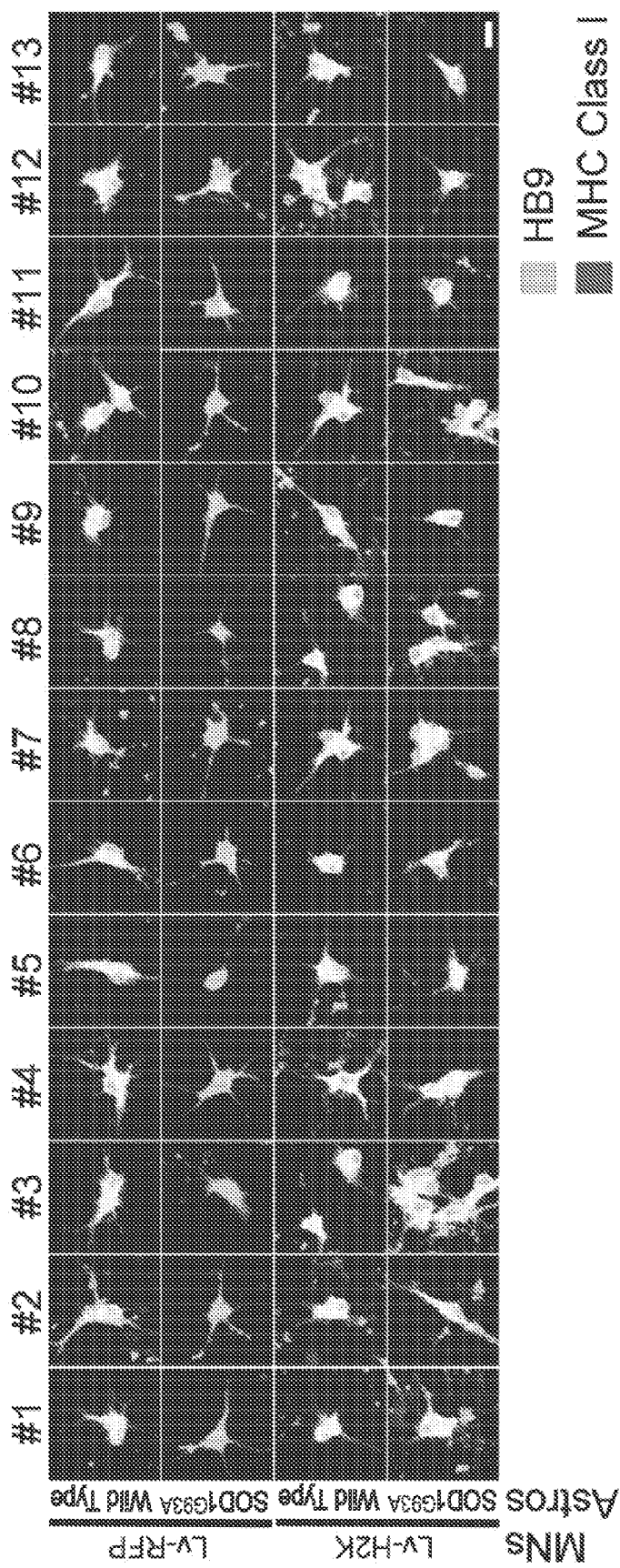

If the reduction of MHC class I observed in MNs upon co-culture with ALS astrocytes was the signal triggering astrocyte-derived toxicity, MNs should be spared if MHC class I expression could be sustained. This hypothesis was investigated by overexpressing MHC class I receptors in MNs by lentiviral delivery of the histocompatibility complex (H2K). Sustained expression of MHC class I in MNs protected these from the toxic effects of SOD1$^{G93A}$ astrocytes such that survival did not differ from MNs co-cultured with wild type astrocytes (see FIGS. 6F-6H). Upon co-cultured with SOD1$^{G93A}$ astrocytes, surface MHC class I staining shows reduced expression of MHC class I on MNs transduced with Lv-RFP, but sustained expression of MHC class I on MN transduced with Lv-H2K (see FIG. 6K). Rescue was also evident from unaltered soma size and neurite length of MNs co-cultured with SOD1$^{G93A}$ astrocytes (see FIGS. 6I and 6J). Sustained expression of the control transgene red fluorescent protein (RFP) in MNs did not alter SOD1$^{G93A}$ astrocyte mediated toxicity towards MNs, resulting in death of 80% of MNs after 120 hours of co-culture. These results suggest that constitutive expression of MHC class I receptors in MNs confers protection from cytotoxic effects induced by ALS astrocytes.

Figure 11A:
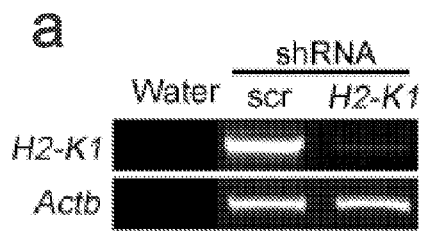
FIG. 11: (A-C) ShRNA knockdown of H2-K1 resulted in efficient down regulation of H2-K1 expression in GABAergic neurons as shown by RNA (A) and protein expression (B-C). (D) Suppression of H2-K1 in GABAergic neurons resulted in an increase incidence of PRF1 and GZMB upon co-culture with SOD1 astrocytes. (E-G), By 120 hours post co-culture with SOD1 astrocytes, GABA neurons treated with H2-K1 shRNA showed increased susceptibility to SOD1 mediated astrocyte toxicity as shown by a decrease in cell survival (E, F), soma size and neuritic length (F; n=3 for all groups, each n was run in triplicate). Dotted lines represent 50% frequency (G). Scale bars, 5 μm (B, D), 100 μm (E). Error bars denote s.e.m. P<0.01, **P<0.0001. Scr, scrambled shRNA.
Figure 11B:
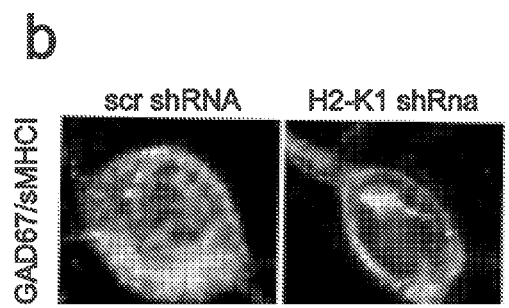
Figure 11C:
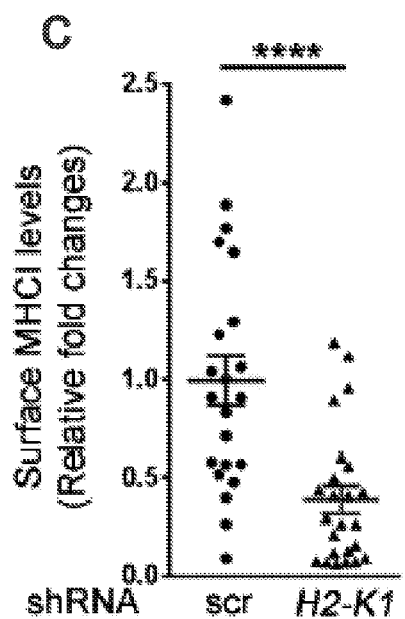
Figure 11D:
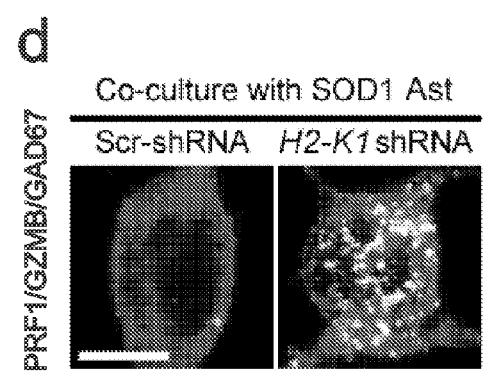
Figure 11E:
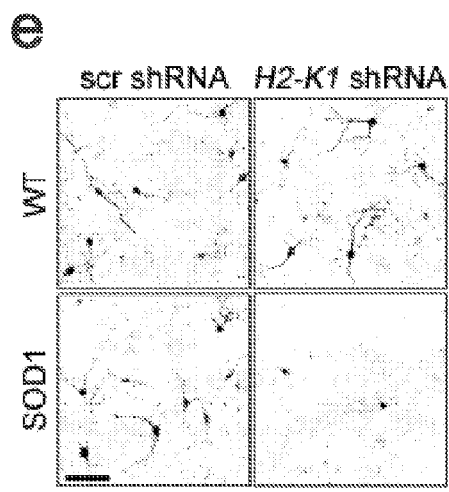
Figure 11F:
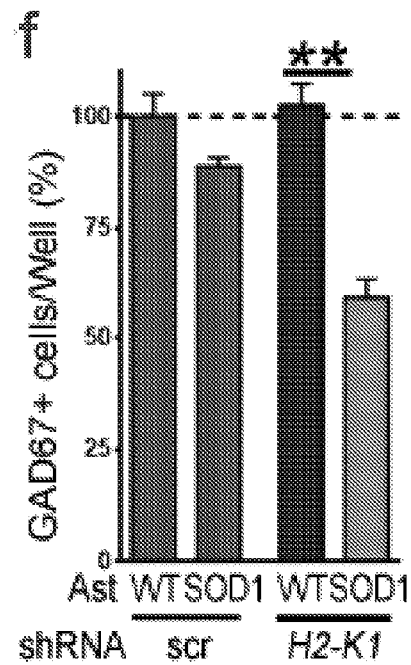
Figure 11G:
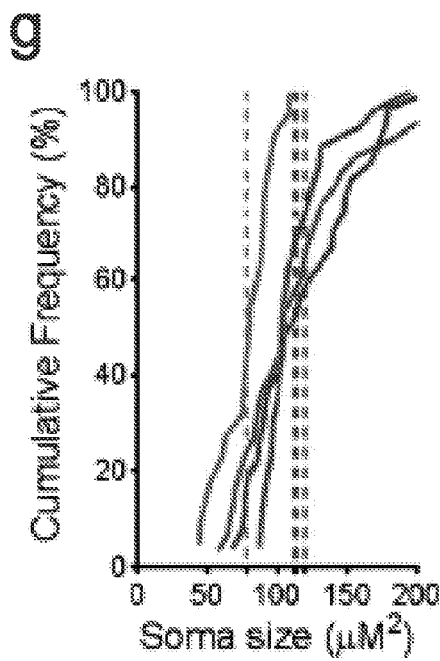

Furthermore, increased susceptibility of GABA neurons to SOD1 astrocyte mediated toxicity upon down regulation of MHCI expression was shown. ShRNA knockdown of H2-K1 resulted in efficient down regulation of H2-K1 expression in GABAergic neurons as shown by RNA (FIGS. 11A) and protein expression (FIGS. 11B and C). Suppression of H2-K1 in GABAergic neurons resulted in an increase incidence of PRF1 and GZMB upon co-culture with SOD1 astrocytes (FIG. 11D). By 120 hours post co-culture with SOD1 astrocytes, GABA neurons treated with H2-K1 shRNA showed increased susceptibility to SOD1 mediated astrocyte toxicity as shown by a decrease in cell survival (FIGS. 11E and F), soma size and neuritic length (FIG. 11F; n=3 for all groups, each n was run in triplicate). Dotted lines represent 50% frequency (FIG. 11G). Scale bars, 5 μm (FIGS. 11B and D), 100 μm (FIG. 11E). Error bars denote s.e.m. P<0.01, **P<0.0001. Scr, scrambled shRNA.

Example 7

Figure 7:
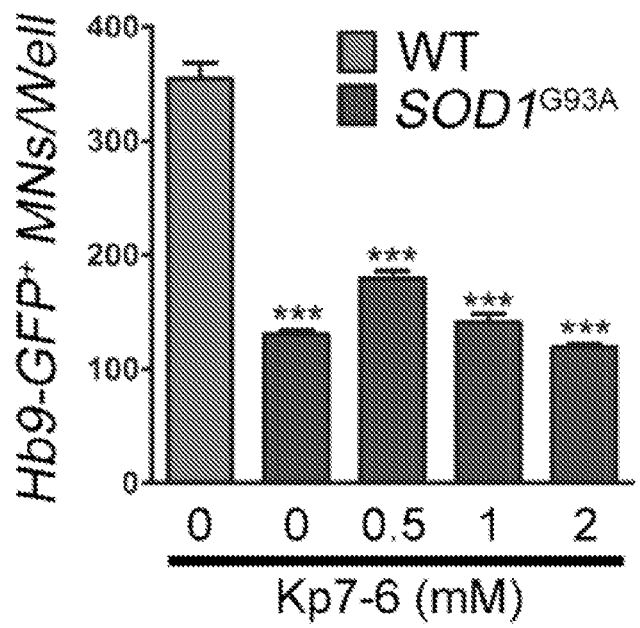
FIG. 7: Kp7-6 concentrations that are known to be effective in the inhibition of Fas/FasL activity in cytotoxic lymphocytes, did not change SOD1$^{G93A}$ astrocyte-derived toxicity towards MNs. ***, p<0.001.
Figure 8:
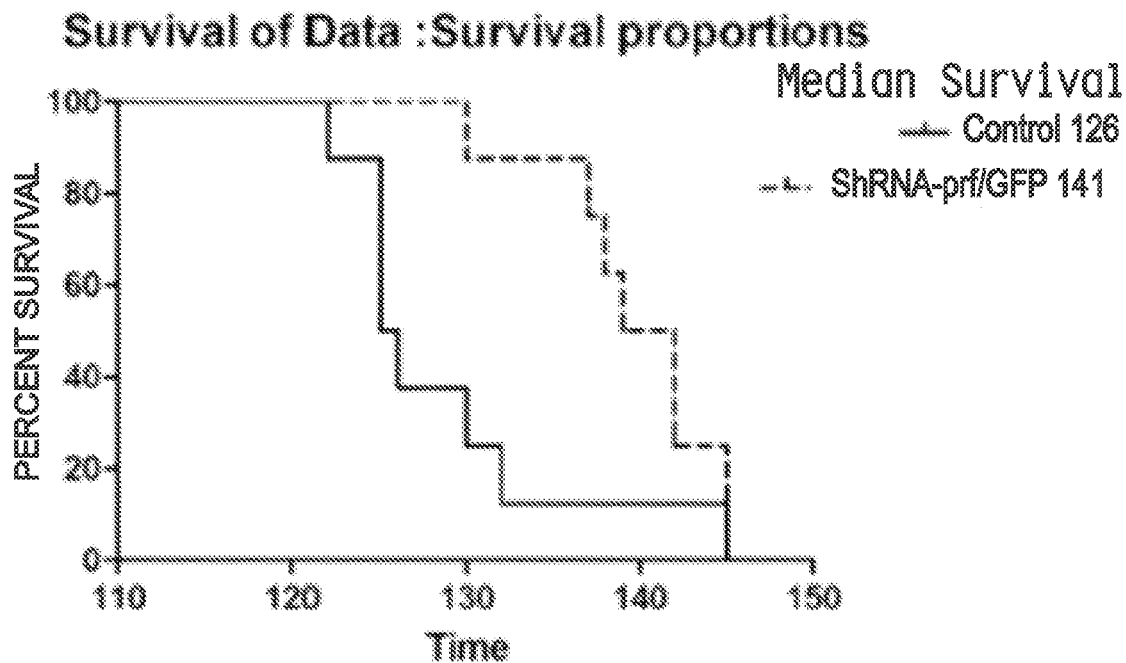
FIG. 8: The median survival rates of ShRNA-prf/GFP and control mice were analyzed. Results are shown in percent survival vs. time (days).
Figure 9:
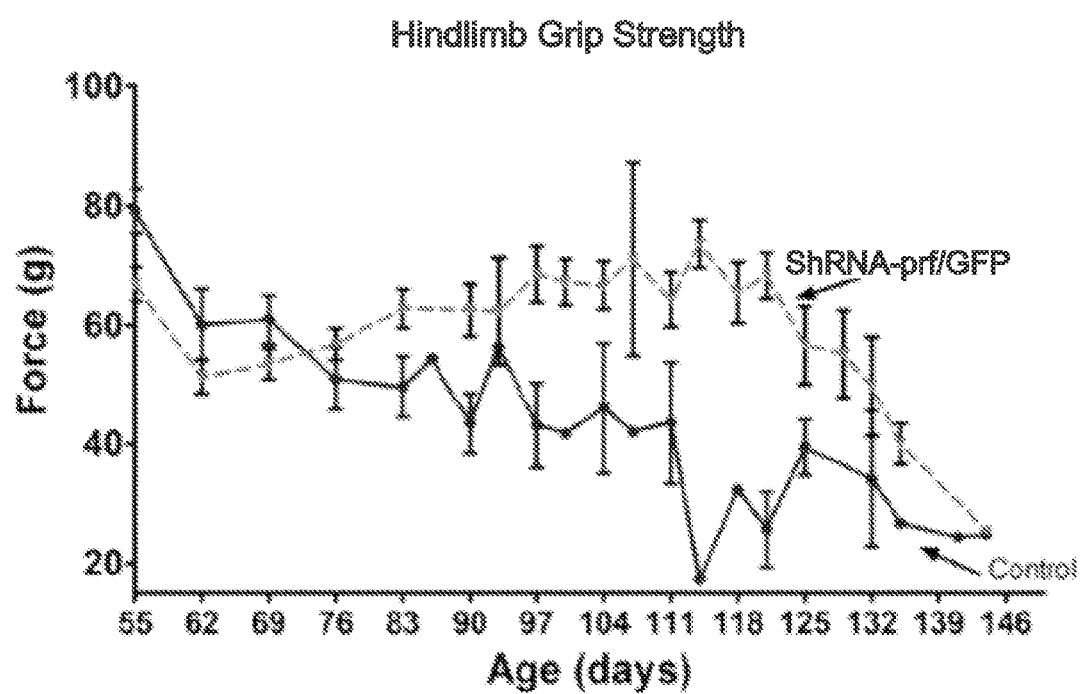
FIG. 9: The hindlimb grip strength of ShRNA-prf/GFP and control mice was analyzed. Results are shown as force (g) vs. age (days).

Selective Inhibition of Fas and FasL Signaling does not Prevent SOD1$^{G93A}$ Astrocyte Toxicity Towards Motor Neurons Kp7-6 was analyzed to determine whether Kp7-6 blocks astrocyte toxicity to MNs. Kp7-6 specifically antagonizes Fas/FasL-mediated apoptosis. Kp7-6 was added to SOD1$^{G93A}$ astrocytes 24 hours prior to MNs co-culture and maintained in the co-cultures at all times. Kp7-6 concentrations that are known to be effective in the inhibition of Fas/FasL activity in cytotoxic lymphocytes, did not change SOD1$^{G93A}$ astrocyte-derived toxicity towards MNs (see FIG. 7) ***, p<0.001.

Example 8

Animals

Transgenic mice that expressed mutant SOD1 (B6SJL-TgSOD1$^{G93A}$) were obtained from Jackson Laboratories (Bar Harbor, Me.). Animals were housed under light/dark (12:12 hour) cycle with food and water ad libitum. At each generation, SOD1$^{G93A}$ transgene copy number and SOD1 protein expression levels were verified by PCR and western blot analysis respectively. All procedures were performed in accordance with the NIH Guidelines and approved by the Nationwide Children's Research Institutional Animal Care and Use Committee.

Example 9

Isolation of Astrocytes from Mouse Spinal Cords

Astrocytes were isolated from 110-130 days of age SOD1$^{G93A}$ and wild-type B6SJL mice. Astrocyte cultures were prepared as previously described with minor modifications. Briefly, spinal cords were enzymatically dissociated to single cells with a mixture of Papain (2.5 U/ml; Worthington Biochemical, Lakewood, N.J.), Dispase grade II (1 U/ml; Boehringer Mannheim Corporation, Indianapolis, Ind.) and Dnase I (250 U/ml; Worthington Biochemical) for about 20 minutes. After filtration with a 70 □M nylon mesh, cells were pelleted, resuspended in DMEM/F12 (Invitrogen, Carlsbad, Calif.) supplemented with 10% fetal bovine serum (FBS, Invitrogen) and 0.2% N2 supplement (Invitrogen) and plated onto 75 cm tissue culture flasks. Cells became confluent within 2 to 3 weeks and at this point plates were shaken overnight in order to remove potential microglia cells. Adherent confluent astrocytes were also treated with cytosine arabinose (20 μM, Sigma-Aldrich, St. Louis, Mo.) for 48 hours to kill rapidly dividing cells. Prior to analysis, astrocytes preparations were tested for the presence of cytotoxic T-lymphocytes (CTLs) and natural killer (NK) cells and found to be devoid of these cells types.

Example 10

Isolation of Microglia from Mouse Spinal Cords

Microglia were isolated from 110-130 days of age SOD1$^{G93A}$ and wild-type B6SJL mice following protocols previously described. Briefly, whole spinal cords were homogenized in Hank's Balanced Salt Solution (HBSS), pH 7.4. The resulting homogenates were passed through a 70 μm nylon cell strainer and centrifuged at 400×g for 6 minutes. Supernatants were removed and cell pellets were resuspended in 70% isotonic Percoll (GE Healthcare, Waukesha, Wis.) at room temperature. A discontinuous Percoll density gradient was set up as follows: 70%, 50%, 35%, and 0% isotonic Percoll. The gradient was centrifuged for 20 minutes at 2000×g and microglia were collected from the interphase between the 70% and 50% Percoll layers. Cells were washed, then resuspended in HBSS and used for RNA or protein isolation. Prior to analysis, microglia preparations were tested for the presence of CTLs and NK cells and found to be devoid of these cells types.

Example 11

Isolation of Mouse NPCs and Differentiation into Astrocytes

NPCs were isolated from the spinal cords of SOD1$^{G93A}$ and wild-type B6SJL mice according to methods previously described. Briefly, spinal cords were enzymatically dissociated to single cells with a mixture of Papain (2.5 U/ml; Worthington Biochemical), Dispase grade II (1 U/ml; Boehringer Mannheim Corporation) and Dnase I (250 U/ml; Worthington Biochemical) for about 20 to 30 minutes. After filtration with a 70 □M nylon mesh, cells were pelleted and resuspended in DMEM (Invitrogen) supplemented with 10% FBS. The cell suspension was mixed with an equal volume of isotonic Percoll (GE Healthcare) and centrifuged at 20,000×g for 30 minutes at room temperature. Cells from the low-buoyancy fraction (5-10 ml above the red blood cell layer) were harvested, washed thoroughly with D-PBS/PSF (Invitrogen) and plated in 60 mm uncoated plates. Cells were grown in growth medium (DMEM/F12, Invitrogen), with 1% N2 supplement (Invitrogen), 20 ng/ml of fibroblast growth factor-2 (FGF-2, Peprotech, Rocky Hill, N.J.) and 20 ng/ml of endothelial growth factor (EGF, Peprotech). Proliferating clusters of cells attached to the plates started to appear in about 10 to 15 days. At 70-80% confluence, cells were passaged onto polyornithine-laminin (P/L)-coated plates. In these proliferation conditions, we confirmed that mouse NPCs cultures were absent of astrocytes, microglia, CTLs and NK cells contaminants. Once cultures were established, NPCs from wild-type and SOD1$^{G93A}$ mice were used to differentiate astrocytes for the experiments described in the manuscript. NPC-derived astrocytes were obtained withdrawal of growth factors and supplementing the medium with 10% FBS (Invitrogen). The medium was changed every 3 days thereafter. Astrocytes matured for 7 days in 10% FBS medium prior to being used in experiments. Highly enriched astrocytes were obtained following this methodology with no detectable levels of microglia, CTLs or NK cells contaminants.

Example 12

Human Post-Mortem NPC Derived Astrocytes

Human NPC-derived astrocytes used in this study were previously described. Receipt of human tissue was granted through Nationwide Children's Hospital Institutional Review Board (IRB08-00402, Investigating the Role of Glia in Amyotrophic Lateral Sclerosis) and use of all human samples was in accordance with their approved protocols. Post-mortem spinal cords or brains were processed within 24 to 72 hours postmortem and used for isolation of NPCs. NPCs were kept under sterile conditions, tissue was diced and a single cell suspension was obtained by enzymatic dissociation of the tissue at 37° C. for 30 to 40 minutes with 2.5 U/ml papain (Worthington Biochemical), 250 U/ml of DNase I (Worthington Biochemical) and 1 U/ml neutral protease (Roche). After dissociation, the cell pellet was resuspended in DMEM/F12 (Invitrogen) with 10% FBS (Invitrogen), passed through a 70 μM filter and centrifuged. The cell pellet was resuspended in DMEM/F12 (Invitrogen) with 10% FBS (Invitrogen) and combined 1:1 with Percoll (GE Healthcare). The cell/Percoll mixture was centrifuged at 20,000×g for 30 min at 20° C. and the low buoyancy fraction (10 ml) above the red blood cell layer was collected. Cells were washed and resuspended in NPC medium containing DMEM/F12 (Invitrogen) supplemented with 10% FBS (Invitrogen), 10% BIT9500 (Stem Cell Technologies), 1% N2 supplement (Invitrogen), 20 ng/ml of FGF-2 (Peprotech), 20 ng/ml of EGF (Peprotech) and 20 ng/ml of PDGF-AB (Peprotech). NPCs were cultured on fibronectin (Chemicon) coated plates and after 24 hours, the media was replaced with serum-free NPC medium. Half of the medium was subsequently replaced every 2 days. NPCs were passaged when 60-70% confluence was reached in about 3 to 4 weeks. In proliferation conditions, we confirmed that human NPCs cultures were absent of astrocytes, microglia, CTLs and NK cells contaminants. Once NPC cultures were established, astrocytes differentiation was induced by withdrawal of growth factors and by supplementing the medium with 10% FBS (Invitrogen). In these conditions, astrocytes were readily generated and could be maintained for over 20 passages. Astrocytes were maintained on laminin-coated plates with media change every 3 days and passaging when cultures reached 80% confluence. A summary of the demographic information associated with NPC derived astrocytes is shown in Table 4.

TABLE 4

Demographic information associated with NPC derived astrocytes

| ID | Diagnosis | Age (yr.) | Gender | Time from Diagnosis to Death |
|---|---|---|---|---|
| 1800 | Non-ALS | <1 | N/A | N/A |
| 031300HC | Non-ALS | 52 | Female | N/A |
| HD011296-5E6C2-2 | Non-ALS | 61 | Male | N/A |
| 63358 | Non-ALS | 87 | Male | N/A |
| 4944MA | Familial ALS* | 57 | Male | 8 Months |
| 090322 | Sporadic ALS | 70 | Male | 20 Months |
| 9J003 | Sporadic ALS | 55 | Male | 14 Months |
| 64391 | Sporadic ALS | 64 | Male | 14 Months |
| 91095 | Sporadic ALS | 70 | Female | 60 Months |
| 64089 | Sporadic ALS | 67 | Male | 9 Months |

N/A, Non-available;
*Sequencing results confirm A4V mutation in the SOD1 locus

Example 13

Motor Neuron Differentiation from Embryonic Stem Cell

Mouse embryonic stem cells (mES cells) that express green fluorescent protein (GFP) driven by the Hb9 promoter (HBG3 cells) were used. ES cells were cultured on top of inactivated mouse fibroblasts (Millipore, Billerica, Mass.). MN differentiation was induced by plating 1-2×10⁶ mES cells per 10 cm dish in the presence of 2 μM retinoic acid (Sigma-Aldrich) and 2 μM purmorphamine (Calbiochem. Billerica, Mass.). After 5 days of differentiation, embryonic bodies were dissociated and sorted based on levels of GFP using a FACSVantage/DiVa sorter (BD Biosciences, Rockville, Md.).

Example 14

NPC Differentiation into GABAergic Neurons

Mouse NPCs were induced to differentiate into GABAergic neurons by supplementing growth medium with 0.1% FBS (Invitrogen), retinoic acid (1 μM, Sigma-Aldrich), and forskolin (5 μM, Sigma-Aldrich). Media were changed every day. Cultures were allowed to differentiate for 7 days prior to be used for experiments.

Example 15

Co-Culture of Astrocytes and MNs

For co-culture experiments of mouse astrocytes and MNs, astrocytes were plated at the density of 40,000 cells per well at 96-well plates coated with laminin. After 48 hours, FACS sorted GFP⁺ MNs were plated on top of the astrocyte monolayer at a density of 2,000 cells per well. Co-culture was performed in MN media composed of DMEM/F12 (Invitrogen) supplemented with 5% horse serum (Equitech Bio, Kerrville, Tex.), 2% N2 supplement (Invitrogen), 2% B27 supplement (Invitrogen), 10 ng/ml of GDNF (Invitrogen), 10 ng/ml BDNF (Invitrogen), 10 ng/ml CNTF (Invitrogen). Half of media was replaced every other day, with addition of fresh growth factors. For co-culture of human astrocytes and MNs, astrocytes were plated at a density of 10,000 cells per well in 96-well plates coated with laminin. After 48 hours, GFP$^+$ MNs were seeded on top of the astrocytes at a density of 10,000 cells per well. Twenty four hours after MNs seeding, cytosine arabinose (1 µM, Sigma-Aldrich) was added for 48 hours to eliminate any remaining dividing astrocytes or undifferentiated embryonic stem cells. Media was changed every other day and growth factors were added.

Example 16

RNA isolation and RT-PCR

RNA was harvested using the RT$^2$ q-PCR-grade RNA isolation kit (Qiagen, Frederick, Md.) and total RNA was reverse transcribed with RT$^2$ First Strand Kit (Qiagen) according to the manufacturer's instructions. For semi-quantitative RT-PCR, transcripts were amplified using the following gene-specific primers: prf1-F: 5' -GTCACGTC-GAAGTACTTGGTG-3' (SEQ ID NO: 9) ; prf1-R: 5'-ATG-GCTGATAGCCTGTCTCAG-3' (SEQ ID NO: 10) ; gzmb-F: 5'-CCTGCCCAGGCGCAATGTCA-3' (SEQ ID NO: 11) ; gzmb-R: 5'-TGGTCTTTGGGTCCCCCGCA-3' (SEQ ID NO: 12) ; Ly49c-F: 5'-TCCCACGATGAGTGAGCCA-3' (SEQ ID NO: 13) ; Ly49c-R: 5'-TACCTT-TAACTCTAGTTGGAAAA-3' (SEQ ID NO: 14) ; Ly49i-F: 5'-GATGAATGAGCCGGAGGTC-3' (SEQ ID NO: 15); Ly49i-R: 5'-TTTCACTGTTCCATCTGTCCT-3' (SEQ ID NO: 16); actb-F: 5'-GTGGGCCGCCCTAGGCACCA-3' (SEQ ID NO: 17) ; actb-R: 5'-CTCTTTGATGTCACGCAC-GATTTC-3' (SEQ ID NO: 18). Detection of human killer-cell immunoglobulin-like receptor transcripts (KIRs) was determined by quantitative RT-PCR using primer sets previously described (Thompson et al., Immunogenetics, Nov. 2006, 58, 865). Natural killer cells markers were assayed in SOD1$^{G93A}$ and wild-type derived astrocytes by quantitative RT-PCR taking advantage of the Mouse Natural Killer Cell 96StellARay (Lonza, Hopkinton, Mass.). This StellARay measures the expression of genes concerning many aspects of NK cell biology, including cell surface receptors, ligands, signaling molecules, adhesion molecules, mediators of cytotoxicity, cytokines and cytokine receptors. Quantitative RT-PCR reactions were performed in duplicate using RT$^2$ Real-Time SYBR Green/Rox PCR Master Mix (Qiagen) on an ABI Prism 7000 (Applied biosystems, Carlsbad, Calif.).

Example 17

Immunocytochemistry

Immunofluorescence staining used to visualize various antigens in cells, mouse spinal cord or paraffin embedded human spinal cords samples was performed with antibodies and respective dilutions listed in Table 2. For most antigens, samples were first incubated for 1 hour at room temperature in TBS containing 0.1% triton-X and 10% donkey serum, followed by incubation with the primary antibody for 48-72 hours at 4° C. Labeling with secondary antibodies conjugated to various fluorochromes was performed for 2 hours at room temperature. Detection of PRF1 and GZMB in paraffin embedded human tissue was achieved with biotinylated secondary antibodies, using the ABC and VectorRed Kit protocols (Vector Laboratories, Burlingame, Calif.). Tissue was briefly counterstaining with Hematoxylin QS solution (Vector Laboratories, Burlingame, Calif.). MHC class I staining was performed according to a previously described protocol, with minor modifications. Briefly, cell permeabilization was achieved using 0.05% triton-X for mouse spinal cord samples, and 0.1% saponin for human spinal cord samples. Incubation with primary and secondary antibodies was performed in 10% donkey serum without any detergent. For in vitro surface labeling, cells on coverslips were fixed, blocked and incubated with primary antibodies for 1 hour at room temperature without initial permeabilization. To verify membrane integrity, each sample was stained for intracellular protein TUJ1. The absence of TUJ1 staining confirmed intact membrane, and MNs with positive TUJ1 staining were excluded from analysis. A summary of the demographic information associated with the human spinal cord tissues used for immunostaining is shown in Table 3.

TABLE 2

Antibodies and respective dilutions

| Antigen | Company | Catalog Number | Host | Dilution Used | Application |
|---|---|---|---|---|---|
| Mouse Specimen | | | | | |
| PRF1 | Cell Signaling | 3693 | Rabbit | 1:200 | ICC |
| PRF1 | Cell Signaling | 3693 | Rabbit | 1:500 | Western |
| GZMB | Cell Signaling | 4275 | Rabbit | 1:200 | ICC |
| GZMB | Cell Signaling | 4275 | Rabbit | 1:500 | Western |
| CD107A | Abcam | ab25245 | Rat | 1:500 | ICC |
| CD107A | Abcam | ab25245 | Rat | 1:500 | Western |
| CD56 | Millipore | ab5032 | Rabbit | 1:200 | ICC |
| CD57 | Novus Biological | nbp1-19788 | Rabbit | 1:100 | ICC |
| LY49C/I | BD Pharmagin | 553273 | Mouse | 1:50 | ICC |
| MHC Class I | AbD Serotec | mca2398 | Rat | 1:100 | ICC |
| GFAP | Abcam | ab4674 | Chicken | 1:500 | ICC |
| EAAT2 | Gift from Dr. Jeffrey Rothstein | | Rabbit | 1:200 | ICC |
| ChAT | Millipore | ab144p | Goat | 1:200 | ICC |
| GAD67 | Millipore | MAB5406 | Mouse | 1:200 | ICC |
| GAPDH | Millipore | MAB374 | Mouse | 1:500 | Western |

TABLE 2-continued

Antibodies and respective dilutions

| Antigen | Company | Catalog Number | Host | Dilution Used | Application |
|---|---|---|---|---|---|
| Human Specimen | | | | | |
| PRF1 | Abcam | ab75573 | Mouse | 1:50 | ICC, IHC |
| PRF1 | Abcam | ab75573 | Mouse | 1:100 | Western |
| GZMB | Abcam | ab4059 | Rabbit | 1:50 | ICC, IHC |
| GZMB | Cell Signaling | 4275 | Rabbit | 1:500 | Western |
| KIR3DL2 | Abcam | ab95303 | Rabbit | 1:200 | ICC |
| HLA | Abcam | ab70328 | Mouse | 1:50 | IHC |
| GFAP | Abcam | ab4674 | Chicken | 1:500 | ICC |

TABLE 3

Demographic information associated with human spinal cord tissue

| ID | Diagnosis | Age (yr.) | Gender | Time from Diagnosis to Death | Spinal Cord Segments |
|---|---|---|---|---|---|
| 63628 | Non-ALS | 67 | Male | N/A | Thoracic |
| E09-170 | Non-ALS | 88 | Female | N/A | Lumbar |
| 4944MA | Familial ALS* | 57 | Male | 8 months | Thoracic |
| E10-83 | Familial ALS* | 65 | Female | 4 months | Lumbar |
| 57746 | Sporadic ALS | 61 | Male | 3 weeks | Lumbar |
| ALS1989 | Sporadic ALS | N/A | N/A | N/A | Thoracic |
| 63470 | Sporadic ALS | 67 | Male | 1.2 months | Lumbar |
| 60897 | Sporadic ALS | 62 | Female | N/A | Cervical |
| E08-67 | Sporadic ALS | 49 | Female | 2.5 years | Lumbar |
| E08-86 | Sporadic ALS | 71 | Male | 6 months | Lumbar |
| E08-125 | Sporadic ALS | 55 | Female | 1 year | Thoracic |

N/A, Non-available;
*Sequencing results confirm A4V mutation in the SOD1 locus

Example 18

Confocal Microcopy and 3D Image Reconstruction

All images were captured on a laser scanning confocal microscope (Carl Zeiss Microscopy, Thornwood, N.Y.) and 3D reconstitution was obtained using LSM 510 software (Carl Zeiss).

Example 19

MNs Cell Viability

At various time points in the co-culture of astrocytes and MNs, cell survival, neuritic length and somas size of MNs was recorded using a fully automated IN CELL 6000 cell imager (GE Healthcare). Images were processed with the Developer and Analyzer software packages (GE Healthcare).

Example 20

Viral Vectors

To knockdown PRF1 and GZMB levels in astrocytes, sequences from the RNAi Consortium lentiviral shRNA library were screened and relevant plasmids purchased from Open Biosystems. Clones TRCN0000077206 (CCACTC-CAAGGTAGCCAATTT (SEQ ID NO: 19)) and TRCN0000032742 (CCTATGGATATAAGGATGGTT (SEQ ID NO: 20)) were used to target PRF1 and GZMB in mouse astrocytes, respectively. Clones TRCN0000007942 (ACCTGAATCATGGCCACCTAA (SEQ ID NO: 21)) and TRCN0000006448 (CATTGTCTCCTATGGACGAAA (SEQ ID NO: 22)) were used to knockdown PRF1 and GZMB in human astrocytes, respectively. Scrambled shRNA were used as controls for PRF1 (GGCACTAC-CCGATCTATTACA (SEQ ID NO: 23)) and for GZMB (GACCGATACTCGCGATATATT (SEQ ID NO: 24)). These sequences were delivered by lentiviral particles produced by $CaCl_2$ mediated transient transfection of 293cells and virus collected from the supernatant by ultracentrifugation as described (Tiscornia et al., Nat Protoc, 2006, 1, 241). Briefly, viral particles were produced by transient transfection of 293 cells in the presence of the helper plasmids, VSV-G, MDL and REV. Transfection was obtained by $CaCl_2$ precipitation for 10 minutes followed by medium incubation for an additional 20 hours. Viral supernatant was collected every 24 hours for the next 96 hours and viral particles were pelleted by ultra-centrifugation at 50,000 ×g for 2 hours. Viral particles were aliquoted and stored frozen at −80 ° C. until used. Prior to addition to astrocytes, viral titer was obtained using Quick-titer lentivirus quantification kit follow manufacture's directions (CellBiolabs Inc, San Diego, Calif., USA).

H2K cDNA (Mm24845) was purchased from Genecopia (Rockville, Md.) and delivered to MNs via lentiviral vectors delivery. H2K cDNA was cloned under the CMV promoter. RFP expression was also obtained by the presence of an IRES in the lentiviral construct. Motor neurons were first infected with lenti-H2K with 20 viral particles per motor neuron. H2K expression was allowed to occur for 48 prior to astrocyte plating. Astrocyte-motor neuron co-cultures were followed for an additional 120 hours. Assay was performed by plating on a 96 well with 20,000 and 60,000 motor neurons and astrocytes, respectively.

Example 21

Screening of PRF1 and GZMB shRNAs Sequences

In order to knockdown PRF1 and GZMB expression in astrocytes, sequences from the RNAi Consortium lentiviral shRNA library (TRC-Mm1.0 and TRC-Hs1.0) were screened and purchased from Thermo Scientific (Waltham, Mass., USA). The following sequences were screened:

```
PRF1 sequences screened:
Mouse:
TRCN0000077203 (CTATGCATAGAGAGGCCACTA (SEQ ID NO:
25));

TRCN0000077204 (GCCCATTTGGTGGTAAGCAAT (SEQ ID NO:
26));
```

-continued

TRCN0000077205 (CGGTGTCGTGTGGAACAATAA (SEQ ID NO: 27));

TRCN0000077206 (CCACTCCAAGGTAGCCAATTT (SEQ ID NO: 28));

TRCN0000077207 (AGGGTGAAATTCTCCTACCAT (SEQ ID NO: 29)).

treated with shRNA for Perforin exhibited increased percent survival over time and increased hind limb grip strength versus controls.

Example 25

H2K ORF Sequence (SEQ ID NO: 49)
AGTGTCGCCGCGGACGCTGGATATAAAGTCCACGCAGCCCGCAGAACTCA GAAGTCGCGAATCGCCGACAGGTGCG<u>ATG</u>GTACCGTGCACGCTGCTCCTG

CTGTTGGCGGCCGCCCTGGCTCCGACTCAGACCCGCGCGGGCCCACACTC

GCTGAGGTATTTCGTCACCGCCGTGTCCCGGCCCGGCCTCGGGGAGCCCC

GGTACATGGAAGTCGGCTACGTGGACGACACGGAGTTCGTGCGCTTCGAC

AGCGACGCGGAGAATCCGAGATATGAGCCGCGGGCGCGGTGGATGGAGCA

GGAGGGGCCCGAGTATTGGGAGCGGGAGACACAGAAAGCCAAGGGCAATG

AGCAGAGTTTCCGAGTGGACCTGAGGACCCTGCTCGGCTACTACAACCAG

AGCAAGGGCGGCTCTCACACTATTCAGGTGATCTCTGGCTGTGAAGTGGG

GTCCGACGGGCGACTCCTCCGCGGGTACCAGCAGTACGCCTACGACGGCT

GCGATTACATCGCCCTGAACGAAGACCTGAAAACGTGGACGGCGGCGGAC

ATGGCGGCGCTGATCACCAAACACAAGTGGGAGCAGGCTGGTGAAGCAGA

GAGACTCAGGGCCTACCTGGAGGGCACGTGCGTGGAGTGGCTCCGCAGAT

ACCTGAAGAACGGGAACGCGACGCTGCTGCGCACAGATTCCCCAAAGGCC

CATGTGACCCATCACAGCAGACCTGAAGATAAAGTCACCCTGAGGTGCTG

GGCCCTGGGCTTCTACCCTGCTGACATCACCCTGACCTGGCAGTTGAATG

GGGAGGAGCTGATCCAGGACATGGAGCTTGTGGAGACCAGGCCTGCAGGG

GATGGAACCTTCCAGAAGTGGGCATCTGTGGTGGTGCCTCTTGGGAAGGA

GCAGTATTACACATGCCATGTGTACCATCAGGGGCTGCCTGAGCCCCTCA

CCCTGAGATGGGAGCCTCCTCCATCCACTGTCTCCAACATGGCGACCGTT

GCTGTTCTGGTTGTCCTTGGAGCTGCAATAGTCACTGGAGCTGTGGTGGC

TTTTGTGATGAAGATGAGAAGGAGAAACACAGGTGGAAAAGGAGGGGACT

ATGCTCTGGCTCCAGGCTCCCAGACCTCTGATCTGTCTCTCCCAGATTGT

AAAGTGATGGTTCATGACCCTCATTCTCTAGCG<u>TGA</u>AGACAGCTGCCTGG

AGTGGACTTGGTGACAGACAATGTCTTCTCATATCTCCTGTGACATCCAG

AGCCCTCAGTTCTCTTTAGTCAAGTGTCTGATGTTCCCTGTGAGCCTATG

GACTCAATGTGAAGAACTGTGGAGCCCAGTCCACCCCTCTACACCAGGAC

CCTGTCCCTGCACTGCTCTGTCTTCCCTTCCACAGCCAACCTTGCTGGTT

CAGCCAAACACTGAGGGACATCTGTAGCCTGTCAGCTCCATGCTACCCTG

ACCTGCAACTCCTCACTTCCACACTGAGAATAATAATTTGAATGTAACCT

TGATTGTTATCATCTTGACCTAGGGCTGATTTCTTGTTAATTTCATGGAT

TGAGAATGCTTAGAGGTTTTGTTTGTTTGTTTGATTGATTTGTTTTTTTG

AAGAAATAAATGATAGATGAATAAACTTCCAGAATCTGGGTCACTAAAAA

AAAAAAAAAAAAAAAAAAA

Example 26

Statistical Analyses

All statistical tests were performed by multiway analysis of variance followed by a Bonferroni post hoc analysis of mean differences between groups (GraphPad Prism, San Diego, Calif.). Each experiment was repeated three or four times and each time triplicates were used.

---

What is claimed is:

1. A method for treating a patient with amyotrophic lateral sclerosis by decreasing the expression of a cytoplasmic granule toxin in astrocytes of the patient, the method comprising the step of administering to the patient to treat amyotrophic lateral sclerosis a composition comprising an effective amount of a compound that decreases the expression of the cytoplasmic granule toxin in the astrocytes of the patient wherein the compound is a nucleic acid and wherein the compound inhibits the loss of motor neurons, thereby treating amyotrophic lateral sclerosis.

2. The method of claim 1 wherein the cytoplasmic granule toxin is a granzyme.

3. The method of claim 2 wherein the granzyme is granzyme B.

4. The method of claim 1 wherein the decreased expression of the cytoplasmic granule toxin results in an effect on motor neurons in the patient selected from the group consisting of an increase in the number of motor neurons, a decrease in soma atrophy, and an increase in neurite length after administration of the compound.

5. The method of claim 1 wherein the nucleic acid has the sequence of SEQ ID NO: 1.

6. The method of claim 1 wherein the nucleic acid has the sequence of SEQ ID NO: 2.

* * * * *

UNITED STATES PATENT AND TRADEMARK OFFICE
CERTIFICATE OF CORRECTION

Page 1 of 1

PATENT NO. : 9,539,307 B2
APPLICATION NO. : 14/428765
DATED : January 10, 2017
INVENTOR(S) : Brian Kaspar It is certified that error appears in the above-identified patent and that said Letters Patent is hereby corrected as shown below:

In the Specification

Column 1 Lines 18-21 replace with the following:
"This invention was made with Government support under NS069476, NS064492 and NS058224 awarded by the National Institutes of Health. The Government has certain rights in the invention."

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 49

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acctgaatca tggccaccta a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cattgtctcc tatggacgaa a                                              21

<210> SEQ ID NO 3

-continued

```
<211> LENGTH: 1110
<212> TYPE: DNA
<213> ORGANISM: Mus musculus

<400> SEQUENCE: 3
atggtaccgt gcacgctgct cctgctgttg gcggccgccc tggctccgac tcagacccgc      60
gcgggcccac actcgctgag gtatttcgtc accgccgtgt cccggcccgg cctcggggag     120
ccccggtaca tggaagtcgg ctacgtggac gacacggagt tcgtgcgctt cgacagcgac     180
gcggagaatc cgagatatga ccgcggggcg cggtggatgg agcaggaggg gcccgagtat     240
tgggagcggg agacacagaa agccaagggc aatgagcaga gtttccgagt ggacctgagg     300
accctgctcg gctactacaa ccagagcaag ggcggctctc acactattca ggtgatctct     360
ggctgtgaag tggggtccga cgggcgactc ctccgcgggt accagcagta cgcctacgac     420
ggctgcgatt acatcgccct gaacgaagac ctgaaaacgt ggacggcggc ggacatggcg     480
gcgctgatca ccaaacacaa gtgggagcag gctggtgaag cagagagact cagggcctac     540
ctggagggca cgtgcgtgga gtggctccgc agatacctga gaacgggaa cgcgacgctg     600 ctgcgcacag attccccaaa ggcccatgtg accatcaca gcagacctga agataaagtc     660
accctgaggt gctgggccct gggcttctac cctgctgaca tcaccctgac ctggcagttg     720
aatggggagg agctgatcca ggacatggag cttgtggaga ccaggcctgc aggggatgga     780
accttccaga agtgggcatc tgtggtggtg cctcttggga aggagcagta ttacacatgc     840
catgtgtacc atcaggggct gcctgagccc ctcaccctga gatgggagcc tcctccatcc     900
actgtctcca acatggcgac cgttgctgtt ctggttgtcc ttggagctgc aatagtcact     960
ggagctgtgg tggcttttgt gatgaagatg agaaggagaa acacaggtgg aaaaggaggg    1020
gactatgctc tggctccagg ctcccagacc tctgatctgt ctctcccaga ttgtaaagtg    1080
atggttcatg accctcattc tctagcgtga                                      1110

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 4

Ile Glu Thr Asp
1

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 5

Ala Ala Val Ala Leu Leu Pro Ala Val Leu Leu Ala Leu Leu Ala Pro
1               5                   10                  15
```

Ile Glu Thr Asp
            20

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)
<220> FEATURE:
<223> OTHER INFORMATION: C-term FMK

<400> SEQUENCE: 6

Ile Glu Thr Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 7

Ile Glu Pro Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 8

Glu Ser Met Asp
1

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtcacgtcga agtacttggt g                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggctgata gcctgtctca g                                             21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgcccagg cgcaatgtca                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggtctttgg gtcccccgca                                               20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcccacgatg agtgagcca                                                19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tacctttaac tctagttgga aaa                                           23

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatgaatgag ccggaggtc                                                19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tttcactgtt ccatctgtcc t                                              21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gtgggccgcc ctaggcacca                                                20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ctctttgatg tcacgcacga tttc                                           24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ccactccaag gtagccaatt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
cctatggata taaggatggt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
acctgaatca tggccaccta a                                              21

<210> SEQ ID NO 22

<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cattgtctcc tatggacgaa a                                          21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcactaccc gatctattac a                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaccgatact cgcgatatat t                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctatgcatag agaggccact a                                          21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcccatttgg tggtaagcaa t                                          21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cggtgtcgtg tggaacaata a                                          21

<210> SEQ ID NO 28
<211> LENGTH: 21

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccactccaag gtagccaatt t                                           21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agggtgaaat tctcctacca t                                           21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccaacacaat tcttcttcca a                                           21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcctatgtga agctcttctt t                                           21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctcaggctt atctccaact a                                           21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgccgcttct acagtttcca t                                           21

<210> SEQ ID NO 34
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 34
acctgaatca tggccaccta a                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
cgagaatgtt atctaatgct a                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
cgagtttctt atcctggata a                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
gccttacttt cgatcaagga t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
cctatggata taaggatggt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
cagactataa tcctaagaca t                                              21

<210> SEQ ID NO 40
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 40
cgaatctgac ttacgccatt a                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcttatctta tgatctggga t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aatggtactg tcgtaataat g                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cattgtctcc tatggacgaa a                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcttcctgat acaagacgac t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccactccaag gtagccaatt t                                              21

<210> SEQ ID NO 46
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 46
acctgaatca tggccaccta a                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctatggata taaggatggt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cattgtctcc tatggacgaa a                                              21

<210> SEQ ID NO 49
<211> LENGTH: 1669
<212> TYPE: DNA
<213> ORGANISM: Mus musculus

<400> SEQUENCE: 49
agtgtcgccg cggacgctgg atataaagtc cacgcagccc gcagaactca gaagtcgcga    60
atcgccgaca ggtgcgatgg taccgtgcac gctgctcctg ctgttggcgg ccgccctggc   120
tccgactcag acccgcgcgg gcccacactc gctgaggtat ttcgtcaccg ccgtgtcccg   180
gcccggcctc ggggagcccc ggtacatgga agtcggctac gtggacgaca cggagttcgt   240
gcgcttcgac agcgacgcgg agaatccgag atatgagccg cgggcgcggt ggatggagca   300
ggaggggccc gagtattggg agcgggagac acagaaagcc aagggcaatg agcagagttt   360
ccgagtggac ctgaggaccc tgctcggcta ctacaaccag agcaagggcg gctctcacac   420
tattcaggtg atctctggct gtgaagtggg gtccgacggg cgactcctcc gcgggtacca   480
gcagtacgcc tacgacggct gcgattacat cgccctgaac gaagacctga aacgtggac    540 ggcggcggac atggcggcgc tgatcaccaa acacaagtgg gagcaggctg gtgaagcaga   600
gagactcagg gcctacctgg agggcacgtg cgtggagtgg ctccgcagat acctgaagaa   660
cgggaacgcg acgctgctgc gcacagattc cccaaaggcc catgtgaccc atcacagcag   720
acctgaagat aaagtcaccc tgaggtgctg ggccctgggc ttctaccctg ctgacatcac   780
cctgacctgg cagttgaatg gggaggagct gatccaggac atggagcttg tggagaccag   840
gcctgcaggg gatggaacct tccagaagtg ggcatctgtg gtggtgcctc ttggaaggaa   900
gcagtattac acatgccatg tgtaccatca ggggctgcct gagcccctca ccctgagatg   960
ggagcctcct ccatccactg tctccaacat ggcgaccgtt gctgttctgg ttgtccttgg  1020
agctgcaata gtcactggag ctgtggtggc ttttgtgatg aagatgagaa ggagaaacac  1080
aggtggaaaa ggaggggact atgctctggc tccaggctcc cagacctctg atctgtctct  1140

-continued

```
cccagattgt aaagtgatgg ttcatgaccc tcattctcta gcgtgaagac agctgcctgg   1200
agtggacttg gtgacagaca atgtcttctc atatctcctg tgacatccag agccctcagt   1260
tctctttagt caagtgtctg atgttccctg tgagcctatg gactcaatgt gaagaactgt   1320
ggagcccagt ccacccctct acaccaggac cctgtccctg cactgctctg tcttcccttc   1380
cacagccaac cttgctggtt cagccaaaca ctgagggaca tctgtagcct gtcagctcca   1440
tgctaccctg acctgcaact cctcacttcc acactgagaa taataatttg aatgtaacct   1500
tgattgttat catcttgacc tagggctgat ttcttgttaa tttcatggat tgagaatgct   1560
tagaggtttt gtttgtttgt ttgattgatt tgttttttg aagaaataaa tgatagatga   1620
ataaacttcc agaatctggg tcactaaaaa aaaaaaaaaa aaaaaaaa                1669
```